(12) United States Patent
Mathews et al.

(10) Patent No.: US 8,741,806 B2
(45) Date of Patent: Jun. 3, 2014

(54) HERBICIDES

(75) Inventors: Christopher John Mathews, Bracknell (GB); James Nicholas Scutt, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 0 days.

(21) Appl. No.: 13/384,478

(22) PCT Filed: Jul. 17, 2009

(86) PCT No.: PCT/EP2009/059211
§ 371 (c)(1),
(2), (4) Date: Apr. 5, 2012

(87) PCT Pub. No.: WO2011/006543
PCT Pub. Date: Jan. 20, 2011

(65) Prior Publication Data
US 2012/0190545 A1     Jul. 26, 2012

(51) Int. Cl.
*C07D 335/02* (2006.01)
*C07D 213/69* (2006.01)
*A01N 57/00* (2006.01)

(52) U.S. Cl.
USPC .............................. 504/103; 546/296; 549/28

(58) Field of Classification Search
None
See application file for complete search history.

(56) References Cited

U.S. PATENT DOCUMENTS 6,806,264 B2 * 10/2004 Lieb et al. ..................... 514/183

FOREIGN PATENT DOCUMENTS

| WO | 99/48869   | 9/1999  |
| WO | 01/79204   | 10/2001 |
| WO | 01/98288   | 12/2001 |
| WO | 2008/110307 | 9/2008  |

\* cited by examiner

*Primary Examiner* — Heidi Reese
(74) *Attorney, Agent, or Firm* — R. Kody Jones

(57) ABSTRACT

Compounds of formula (I) wherein the substituents are as defined in claim 1, are suitable for use as herbicides.

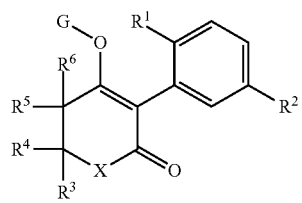

16 Claims, No Drawings

HERBICIDES

This application is a 371 of International Application No. PCT/EP2009/059211 filed Jul. 17, 2009, the contents of which are incorporated herein by reference.

The present invention relates to novel, herbicidally active cyclic diones, and derivatives thereof, to processes for their preparation, to compositions comprising those compounds, and to their use in controlling weeds, especially in crops of useful plants, or in inhibiting plant growth.

Cyclic diones having herbicidal action are described, for example, in WO99/48869, WO01/79204 and WO01/098288.

Novel cyclohexanedione, pyrandione, and piperidinedione compounds having improved herbicidal and growth-inhibiting properties have now been found. The present invention accordingly relates to compounds of formula I

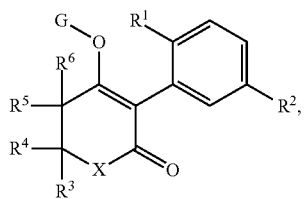

wherein
X is O, S, CR$^7$R$^8$ or NR$^9$,
R$^1$ is ethyl, cyclopropyl, difluoromethoxy or trifluoromethoxy,
R$^2$ is optionally substituted aryl or optionally substituted heteroaryl,
R$^3$ and R$^4$ are independently of each other, hydrogen, C$_1$-C$_3$alkyl or C$_1$-C$_3$haloalkyl, or
R$^3$ and R$^4$ together with the carbon atom to which they are attached form a three- to seven-membered carbocyclic ring, optionally substituted once or twice by C$_1$-C$_2$alkyl,
R$^5$, R$^6$, R$^7$ and R$^8$ are independently of each other hydrogen, C$_1$-C$_3$alkyl, C$_1$-C$_3$haloalkyl, C$_1$-C$_3$alkoxyC$_1$-C$_3$alkyl, C$_1$-C$_3$alkylthioC$_1$-C$_3$alkyl, C$_1$-C$_3$alkylsulfinylC$_1$-C$_3$alkyl, C$_1$-C$_3$alkylsulfonylC$_1$-C$_3$alkyl, C$_3$-C$_6$cycloalkyl in which a methylene group is optionally replaced by an oxygen or sulfur atom and wherein the ring is optionally substituted once or twice by C$_1$-C$_2$alkyl or C$_1$-C$_2$alkoxy, or
R$^5$ and R$^6$ together with the carbon atom to which they are attached, or R$^7$ and R$^8$ together with the carbon atom to which they are attached form an optionally substituted three- to seven membered carbocyclic ring, in which a methylene group is optionally replaced by an oxygen or sulfur atom and wherein the ring is optionally substituted once or twice by C$_1$-C$_2$ alkyl or C$_1$-C$_2$ alkoxy, or
R$^3$ and R$^6$ form a bond, when X is O, or S,
R$^9$ is hydrogen, optionally substituted C$_1$-C$_3$alkyl or optionally substituted C$_3$-C$_6$cycloalkyl, and
G is hydrogen or an agriculturally acceptable metal, ammonium, sulfonium or latentiating group.

In the substituent definitions of the compounds of the formula I, each alkyl moiety either alone or as part of a larger group (such as alkoxy, alkoxyalkyl, alkylthioalkyl) is a straight or branched chain and is, for example, methyl, ethyl, n-propyl or iso-propyl.

Haloalkyl groups are alkyl groups which are substituted with one or more of the same or different halogen atoms and are, for example, CF$_3$, CF$_2$Cl, CF$_2$H, CCl$_2$H, FCH$_2$, ClCH$_2$, BrCH$_2$, CH$_3$CHF, (CH$_3$)$_2$CF, CF$_3$CH$_2$ or CHF$_2$CH$_2$.

In the context of the present specification the term "aryl" preferably refers to phenyl and naphthyl. The term "heteroaryl" refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidinyl, triazinyl, thienyl, furyl, oxazolyl, isoxazolyl, 2,1,3-benzoxadiazolyl and thiazolyl.

Cycloalkyl includes preferably cyclopropyl, cyclobutyl, cyclopentyl and cyclohexyl.

Carbocyclic rings such as those formed together by any two of R$^7$ and R$^8$ or R$^5$ and R$^6$ include cycloalkyl and cycloalkenyl groups with 3 to 7 atoms, optionally including one or more, preferably 1 or 2 heteroatoms selected from O and S leading to heterocycles such as 1,3-dioxolane, oxetane, furan and tetrahydrofuran.

Agriculturally acceptable metals are alkali metal or alkaline earth metal ions, for example sodium, potassium, magnesium and calcium ions, and transition metal ions, for example copper and iron atoms. Suitable ammonium ions are NH$_4^+$, alkylammonium, dialkylammonium, triakylammonium and tetraalkylammonium ions. Suitable sulfonium ions are trialkylsulfonium ions, for example trimethylsulfonium ions.

It should be understood that in those compounds of formula I, where G is a metal, ammonium or sulfonium as mentioned above and as such represents a cation, the corresponding negative charge is largely delocalised across the O—C═C—C═O unit.

When present, the optional substituents on aryl and heteroaryl are selected independently, from halogen, nitro, cyano, rhodano, isothiocyanato, C$_{1-6}$ alkyl, C$_{1-6}$ haloalkyl, C$_{1-6}$ alkoxy-(C$_{1-6}$)alkyl, C$_{2-6}$ alkenyl, C$_{2-6}$ haloalkenyl, C$_{2-6}$ alkynyl, C$_{3-7}$ cycloalkyl (itself optionally substituted with C$_{1-6}$ alkyl or halogen), C$_{5-7}$ cycloalkenyl (itself optionally substituted with C$_{1-6}$ alkyl or halogen), hydroxy, C$_{1-10}$ alkoxy, C$_{1-10}$ alkoxy(C$_{1-10}$)alkoxy, tri(C$_{1-4}$)alkylsilyl(C$_{1-6}$) alkoxy, C$_{1-6}$ alkoxycarbonyl(C$_{1-10}$)alkoxy, C$_{1-10}$ haloalkoxy, aryl(C$_{1-4}$)alkoxy (where the aryl group is optionally substituted with halogen or C$_{1-6}$ alkyl), C$_{3-7}$ cycloalkyloxy (where the cycloalkyl group is optionally substituted with C$_{1-6}$ alkyl or halogen), C$_{3-10}$ alkenyloxy, C$_{3-10}$ alkynyloxy, mercapto, C$_{1-10}$ alkylthio, C$_{1-10}$ haloalkylthio, aryl(C$_{1-4}$)alkylthio, C$_{3-7}$ cycloalkylthio (where the cycloalkyl group is optionally substituted with C$_{1-6}$ alkyl or halogen), tri(C$_{1-4}$)-alkylsilyl(C$_{1-6}$)-alkylthio, arylthio, C$_{1-6}$ alkylsulfonyl, C$_{1-6}$ haloalkylsulfonyl, C$_{1-6}$ alkylsulfinyl, C$_{1-6}$ haloalkylsulfinyl, arylsulfonyl, tri(C$_{1-4}$)alkylsilyl, aryldi(C$_{1-4}$)-alkylsilyl, (C$_{1-4}$)alkyldiarylsilyl, triarylsilyl, C$_{1-10}$ alkylcarbonyl, HO$_2$C, C$_{1-10}$ alkoxycarbonyl, aminocarbonyl, C$_{1-6}$ alkylaminocarbonyl, di(C$_{1-6}$ alkyl)-aminocarbonyl, N—(C$_{1-3}$ alkyl)-N—(C$_{1-3}$ alkoxy) aminocarbonyl, C$_{1-6}$ alkylcarbonyloxy, arylcarbonyloxy, di($C_{1-6}$)alkylamino-carbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$)alkylamino, arylcarbonyl, (where the aryl group is itself optionally substituted with halogen or $C_{1-6}$ alkyl) or two adjacent positions on an aryl or heteroaryl system may be cyclised to form a 5, 6 or 7 membered carbocyclic or heterocyclic ring, itself optionally substituted with halogen or $C_{1-6}$ alkyl. Further substituents for aryl or heteroaryl include arylcarbonylamino (where the aryl group is substituted by $C_{1-6}$ alkyl or halogen), ($C_{1-6}$)alkoxycarbonylamino ($C_{1-6}$)alkoxycarbonyl-N—($C_{1-6}$)alkylamino, aryloxycarbonylamino (where the aryl group is substituted by $C_{1-6}$ alkyl or halogen), aryloxycarbonyl-N—($C_{1-6}$)alkylamino, (where the aryl group is substituted by $C_{1-6}$ alkyl or halogen), arylsulphonylamino (where the aryl group is substituted by $C_{1-6}$ alkyl or halogen), arylsulphonyl-N—($C_{1-6}$)alkylamino (where the aryl group is substituted by $C_{1-6}$ alkyl or halogen), aryl-N—($C_{1-6}$)alkylamino (where the aryl group is substituted by $C_{1-6}$ alkyl or halogen), arylamino (where the aryl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$ alkylaminocarbonylamino, di($C_{1-6}$)alkylaminocarbonylamino, arylaminocarbonylamino where the aryl group is substituted by $C_{1-6}$ alkyl or halogen), aryl-N—($C_{1-6}$)alkylamino-carbonylamino where the aryl group is substituted by $C_{1-6}$ alkyl or halogen), $C_{1-6}$ alkylaminocarbonyl-N—($C_{1-6}$)alkylamino, di($C_{1-6}$)alkylaminocarbonyl-N—($C_{1-6}$)alkylamino, arylaminocarbonyl-N—($C_{1-6}$)alkylamino where the aryl group is substituted by $C_{1-6}$ alkyl or halogen) and aryl-N—($C_{1-6}$)alkylaminocarbonyl-N—($C_{1-6}$)alkylamino where the aryl group is substituted by $C_{1-6}$ alkyl or halogen).

For substituted aryl moieties and heteroaryl groups it is particularly preferred that one or more substituents are independently selected from halogen, in particular chloro, cyano, $C_{1-6}$ alkyl, $C_{1-6}$ haloalkyl, in particular trifluoromethyl, $C_{1-6}$ alkoxy, in particular methoxy, $C_{1-6}$ haloalkoxy, $C_{1-6}$ alkylthio, $C_{1-6}$ alkylsulfinyl, $C_{1-6}$ alkylsulfonyl, nitro and cyano. It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected ($C_{1-6}$)alkyl groups. When heterocyclic rings are formed by joining two groups on an N atom, the resulting rings are suitably pyrrolidine, piperidine, thiomorpholine and morpholine each of which may be substituted by one or two independently selected ($C_{1-6}$) alkyl groups.

The invention relates also to the salts which the compounds of formula I are able to form with amines, alkali metal and alkaline earth metal bases or quaternary ammonium bases.

Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$-alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula [N($R_a$ $R_b R_c R_d$)]OH wherein $R_a$, $R_b$, $R_c$ and $R_d$ are each independently of the others $C_1$-$C_4$alkyl. Further suitable tetraalkylammonium bases with other anions can be obtained, for example, by anion exchange reactions.

The latentiating groups G are selected to allow their removal by one or a combination of biochemical, chemical or physical processes to afford compounds of formula I where G is H before, during or following application to the treated area or plants. Examples of these processes include enzymatic cleavage, chemical hydrolysis and photolyosis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

The latentiating group G is preferably selected from the groups —C($X^a$)—$R^a$, C($X^b$)—$X^c$—$R^b$, C($X^d$)—N($R^c$)—$R^d$, —$SO_2$—$R^e$, —P($X^e$)($R^f$)—$R^g$ or $CH_2$—$X^f$—$R^h$, wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{18}$haloalkyl, $C_1$-$C_{10}$cyanoalkyl, $C_1$-$C_{10}$nitroalkyl, $C_2$-$C_{10}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$ alkylsulfinyl, $C_1$-$C_3$ alkylsulfonyl, halogen, cyano or by nitro), heteroaryloxy$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

Preferably, G denotes hydrogen, an alkali metal or alkaline earth metal or a latentiating group.

In particular, the latentiating group G is a group —C($X^a$)—$R^a$ or —C($X^b$)—$X^c$—$R^b$, and the meanings of $X^a$, $R^a$, $X^b$, $X^c$ and $R^b$ are as defined above.

G as hydrogen is especially preferred.

Depending on the nature of the substituents G, $R^1$, $R^2$, $R^3$, $R^4$, $R^5$, $R^6$, $R^7$ and $R^8$, compounds of formula I may exist in different isomeric forms. When G is hydrogen, for example, compounds of formula I may exist in different tautomeric forms. Also, when substituents contain double bonds, cis- and trans-isomers can exist. This invention covers all such isomers and tautomers and mixtures thereof in all proportions. These isomers, too, are within the scope of the claimed compounds of the formula I.

It should be mentioned again that in those compounds of formula I, where G is a metal, ammonium (such as $NH_4+$; N(alkyl)$_4$+) or sulfonium (such as S(alkyl)$_3$+) cation, the corresponding negative charge is largely delocalised across the O—C=C—C=O unit.

Preferably, in the compounds of formula I X is O or $CR^7R^8$, where $R^7$ and $R^8$ are as defined above. More preferably, X is $CH_2$.

Preferably, $R^1$ is ethyl.

Preferably, $R^2$ is phenyl, naphthyl, a 5- or 6-membered heteroaryl or a bicyclic 8- to 10-membered heteroaryl, in each case optionally substituted by halogen, methyl, ethyl, trifluoromethyl, methoxy, difluoromethoxy, trifluoromethoxy, nitro or cyano.

More preferably, $R^2$ is phenyl, naphthyl, furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, in each case optionally substituted by halogen, methyl, ethyl, trifluoromethyl, methoxy, difluoromethoxy, trifluoromethoxy, nitro or cyano.

Even more preferably, $R^2$ is optionally substituted phenyl or optionally substituted pyridyl. In particular, $R^2$ is phenyl substituted one to three times by fluorine, chlorine, bromine, methoxy, methyl, cyano or trifluoromethyl.

Preferably, $R^3$ and $R^4$ independently, independently, hydrogen or $C_1$-$C_3$alkyl, Preferably, $R^5$, $R^6$, $R^7$ and $R^8$ are independently of each other hydrogen, $C_1$-$C_3$alkyl, $C_1$-$C_3$alkoxy$C_1$-$C_3$alkyl, optionally substituted $C_3$-$C_6$cycloalkyl in which a ring carbon atom is optionally replaced by an oxygen or sulfur atom and wherein the ring is optionally substituted once or twice by $C_1$-$C_2$ alkyl or $C_1$-$C_2$ alkoxy, or $R^5$ and $R^6$ together with the carbon atom to which they are attached or $R^7$ and $R^8$ together with the carbon atom to which they are attached form an optionally substituted three- to seven membered carbocyclic ring, in which a ring carbon atom is optionally replaced by an oxygen or sulfur atom and wherein the ring is optionally substituted once or twice by $C_1$-$C_2$alkyl or $C_1$-$C_2$ alkoxy. More preferably, $R^5$, $R^6$, $R^7$ and $R^8$ are independently of each other hydrogen, $C_1$-$C_3$alkyl, $C_1$-$C_3$alkoxy$C_1$-$C_3$alkyl, or $R^5$ and $R^6$ together with the carbon atom to which they are attached or $R^7$ and $R^8$ together with the carbon atom to which they are attached form an optionally substituted five- or six-membered carbocyclic ring, in which a ring carbon atom is optionally replaced by an oxygen atom, and wherein the ring is optionally substituted once or twice by $C_1$-$C_2$alkyl or $C_1$-$C_2$ alkoxy.

Preferably, G is hydrogen or a group —C($X^a$)—$R^a$ or —($X^b$)—$X^c$—$R^b$, wherein $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $X^a$, $X^b$ and $X^c$ are independently of each other oxygen or sulfur.

More preferably, G is hydrogen.

A compound of formula (I) wherein G is $C_1$-$C_8$ alkyl, $C_2$-$C_8$ haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$ alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, C($X^a$)—$R^a$, C($X^b$)—$X^c$—$R^b$, C($X^d$)—N($R^c$)—$R^d$, —$SO_2$—$R^e$, —P($X^e$)($R^f$)—$R^g$ or $CH_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating a compound of formula (A), which is a compound of formula (I) wherein G is H, with a reagent G-Z, wherein G-Z is alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—$CH_2$—$X^f$— wherein $X^f$ is sulfur), a $C_1$-$C_8$ alkyl sulfonate, or a di-$C_1$-$C_8$-alkyl sulfate, or with a $C_3$-$C_8$ alkenyl halide, or with a $C_3$-$C_8$ alkynyl halide, or with an acylating agent such as a carboxylic acid, HO—C($X^a$)$R^a$, wherein $X^a$ is oxygen, an acid chloride, Cl—C($X^a$)$R^a$, wherein $X^a$ is oxygen, or acid anhydride, [$R^a$C($X^a$)]$_2$O, wherein $X^a$ is oxygen, or an isocyanate, $R^c$N=C=O, or a carbamoyl chloride, Cl—C($X^d$)—N($R^c$)—$R^d$ (wherein $X^d$ is oxygen and with the proviso that neither $R^c$ or $R^d$ is hydrogen), or a thiocarbamoyl chloride Cl—C($X^d$)—N($R^c$)—$R^d$ (wherein $X^d$ is sulfur and with the proviso that neither $R^c$ or $R^d$ is hydrogen) or a chloroformate, Cl—C($X^b$)—$X^c$—$R^b$, (wherein $X^b$ and $X^c$ are oxygen), or a chlorothioformate Cl—C($X^b$)—$X^c$—$R^b$ (wherein $X^b$ is oxygen and $X^c$ is sulfur), or a chlorodithioformate Cl—C($X^b$)—$X^c$—$R^b$, (wherein $X^b$ and $X^c$ are sulfur), or an isothiocyanate, $R^c$N=C=S, or by sequential treatment with carbon disulfide and an alkylating agent, or with a phosphorylating agent such as a phosphoryl chloride, Cl—P($X^e$)($R^f$)—$R^g$ or with a sulfonylating agent such as a sulfonyl chloride Cl—$SO_2$—$R^e$, preferably in the presence of at least one equivalent of base. Those skilled in the art will recognise that when a compound of formula (A) contains an unsymmetrical dione (for example, where X is $CH_2$ and at least one of the substituents $R^5$ and $R^6$ is different to hydrogen), these reactions may produce, in addition to a compound of formula (I), a second compound of formula (IA). This invention covers both a compound of formula (I) and a compound of formula (IA), together with mixtures of these compounds in any ratio.

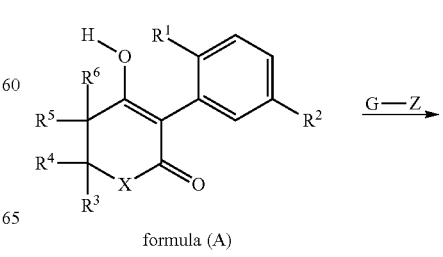

formula (A)

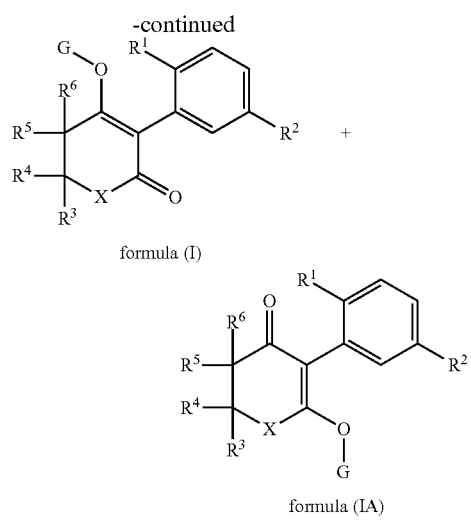

formula (I)

formula (IA)

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425; H. Born et al., J. Chem. Soc., (1953), 1779; M. Constantino et al., Synth. Commun., (1992), 22 (19), 2859; Y. Tian et al., Synth. Commun., (1997), 27 (9), 1577, S. Chandra Roy et al., Chem. Letters, (2006), 35 (1) 16, and P. Zubaidha et al., Tetrahedron Lett., (2004), 45, 7187.

The O-acylation of cyclic 1,3-diones may be effected by procedures similar to those described, for example, by R Haines, U.S. Pat. No. 4,175,135, and by T. Wheeler, U.S. Pat. No. 4,422,870, U.S. Pat. No. 4,659,372 and U.S. Pat. No. 4,436,666. Typically diones of formula (A) may be treated with the acylating agent in the presence of at least one equivalent of a suitable base, optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally a base such as triethylamine or pyridine in a suitable solvent such as tetrahydrofuran, dichloromethane or acetonitrile. Suitable procedures are described, for example, by W. Zhang and G. Pugh, *Tetrahedron Lett.*, (1999), 40 (43), 7595 and T. Isobe and T. Ishikawa, J. Org. Chem., (1999), 64 (19), 6984.

Phosphorylation of cyclic 1,3-diones may be effected using a phosphoryl halide or thiophosphoryl halide and a base by procedures analogous to those described by L. Hodakowski, U.S. Pat. No. 4,409,153.

Sulfonylation of a compound of formula (A) may be achieved using an alkyl or aryl sulfonyl halide, preferably in the presence of at least one equivalent of base, for example by the procedure of C. Kowalski and K. Fields, J. Org. Chem., (1981), 46, 197.

A compound of formula (A) may be prepared by the cyclisation of a compound of formula (B), wherein R is hydrogen or an alkyl group, preferably in the presence of an acid or base, and optionally in the presence of a suitable solvent, by analogous methods to those described by T. Wheeler, U.S. Pat. No. 4,209,532. The compounds of formula (B) have been particularly designed as intermediates in the synthesis of the compounds of the formula (I). A compound of formula (B) wherein R is hydrogen may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

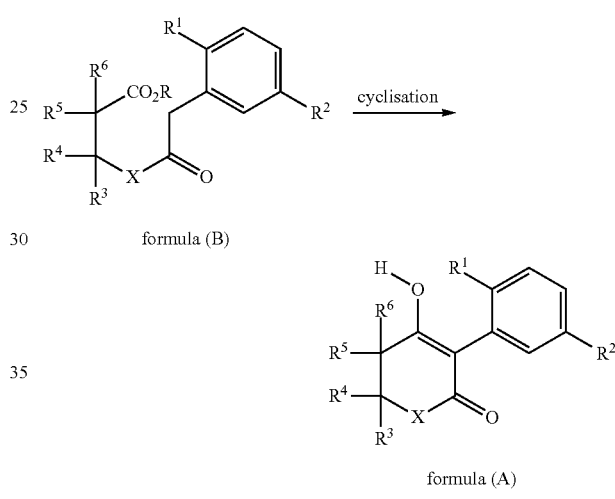

formula (B)

formula (A)

A compound of formula (B) wherein R is alkyl (preferably methyl or ethyl), may be cyclised under acidic or basic conditions, preferably in the presence of at least one equivalent of a strong base such as potassium tert-butoxide, lithium diisopropylamide or sodium hydride and in a solvent such as tetrahydrofuran, dimethylsulfoxide or N,N-dimethylformamide.

A compound of formula (B), wherein X is $CR^7R^8$ and R is H, may be prepared by saponification of a compound of formula (C) wherein R' is alkyl (preferably methyl or ethyl), under standard conditions, followed by acidification of the reaction mixture to effect decarboxylation, by similar processes to those described, for example, by T. Wheeler, U.S. Pat. No. 4,209,532.

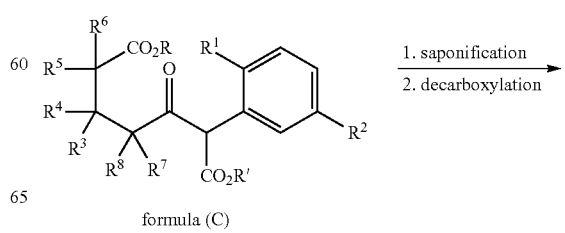

formula (C)

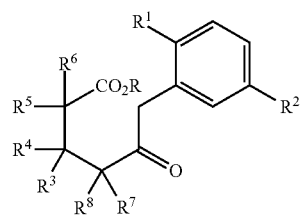

formula (B) wherein
X is CR⁷R⁸

A compound of formula (B), wherein R is H, may be esterified to a compound of formula (B), wherein R is alkyl, under known conditions, for example by heating with an alkyl alcohol, ROH, in the presence of an acid catalyst.

A compound of formula (C), wherein R is alkyl, may be prepared by treating a compound of formula (D) with a suitable carboxylic acid chloride of formula (E) under basic conditions. Suitable bases include potassium tert-butoxide, sodium bis(trimethylsilyl)amide and lithium diisopropylamide and the reaction is preferably conducted in a suitable solvent (such as tetrahydrofuran or toluene) at a temperature of between $-80°$ C. and $30°$ C. Alternatively, a compound of formula (C), wherein R is H, may be prepared by treating a compound of formula (D), wherein R' is $C_1$-$C_4$alkyl, with a suitable base (such as potassium tert-butoxide, sodium bis (trimethylsilyl)amide and lithium diisopropylamide) in a suitable solvent (such as tetrahydrofuran or toluene) at a suitable temperature (between $-80°$ C. and $30°$ C.) and reacting the resulting anion with a suitable anhydride of formula (F):

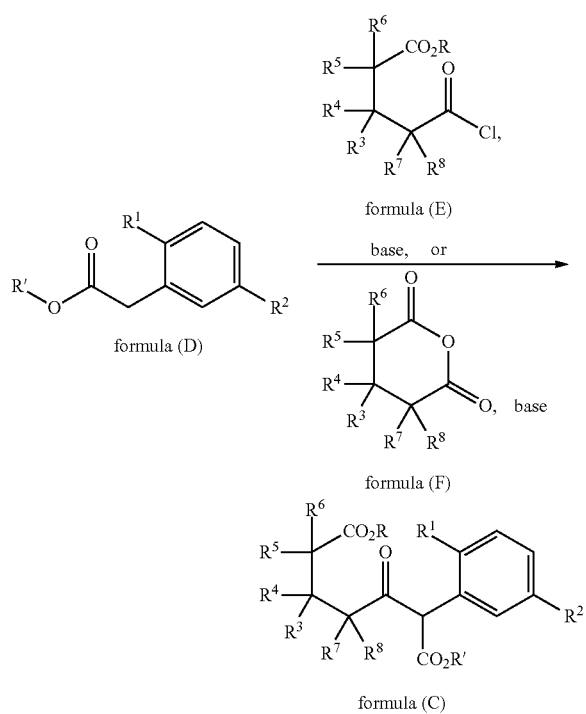

A compound of formula (E) may be prepared from a compound of formula (F) by treatment with an alkyl alcohol, R—OH, in the presence of a base, such as an alkaline metal alkoxide (see, for example, U. Dyer and J. Robinson, J. Chem. Soc. Perkin Trans. 1, (1988), 1, 53; S. Birch et al., J. Chem. Soc., (1952), 1363, S. Buser and A. Vasella, Helv. Chim. Acta, (2005), 88, 3151; M. Hart et al., Bioorg. Med. Chem. Letters, (2004), 14, 1969), followed by treatment of the resulting acid with a chlorinating reagent such as oxalyl chloride or thionyl chloride under known conditions (see, for example, C. Santelli-Rouvier. Tetrahedron Lett., (1984), 25 (39), 4371; D. Walba and M. Wand, Tetrahedron Lett., (1982), 23 (48), 4995; J. Cason, Org. Synth. Coll. Vol. III, (1955), 169).

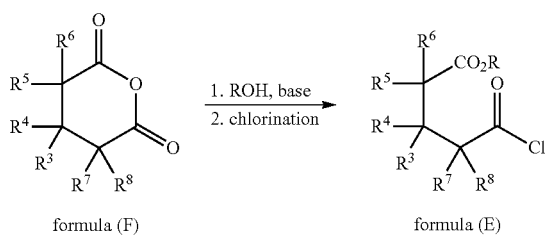

Compounds of formula (F) are known compounds, or may be made from known compounds by known methods (see, for example, J. Baran and H. Mayer, J. Org. Chem., (1988), 53 (19), 4626; Y. Kita et al., J. Org. Chem., (1986), 51 (22), 4150; J. Cason., Org. Synth. Coll. Vol. IV, (1963), 630; S. Birch et al., J. Chem. Soc., (1952), 1363; F. Mezger et al., Synthesis, (1991), 5, 375).

A compound of formula (D) may be prepared from a compound of formula (G) by treatment with an alcohol, R'OH, in the presence of a suitable base. Preferably the alcohol is methanol and the base is sodium methoxide.

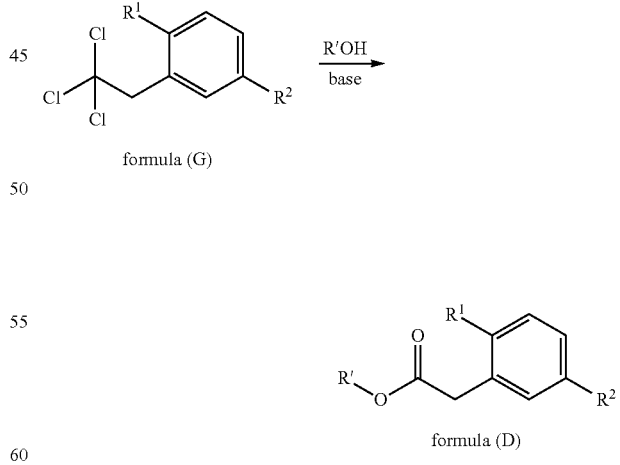

A compound of formula (G) may be prepared by Meerwein arylation of vinylidene chloride by an aniline of formula (H) under known conditions (see, for example C. Rondestvedt, Org. Reaction, (1976), 24, 225; M. Doyle et al., J. Org. Chem., (1977), 42 (14), 2431).

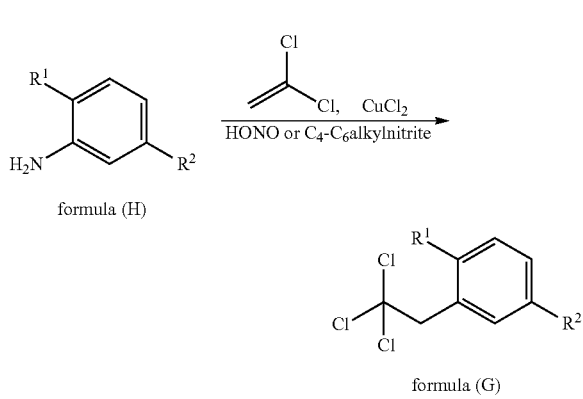

formula (H)

formula (G)

A compound of formula (H) may be prepared by reduction of a compound of formula (J) under known conditions, for example, by catalytic hydrogenation, or by using a metal such as iron or zinc powder in the presence of a suitable acid (such as acetic acid or hydrochloric acid).

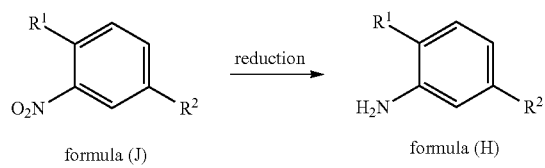

formula (J)    formula (H)

A compound of formula (J) may be prepared from an aryl halide of formula (K), wherein Hal represents a chlorine, bromine or iodine, or is a pseudohalide such as trifluoromethanesulfonyl, by reaction with an aryl- or heteroarylboronic acid of formula $R^2$—$B(OH)_2$, an aryl- or heteroarylboronate ester, $R^3$—$B(OR'')_2$, wherein $R^3$—$B(OR'')_2$ represents a cyclic boronate ester derived from a 1,2- or a 1,3-alkanediol such as pinacol, 2,2-dimethyl-1,3-propanediol and 2-methyl-2,4-pentanediol, or a metal (especially potassium) aryl-, or heteroaryltrifluoroborate salt, $M^+[R^3$—$BF_3]^-$ in the presence of a suitable palladium catalyst, a suitable ligand and a suitable base in the presence of a suitable solvent, under Suzuki-Miyaura conditions (see, for example K. Billingsley and S. Buchwald, J. Am. Chem. Soc., (2007), 129, 3358-3366; H. Stefani, R. Cella and A. Vieira, Tetrahedron, (2007), 63, 3623-3658; N. Kudo, M. Perseghini and G. Fu, Angew. Chem. Int. Ed., (2006), 45, 1282-1284; A. Roglans, A. Pla-Quintana and M. Moreno-Mañas, Chem. Rev., (2006), 106, 4622-4643; J-H Li, Q-M Zhu and Y-X Xie, Tetrahedron (2006), 10888-10895; S. Nolan et al., J. Org. Chem., (2006), 71, 685-692; M. Lysén and K. Köhler, Synthesis, (2006), 4, 692-698; K. Anderson and S. Buchwald, Angew. Chem. Int. Ed., (2005), 44, 6173-6177; Y. Wang and D. Sauer, Org. Lett., (2004), 6 (16), 2793-2796; I. Kondolff, H. Doucet and M, Santelli, Tetrahedron, (2004), 60, 3813-3818; F. Bellina, A. Carpita and R. Rossi, Synthesis (2004), 15, 2419-2440; H. Stefani, G. Molander, C-S Yun, M. Ribagorda and B. Biolatto, J. Org. Chem., (2003), 68, 5534-5539; A. Suzuki, Journal of Organometallic Chemistry, (2002), 653, 83; G. Molander and C-S Yun, Tetrahedron, (2002), 58, 1465-1470; G. Zou, Y. K. Reddy and J. Falck, Tetrahedron Lett., (2001), 42, 4213-7215; S. Darses, G. Michaud and J-P. Genêt, Eur. J. Org. Chem., (1999), 1877-1883; M. Beavers et al., WO2005/012243; J. Org. Chem. (1994), 59, 6095-6097; A. Collier and G. Wagner, Synthetic Communications, (2006), 36; 3713-3721).

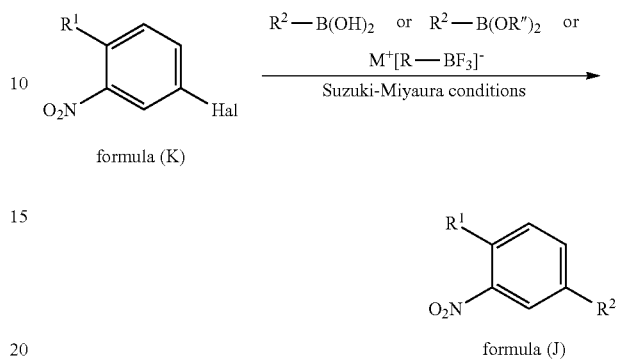

formula (K)

formula (J)

Compounds of formula (K) are known compounds, or may be made by known methods from known compounds (see, for example, R. Lantzsch, WO01/077062; M. Gurjar et al., Synthesis, (2000), 12, 1659; A. Kovendi and M. Kircz, Chem. Ber. (1964), 97 (7), 1896; G. Ecke et al., J. Org. Chem., (1957), 22, 639).

In a further approach to a compound of formula (A), wherein X is $CR^7R^8$, a compound of formula (L), wherein Hal is as defined before, may be reacted with an aryl- or heteroarylboronic acid of formula $R^2$—$B(OH)_2$, an aryl- or heteroarylboronate ester, $R^3$—$B(OR'')_2$, or a metal (especially potassium) aryl-, or heteroaryltrifluoroborate salt, $M^+[R^3$—$BF_3]^-$ in the presence of a suitable palladium catalyst, a suitable ligand and a suitable base in the presence of a suitable solvent, under Suzuki-Miyaura conditions.

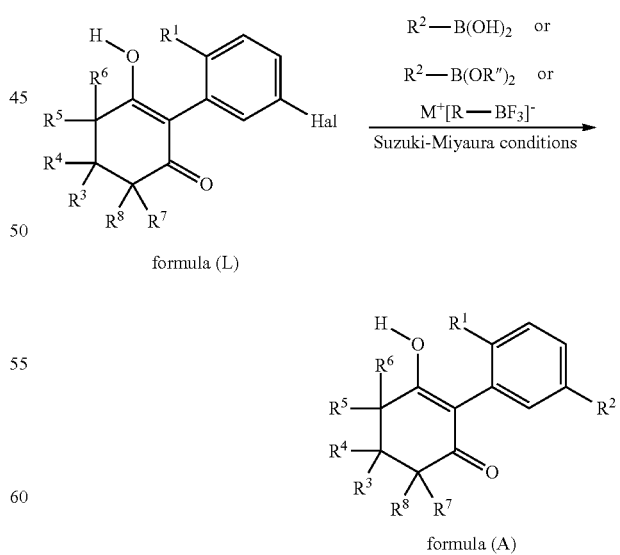

formula (L)

formula (A)

A compound of formula (L) may be prepared from a compound of formula (F) and a compound of formula (K) by similar methods to those described previously.

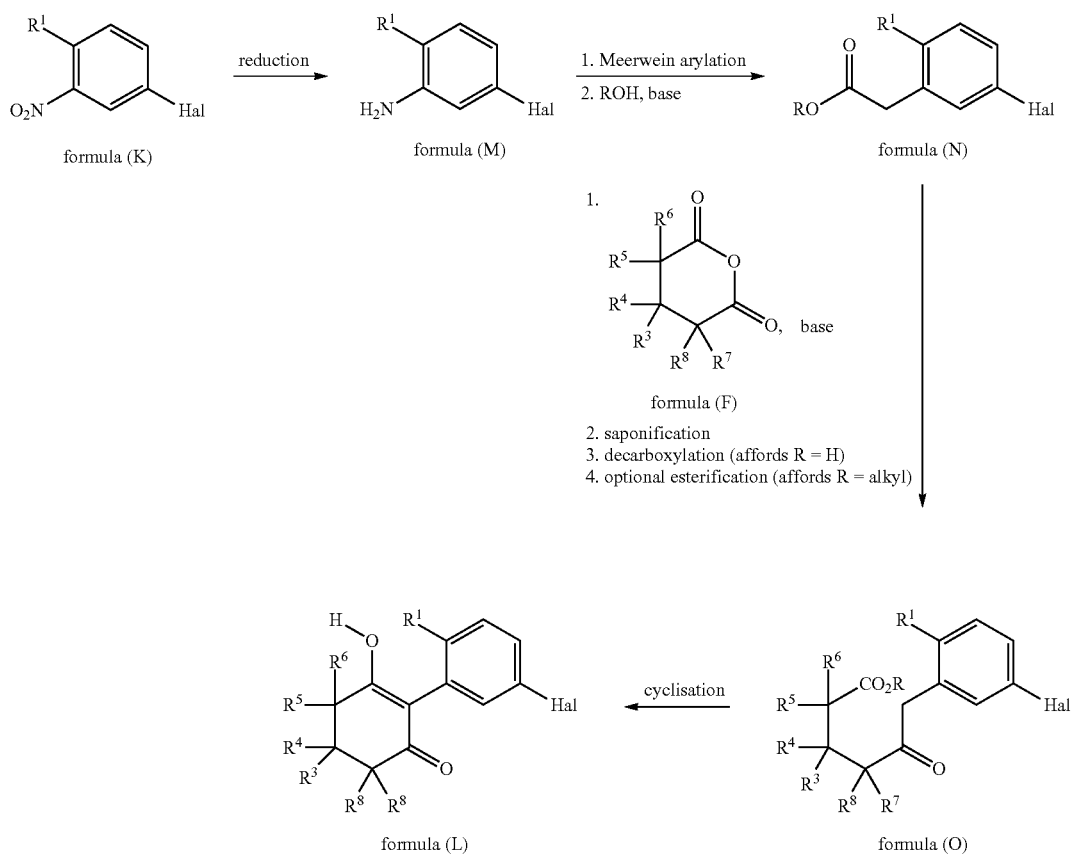

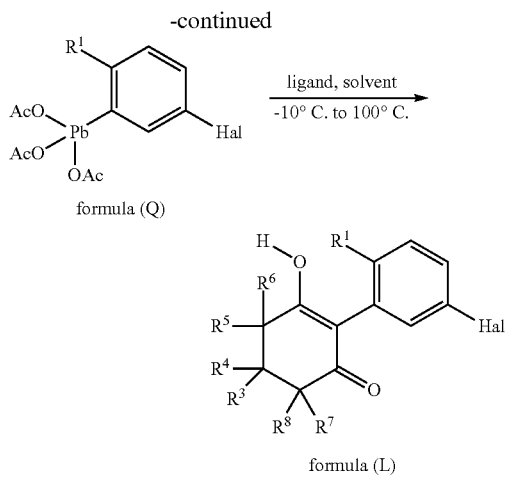

A compound of formula (L), wherein Hal is bromine or chlorine, may alternatively be prepared by reaction of a compound of formula (P) with an aryllead tricarboxylate, in the presence of a suitable ligand and in a suitable solvent. Similar reactions are described in the literature (for example see, J. Pinhey, B. Rowe, Aust. J. Chem., (1979), 32, 1561-; J. Morgan, J. Pinhey, J. Chem. Soc. Perkin Trans. 1, (1990), 3, 715). Preferably the aryllead tricarboxylate is an aryllead triacetate of formula (Q). Preferably the ligand is a nitrogen containing heterocycle such as N,N-dimethylaminopyridine, 1,10-phenanthroline pyridine, bipyridine, or imidazole, and one to ten equivalents of ligand with respect to a compound of formula (P) is preferably used. Most preferably the ligand is N,N-dimethylaminopyridine. The solvent is preferably chloroform, dichloromethane or toluene, most preferably chloroform, or a mixture of chloroform and toluene. Preferably the reaction is conducted at a temperature of –10° C. to 100° C., more preferably at 40-90° C.

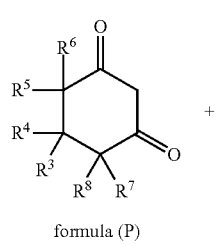

Compounds of formula (P) are known, or can be made by known methods from known compounds.

A compound of formula (Q) may be prepared from a compound of formula (R) by treatment with lead tetraacetate in a suitable solvent (for example chloroform) at 25° C. to 100° C. (preferably 25-50° C.), and optionally in the presence of a catalyst such as mercury diacetate, according to procedures described in the literature (for example see, K. Shimi, G. Boyer, J-P. Finet and J-P. Galy, Letters in Organic Chemistry, (2005), 2, 407; J. Morgan and J. Pinhey, J. Chem. Soc. Perkin Trans. 1; (1990), 3, 715).

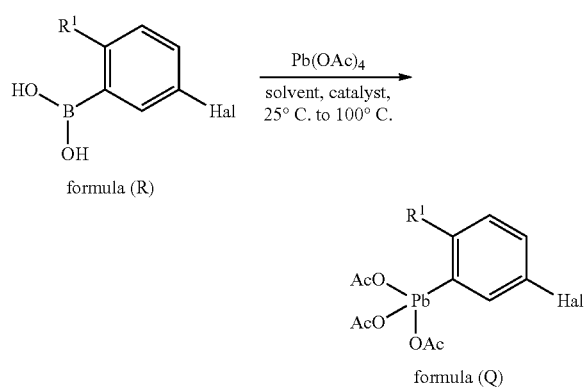

formula (R)

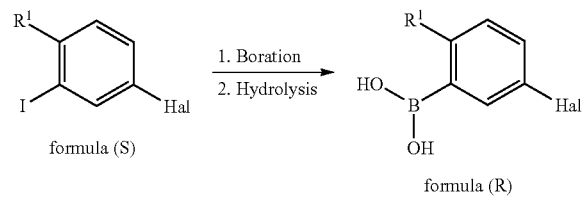

formula (Q)

An aryl boronic acid of formula (R) may be prepared from an aryl iodide of formula (S), by known methods (see, for example, R. Bhatt et al., US2004/0204386). Thus an aryl halide of formula (S) may be treated with an alkaline earth metal (such as magnesium) or a suitable organometallic reagent (such as n-butyllithium or isopropylmagnesium halide) at low temperature, and the resulting aryl magnesium or aryl lithium reagent obtained is allowed to react with a trialkyl borate, preferably trimethylborate, to give an aryl dialkylboronate which may be hydrolysed to the desired boronic acid of formula (R) under acidic conditions.

formula (S) → formula (R)

1. Boration
2. Hydrolysis

Aryl iodides of formula (S) are known compounds or may be made by known methods from known compounds (see, for example, M. Balestra et al., WO06/071730; R. Bhatt et al., US2004/0204386; D. Pauluth and H. Haas, DE4219281).

By procedures analogous to those described above, a compound of formula (I), wherein G is hydrogen, may be prepared from a compound of formula (P) and an aryllead triacetate of formula ($Q_1$) in the presence of a nitrogen-containing ligand and a solvent.

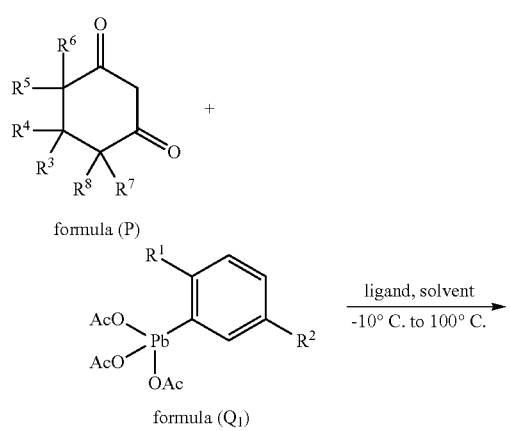

formula (P) + formula ($Q_1$)

ligand, solvent
-10° C. to 100° C.

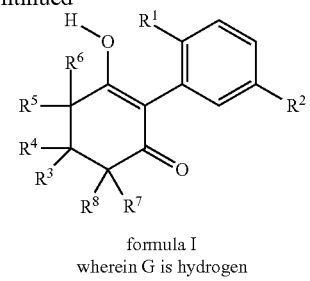

formula I
wherein G is hydrogen

Compounds of formula ($Q_1$) are known compounds, or may be prepared according to known procedures, for example as described by M. Muehlebach et al. WO08/071,405.

A compound of formula (A), wherein X, is O, may be prepared from a compound of formula (B), wherein X is O, by cyclisation under acidic or basic conditions, as described previously.

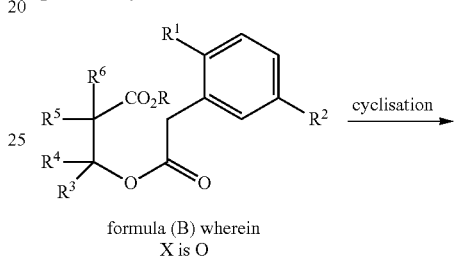

formula (B) wherein X is O cyclisation →

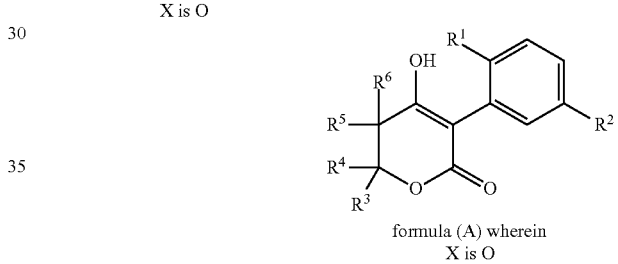

formula (A) wherein X is O

A compound of formula (B), wherein X is O, may be prepared from a compound of formula (T) by reaction with a compound of formula (U), optionally in the presence of a suitable base (such as triethylamine or pyridine) and in a suitable solvent (such as toluene, tetrahydrofuran, 1,4-dioxane, dichloromethane or chloroform).

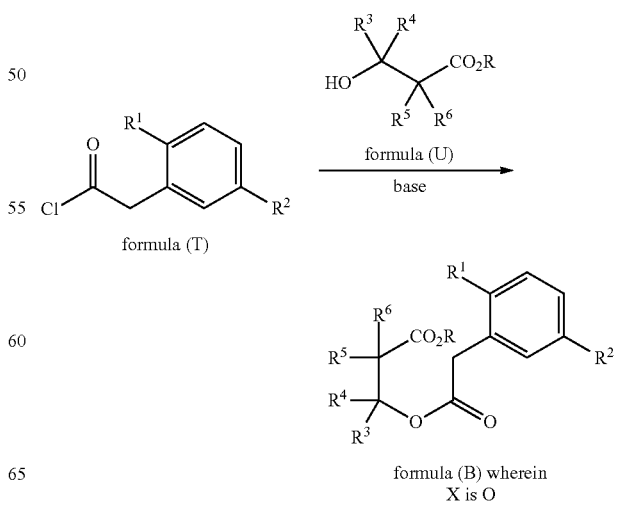

formula (T) + formula (U) → formula (B) wherein X is O base

A compound of formula (T) may be prepared from a compound of formula (D) by known methods. Thus a compound of formula (D), may be hydrolysed, and the resulting carboxylic acid treated with a chlorinating agent (such as thionyl chloride, or oxalyl chloride) under known conditions to give a compound of formula (T).

Compounds of formula (U) are known compounds, or may be made by known methods from known compounds (see, for example, F. Gaudemar-Bardonne and M. Gaudemar, Synthesis, (1979), 463; H. Schick et al., J. Org. Chem., (1994), 59, 3161).

In a similar manner, a compound of formula (A), wherein X is $NR^9$, may be prepared from a compound of formula B, wherein X is $NR^9$, by cyclisation under acidic or basic conditions.

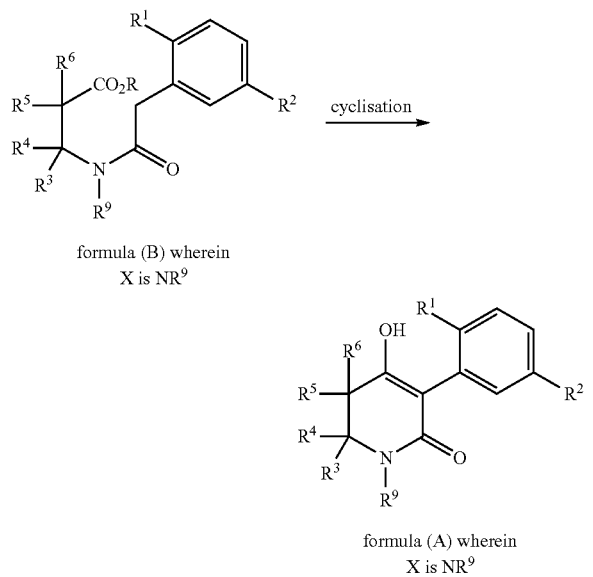

A compound of formula (B), wherein X is $NR^9$, may be prepared from a compound of formula (T) by reaction with a compound of formula (V), optionally in the presence of a suitable base (such as triethylamine or pyridine) and in a suitable solvent (such as toluene, tetrahydrofuran, 1,4-dioxane, dichloromethane or chloroform).

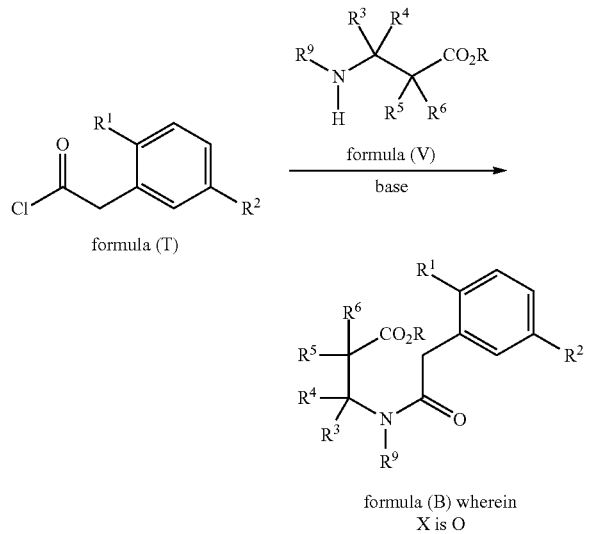

Compounds of formula (V) are known compounds, or may be prepared by known methods from known compounds (see, for example, S. Thaisrivongs et al., J. Med. Chem., (1991), 34, 633; J. Maibaum et al., J. Med. Chem., (2007), 50, 4832; A. Lebedev et al., Russ. J. Gen. Chem., (2006), 76 (7), 1069).

A compound of formula (A), wherein X is S, may be prepared from a compound of formula (W), wherein R''' is a suitable protecting group for sulfur, by deprotection and ring-closure.

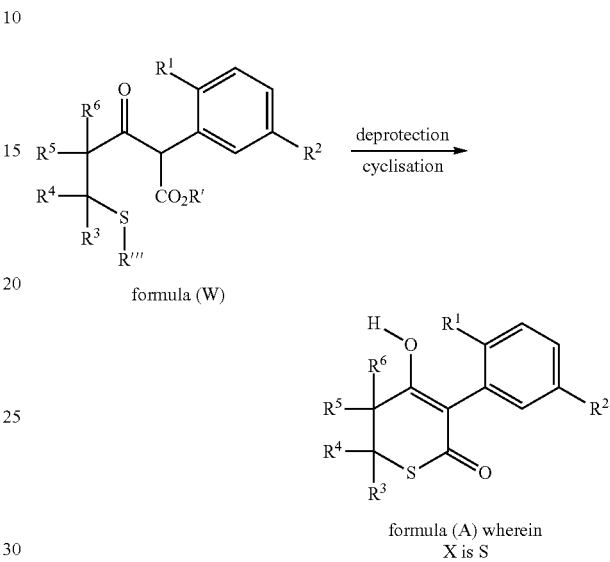

Preferably the protecting group R''' is an optionally substituted benzyl group (especially para-methoxybenzyl), and cleavage and cyclisation may be achieved in the presence of a suitable acid (such as trifluoroacetic acid or trifluoromethanesulfonic acid) and in the presence of a suitable solvent (such as toluene).

A compound of formula (W) may be prepared by treating a compound of formula (D) with a compound of formula (X) under basic conditions. Suitable bases include potassium tert-butoxide, sodium bis(trimethylsilyl)amide and lithium diisopropylamide and the reaction is preferably conducted in a suitable solvent (such as tetrahydrofuran or toluene) at a temperature of between –80° C. and 30° C.

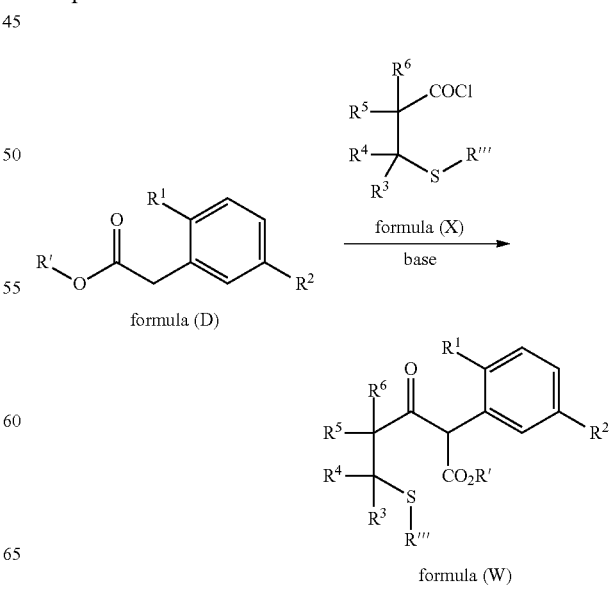

A compound of formula (X) may be prepared from a compound of formula (Y) by treatment with a chlorinating agent (such as thionyl chloride, or oxalyl chloride) under known conditions.

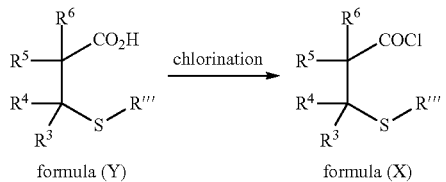

Compounds of formula (Y) are known compounds, or may be made by known methods from known compounds (see, for example, R. Brown et al., J. Chem. Soc., (1951), 3315; J. Nestor et al., (1975), 18, 284).

A compound of formula (A) wherein $R^3$ and $R^6$ form a bond and X is oxygen may be prepared by the reaction of a compound of formula (Z) with a compound of formula (AA), or with a compound of formula (AB), and in a suitable solvent (such as toluene) according to procedures described, for example, by F. Lieb et al., Tetrahedron, (2001), 57, 4133; F. Lieb et al., WO00/21946.

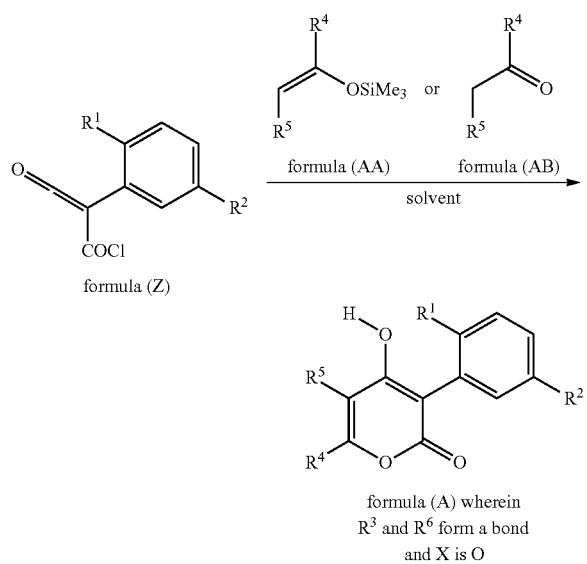

formula (A) wherein $R^3$ and $R^6$ form a bond and X is O

A compound of formula (Z) may be prepared by from a compound of formula (AC) by treatment with thionyl chloride, oxalyl chloride, phosphorus(V) chloride, phosgene or similar reagent, optionally in a suitable solvent (such as toluene or dichloromethane) and optionally in the presence of a base (such as triethylamine or pyridine) and an additive (such as dimethylformamide).

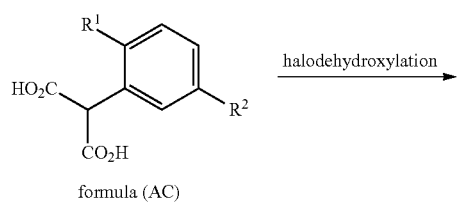

formula (AC)

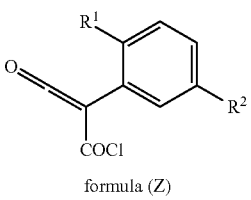

formula (Z)

A compound of formula (AC) may be prepared from a compound of formula (AD), wherein R'''' is $C_1$-$C_4$ alkyl (preferably $C_1$-$C_2$alkyl) by hydrolysis under acidic or basic conditions.

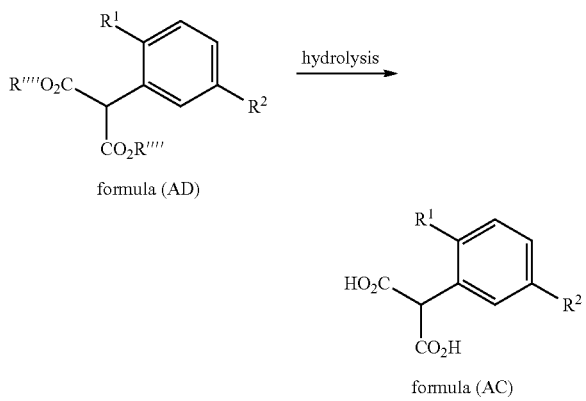

A compound of formula (AD) may be prepared from a compound of formula (AE), wherein Hal is bromine or iodine, and a dialkylmalonate of formula $CH_2(CO_2R'''')_2$ under palladium-catalysed conditions as described, for example, by J. Fox et al., J. Am. Chem. Soc., (2000), 122, 1360 and I. Özdemir et al., Tetrahedron Lett., (2004), 45, 5823.

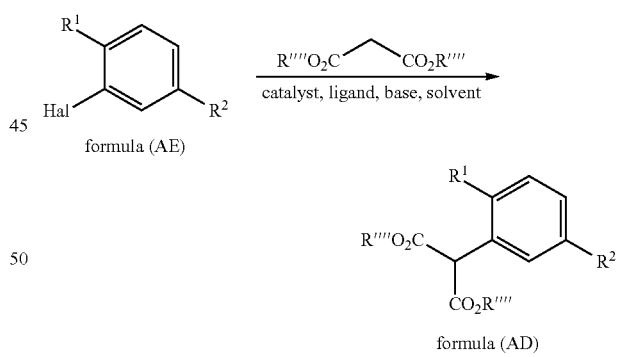

An aryl halide of formula (AE) may be prepared from an aniline of formula (AF) by known methods, for example the Sandmeyer reaction, via the corresponding diazonium salts.

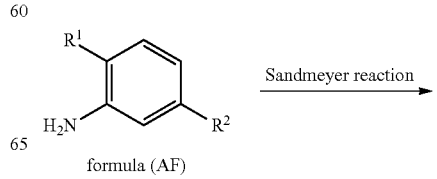

-continued

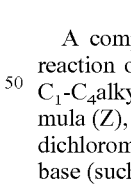

formula (AE)

An aniline of formula (AF) may be made by the cross-coupling of an aryl halide of formula (AG), wherein Hal is chlorine, bromine or iodine or a pseudohalide such as a trifluoromethanesulfonyl moiety, with a suitable coupling partners such as an aryl- or heteroarylboronic acid, $R^2$—$B(OH)_2$, an aryl- or heteroarylboronate ester, $R^2$—$B(OMe)_2$ or $R^2$—$B(OR'')_2$, or a metal (especially potassium) aryl-, or heteroaryltrifluoroborate salt, $M^+[R^2$—$BF_3]^-$ in the presence of a suitable palladium catalyst, a suitable ligand and a suitable base in the presence of a suitable solvent, under Suzuki-Miyaura conditions (see, for example, J.-H. Li, Q.-M. Zhu and Y.-X. Xie, Tetrahedron, (2006), 62, 10888; K. Anderson and S. Buchwald, Angew. Chem. Int. Ed. (2005), 44, 6173; M. Lysén and K. Köhler, Synthesis, (2006), 4, 692; N. Kudo, M. Perseghini and G. Fu, Angew. Chem. Int. Ed., (2006), 45, 1282; J. Yan, W. Hu and W. Zhou, Synth. Commun. (2006), 36, 2102; R. Arvela and N. Leadbeater, Org. Lett., (2005), 7 (11) 2101; T. Barder and S. Buchwald, Org. Lett., (2004), 6 (16), 2649; F. Bellina, A. Carpita and R. Rossi, Synthesis (2004), 15, 2419 and A. Suzuki, Journal of Organometallic Chemistry, (2002), 653, 83).

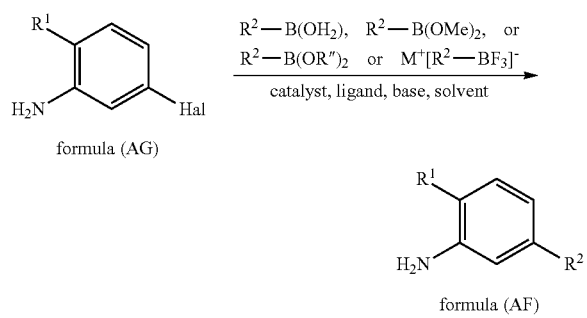

formula (AG)

formula (AF)

A compound of formula (AG) may be prepared from a nitrobenzene of formula (AH) by reduction by known methods (for example by treatment with a reducing agent such as iron or zinc in the presence of an acid, or by catalytic hydrogenation).

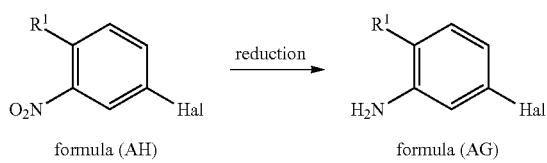

formula (AH)  formula (AG)

Alternatively, a compound of formula (AH) may be cross-coupled with a suitable aryl- or heteroarylboronic acid, $R^2$—$B(OH)_2$, an aryl- or heteroarylboronate ester, $R^2$—$B(OMe)_2$ or $R^2$—$B(OR'')_2$, or a metal (especially potassium) aryl-, or heteroaryltrifluoroborate salt, $M^+[R^2$—$BF_3]^-$ under Suzuki-Miyaura conditions, and the resulting nitrobenzene of formula (AI) reduced under known conditions to give a compound of formula (AF).

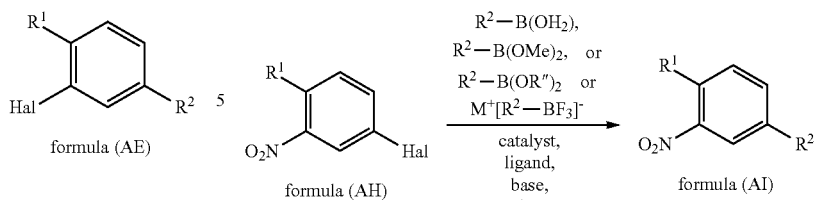

formula (AH)  formula (AI)

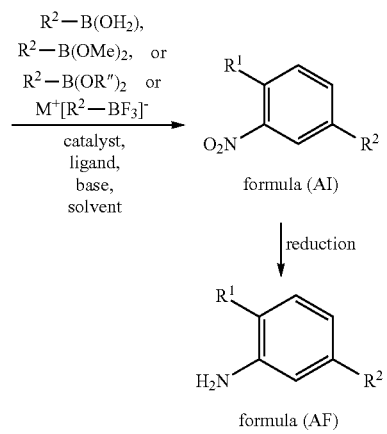

formula (AF)

Compounds of formula (AA), of formula (AB) and of formula (AH) are known, or may be made by known methods from known compounds.

A compound of formula (A), wherein $R^3$ and $R^4$ form a bond, $R^5$ is hydrogen and X is S may be prepared by the saponification and decarboxylation of a compound of formula (AJ), wherein R''' is preferably $C_1$-$C_4$ alkyl according to known procedures (see, for example, F. Splinter and H. Arold, J. Prakt. Chem., (1968), 38 (3-4), 142).

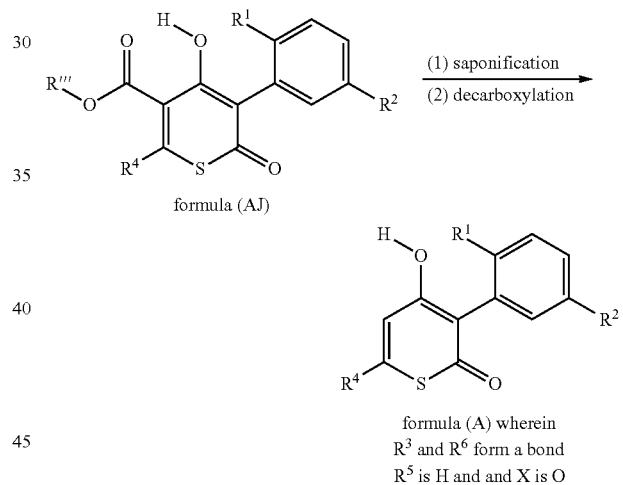

formula (AJ)

formula (A) wherein
$R^3$ and $R^6$ form a bond
$R^5$ is H and and X is O

A compound of formula (AJ) may be prepared by the reaction of a compound of formula (AK), wherein R'''' is $C_1$-$C_4$alkyl (preferably $C_1$-$C_2$alkyl), and a compound of formula (Z), optionally in a suitable solvent (such as toluene or dichloromethane) and optionally in the presence of a suitable base (such as triethylamine or pyridine.

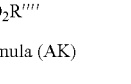

formula (AK)  formula (Z)

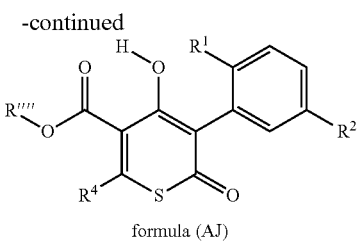

formula (AJ)

Compounds of formula (AK) are known compounds or may be made by known methods from known compounds.

The compounds of formula I according to the invention can be used as herbicides in unmodified form, as obtained in the synthesis, but they are generally formulated into herbicidal compositions in a variety of ways using formulation adjuvants, such as carriers, solvents and surface-active substances. The formulations can be in various physical forms, for example in the form of dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. Such formulations can either be used directly or are diluted prior to use. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be formulated with other adjuvants, for example finely divided solids, mineral oils, vegetable oils, modified vegetable oils, organic solvents, water, surface-active substances or combinations thereof. The active ingredients can also be contained in very fine microcapsules consisting of a polymer. Microcapsules contain the active ingredients in a porous carrier. This enables the active ingredients to be released into their surroundings in controlled amounts (e.g. slow release). Microcapsules usually have a diameter of from 0.1 to 500 microns. They contain active ingredients in an amount of about from 25 to 95% by weight of the capsule weight. The active ingredients can be present in the form of a monolithic solid, in the form of fine particles in solid or liquid dispersion or in the form of a suitable solution. The encapsulating membranes comprise, for example, natural and synthetic gums, cellulose, styrene-butadiene copolymers, polyacrylonitrile, polyacrylate, polyester, polyamides, polyureas, polyurethane or chemically modified polymers and starch xanthates or other polymers that are known to the person skilled in the art in this connection. Alternatively it is possible for very fine microcapsules to be formed wherein the active ingredient is present in the form of finely divided particles in a solid matrix of a base substance, but in that case the microcapsule is not encapsulated.

The formulation adjuvants suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylenes carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and higher molecular weight alcohols, such as amyl alcohol, tetrahydrofurfuryl alcohol, hexanol, octanol, ethylene glycol, propylene glycol, glycerol, N-methyl-2-pyrrolidone and the like. Water is generally the carrier of choice for the dilution of the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheatmeal, soybean flour, pumice, wood flour, ground walnut shells, lignin and similar materials, as described, for example, in CFR 180.1001. (c) & (d).

A large number of surface-active substances can advantageously be used both in solid and in liquid formulations, especially in those formulations which can be diluted with a carrier prior to use. Surface-active substances may be anionic, cationic, non-ionic or polymeric and they may be used as emulsifying, wetting or suspending agents or for other purposes. Typical surface-active substances include, for example, salts of alkyl sulfates, such as diethanolammonium lauryl sulfate; salts of alkylarylsulfonates, such as calcium dodecyl benzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, and also liquid and solid fertilisers.

The formulations may also comprise additional active substances, for example further herbicides, herbicide safeners, plant growth regulators, fungicides or insecticides.

The compositions according to the invention can additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). Further oil additives that are preferred according to the invention are SCORE® (Syngenta Crop Protection Canada) and Adigor® (Syngenta Crop Protection Canada).

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pene-trate®, can also be mixed into the spray mixture as activity-enhancing agents.

The herbicidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1-2000 g/ha, preferably 1-1000 g/ha and most preferably at 1-500 g/ha.

Preferred formulations have especially the following compositions: (%=percent by weight):

| Emulsifiable concentrates: | |
|---|---|
| active ingredient: | 1 to 95%, preferably 60 to 90% |
| surface-active agent: | 1 to 30%, preferably 5 to 20% |
| liquid carrier: | 1 to 80%, preferably 1 to 35% |
| Dusts: | |
| active ingredient: | 0.1 to 10%, preferably 0.1 to 5% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.1 to 30%, preferably 0.1 to 15% |
| solid carrier: | 99.5 to 70%, preferably 97 to 85% |

The following Examples further illustrate, but do not limit, the invention.

| F1. Emulsifiable concentrates | | | | |
|---|---|---|---|---|
| | a) | b) | c) | d) |
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |

F1. Emulsifiable concentrates

|  | a) | b) | c) | d) |
|---|---|---|---|---|
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be prepared from such concentrates by dilution with water.

F2. Solutions

|  | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for application in the form of microdrops.

F3. Wettable powders

|  | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

F4. Coated granules

|  | a) | b) | c) |
|---|---|---|---|
| active ingredient | 0.1% | 5% | 15% |
| highly dispersed silicic acid | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated under reduced pressure.

F5. Coated granules

|  | a) | b) | c) |
|---|---|---|---|
| active ingredient | 0.1% | 5% | 15% |
| polyethylene glycol MW 200 | 1.0% | 2% | 3% |
| highly disperse silicic acid | 0.9% | 1% | 2% |
| inorg. carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

F6. Extruder granules

|  | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

F7. Dusts

|  | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

F8. Suspension concentrates

|  | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, yielding a suspension concentrate from which suspensions of any desired concentration can be prepared by dilution with water.

The invention relates also to a method for the selective control of grasses and weeds in crops of useful plants, and for non-selective weed control, which comprises treating the useful plants or the area under cultivation or the locus thereof with a compound of formula I.

Crops of useful plants in which the compositions according to the invention can be used include especially cereals, in particular wheat and barley, rice, corn, rape, sugarbeet, sugarcane, soybean, cotton, sunflower, peanut and plantation crops.

The term "crops" is to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*. Control of monocotyledonous weeds, in particular *Agrostis, Avena, Setaria, Lolium, Echinochloa, Bromus, Alopecurus* and *Sorghum* is very extensive.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with other herbicides. The following mixtures of the compound of formula I are especially important. Preferably, in these mixtures, the compound of the formula I is one of those compounds listed in Tables 1 to 26 below:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atrazine, formula I+aviglycine, formula I+azafenidin, compound of formula I+azimsulfuron, compound of formula I+BCPC, compound of formula I+beflubutamid, compound of formula I+benazolin, formula I+bencarbazone, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, formula I+bromophenoxim, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, formula I+desmetryn, compound of formula I+dicamba, compound of formula I+dichlobenil, compound of formula I+ortho-dichlorobenzene, compound of formula I+paradichlorobenzene, compound of formula I+dichloroprop, compound of formula I+dichloroprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, formula I+dipopetryn, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, formula I+ethephon, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, formula I+fluazolate, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, formula I+flumetralin, compound of formula I+flumetsulam, compound of formula I+flumiclorac, compound of formula I+flumiclorac-pentyl, compound of formula I+flumioxazin, formula I+flumipropin, compound of formula I+fluometuron, compound of formula I+fluoroglycofen, compound of formula I+fluoroglycofen-ethyl, formula I+fluoxaprop, formula I+flupoxam, formula I+flupropacil, compound of formula I+flupropanate, compound of formula I+flupyrsulfuron, compound of formula I+flupyrsulfuron-methyl-sodium, compound of formula I+fluorenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, formula I+isoxapyrifop, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, formula I+methazole, compound of formula I+methylarsonic acid, compound of formula I+methyldymron, compound of formula I+methyl isothiocyanate, compound of formula I+metobenzuron, formula I+methobromuron, compound of formula I+metolachor, compound of formula I+S-metolachor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, formula I+NDA-402989, compound of formula I+neburon, compound of formula I+nicosulfuron, formula I+nipyraclofen, formula I+n-methyl glyphosate, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, formula I+prohexadione-calcium, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, formula I+pyrasulfotole, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, formula I+pyroxasulfone (KIN-485), formula I+pyroxulam, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, formula I+tebutam, compound of formula I+tebuthiuron, formula I+tefuryltrione, compound of formula 1+tembotrione, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazafluoron, compound of formula I+thiazopyr, compound of formula I+thifensulfuron, compound of formula I+thiencarbazone, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+trinexapac-ethyl, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-hydroxy-3-[[2-[(2-methoxyethoxy)methyl]-6-(trifluoromethyl)-3-pyridinyl]carbonyl]-bicyclo [3.2.1]oct-3-en-2-one (CAS RN 352010-68-5), and compound of formula I+4-hydroxy-3-[[2-(3-methoxypropyl)-6-(difluoromethyl)-3-pyridinyl]carbonyl]bicyclo[3.2.1] oct-3-en-2-one.

The mixing partners for the compound of formula I may also be in the form of esters or salts, as mentioned e.g. in The Pesticide Manual, 12th Edition (BCPC) 2000.

The compounds of formula (I) according to the invention can also be used in combination with safeners. Preferably, in these mixtures, the compound of the formula (I) is one of those compounds listed in Tables 1 to 26 below. The following mixtures with safeners, especially, come into consideration:
compound of formula I+cloquintocet-mexyl, compound of formula I+cloquintocet acid and salts thereof, compound of formula I+fenchlorazole-ethyl, compound of formula I+fenchlorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292. A safening effect can also be observed for the mixtures compound of the formula I+dymron, compound of the formula I+MCPA, compound of the formula I+mecopropand compound of the formula I+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484.

The rate of application of safener relative to the herbicide is largely dependent upon the mode of application. In the case of field treatment, generally from 0.001 to 5.0 kg of safener/ha, preferably from 0.001 to 0.5 kg of safener/ha, and generally from 0.001 to 2 kg of herbicide/ha, but preferably from 0.005 to 1 kg/ha, are applied.

The herbicidal compositions according to the invention are suitable for all methods of application customary in agriculture, such as, for example, pre-emergence application, post-emergence application and seed dressing. Depending upon the intended use, the safeners can be used for pretreating the seed material of the crop plant (dressing the seed or seedlings) or introduced into the soil before or after sowing, followed by the application of the (unsafened) compound of the formula I, optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field treatment, generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10000 ppm, preferably from 100 to 1000 ppm.

The following Examples illustrate the invention further but do not limit the invention.

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds shown below, and in Table T1 are drawn as an arbitrary single enol tautomer, but it should be inferred that this description covers both the diketone form and any possible enols which could arise through tautomerism. Within the detailed experimental section the diketone tautomer is chosen for naming purposes, even if the predominant tautomer is the enol form.

PREPARATION EXAMPLES

Example 1

Preparation of 2-(4'-chloro-4-ethylbiphen-3-yl)-4,4-dimethyl-1,3-cyclohexanedione

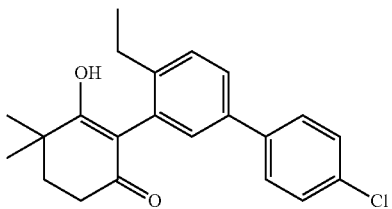 [SMILES: CCc1ccc(-c2ccc(Cl)cc2)cc1C1=C(O)C(C)(C)CCC1=O]

Step 1: Preparation of 4-ethyl-3-nitroaniline

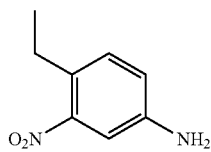

Ammonium nitrate (39.6 g, 0.49 mol) is added portionwise to a chilled (ice-bath) solution of 4-ethylaniline (20 g, 0.16 mol) in concentrated sulfuric acid (100 ml), maintaining the temperature at −10° C. to 0° C. by external cooling. The reaction mixture is stirred for two hours, then poured onto crushed ice, and the precipitate is collected by filtration. The solid is taken up in water, the solution made neutral by addition of dilute aqueous sodium hydroxide solution and extracted with ethyl acetate. The organic extracts are combined, dried over anhydrous sodium sulfate, filtered and the filtrate is evaporated in vacuo to give 4-ethyl-3-nitroaniline (20 g).

Step 2: Preparation of 4-bromo-1-ethyl-2-nitrobenzene

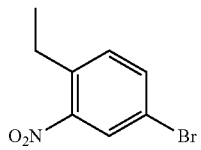

Hydrobromic acid (48% wt. in water, 240 ml) is added dropwise to a suspension of 4-ethyl-3-nitroaniline (20 g, 0.12 mol) in water (80 ml), and the mixture is stirred until the solid dissolves. The mixture is cooled to −5° C. and a solution of sodium nitrite (19.8 g, 0.28 mol) in water (100 ml) is added dropwise, maintaining the temperature at 0-5° C. Once the addition is complete, the cooling bath is removed and the reaction mixture is stirred for one hour at room temperature. The mixture is added dropwise to a pre-cooled solution of cuprous bromide (22.4 g, 0.16 mol) in hydrobromic acid (48% wt. in water) at 0° C. The reaction mixture is stirred and allowed to warm to room temperature over three hours. The mixture is extracted with diethyl ether, and the organic extracts are combined, dried over anhydrous sodium sulfate, filtered and the filtrate is concentrated in vacuo. The residue is further purified by column chromatography on silica gel, eluting with hexane to give 4-bromo-1-ethyl-2-nitrobenzene (18 g)

Step 3: Preparation of 4'-chloro-4-ethyl-3-nitrobiphenyl

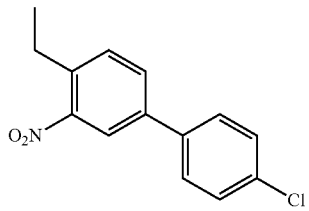 [SMILES: CCc1ccc(-c2ccc(Cl)cc2)cc1[N+](=O)[O-]]

To 4-bromo-1-ethyl-2-nitrobenzene (20.0 g, 0.087 mol) in 150 ml 1,2-dimethoxyethane is added, at room temperature, 4-chlorophenylboronic acid (14.98 g, 0.096 mol) and tetrakis(triphenylphosphine)palladium(0) (2.0 g, 0.00174 mol) and nitrogen gas is bubbled through the mixture. After stirring for 10 minutes at 20° C., a solution of sodium carbonate (73.8 g, 0.696 mol) in water (350 ml) is added and mixture is refluxed for 16 hours. The reaction mixture is cooled to room temperature, filtered through diatomaceous earth, washing with 200 ml of ethyl acetate. The mixture is poured into a separating funnel and the two phases are separated. The aqueous phase is extracted with ethyl acetate. The organic extracts are combined, dried over anhydrous magnesium sulfate, filtered and the filtrate is evaporated in vacuo to give 4'-chloro-4-ethyl-3-nitrobiphenyl (23.84 g) as a brown oil used without further purification in the next step.

Step 4: Preparation of 3-amino-4'-chloro-4-ethylbiphenyl

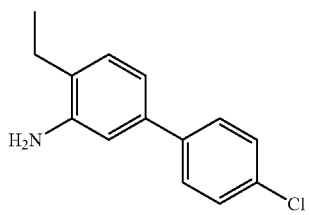

4'-Chloro-4-ethyl-3-nitrobiphenyl (22.6 g, 0.086 mol) is suspended in methanol (250 ml) and the reaction mixture is stirred at room temperature. Distilled water (100 ml) is added, followed by zinc dust (39.0 g, 0.60 mol) and ammonium chloride (13.8 g, 0.26 mol) and the mixture is heated to reflux for 1 hour. The reaction mixture is cooled to room temperature, filtered through diatomaceous earth and the filtrate is evaporated in vacuo to remove most of the methanol. The residue is partitioned between ethyl acetate (200 ml) and water and the aqueous phase is re-extracted with ethyl acetate (200 ml). The organic extracts are combined, washed with water and brine, dried over anhydrous magnesium sulfate, filtered and the filtrate is evaporated in vacuo to give 3-amino-4'-chloro-4-ethylbiphenyl (15.0 g) as a colourless solid. The product is used directly without further purification in Step 5.

Step 5: Preparation of 3-bromo-4'-chloro-4-ethylbiphenyl

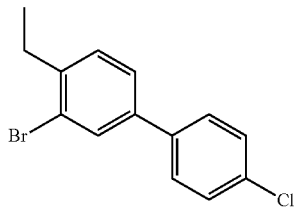 [SMILES: CCc1ccc(-c2ccc(Cl)cc2)cc1Br]

Step 5a:
3-Amino-4'-chloro-4-ethylbiphenyl (60.0 g, 0.26 mol) is added portionwise to a mixture of hydrobromic acid (48% wt. in water, 350 ml) and water (250 ml), and once the addition is complete the mixture is heated to 40° C. and stirred for 20 minutes, before being cooled to 5° C. in an ice bath. A solution of sodium nitrite (20.65 g, 0.30 mol) in water (100 ml) is added dropwise over 45 minutes, and once the addition is complete the mixture is stirred at 5° C. for a further 45 minutes.
Step 5b:
Meanwhile, hydrobromic acid (48% wt. in water, 400 ml) is heated and stirred at 70° C. and copper sulfate pentahydrate (74.75 g, 0.30 mol) is added in one portion and the mixture is stirred at 70° C. for two minutes to give a dark purple solution, and then copper powder (26.44 g, 0.42 mol) is added in one portion, resulting in a pink suspension.
Step 5c
The mixture containing the diazonium salt (prepared in step 5a) is added portionwise over 70 minutes to the stirred mixture prepared in Step 5b at 70° C. (in between additions the mixture containing the diazonium salt is kept cold in an ice bath). Once the addition is complete the mixture is stirred at 70° C. for a further 30 minutes and then allowed to cool to room temperature, and extracted with ethyl acetate (3×500 ml). The organic extracts are combined, washed with water and brine, dried over anhydrous magnesium sulfate, filtered and the filtrate is evaporated in vacuo. Purification by column chromatography on silica gel affords 3-bromo-4'-chloro-4-ethylbiphenyl (52.1 g) as a yellow oil Step 6: Preparation of 4'-chloro-4-ethylbiphen-3-ylboronic acid

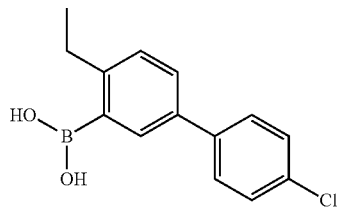 [SMILES: CCc1ccc(-c2ccc(Cl)cc2)cc1B(O)O]

3-Bromo-4'-chloro-4-ethylbiphenyl (10 g, 0.03 mol) is dissolved in tetrahydrofuran (250 ml), and the temperature is cooled to −78° C. n-Butyllithium (1.33 molar solution in hexanes, 34.6 ml) is added dropwise over 30 minutes, maintaining the temperature at around −78° C. The reaction mixture is stirred for one and a half hours, then trimethylborate (4.9 g, 0.05 mol) is added dropwise and the reaction mixture is stirred for two hours. A solution of 2N aqueous hydrochloric acid (100 ml) is added dropwise, and once the addition is complete the mixture is stirred for two hours. The mixture is concentrated to remove most of the tetrahydrofuran, then diluted with water and extracted with diethyl ether. The organic extracts are washed with water and brine, combined, dried over anhydrous sodium sulfate, filtered and the filtrate is evaporated in vacuo. The residue is further purified by flash column chromatography on silica gel, eluting with 7% ethyl acetate in hexane to give 4'-chloro-4-ethylbiphen-3-ylboronic acid (5.4 g).

Step 7: Preparation of 4'-chloro-4-ethylbiphen-3-yllead triacetate

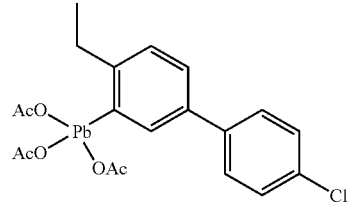

Step 7a:
To a mixture of lead tetraacetate (2.15 g, 4.85 mmol) and mercuric diacetate (0.15 g, 0.47 mmol), thoroughly flushed with nitrogen, is added anhydrous chloroform (6 ml). This mixture is warmed to 40° C., and 4'-chloro-4-ethylbiphen-3-ylboronic acid (1.17 g, 4.50 mmol) is added in one portion and the suspension is heated at this temperature for 5 hours. The mixture is then cooled to room temperature, concentrated to a small volume and triturated with hexanes and filtered to yield crude 4'-chloro-4-ethylbiphen-3-yllead triacetate (2.70 g).
Step 7b:
Crude 4'-chloro-4-ethylbiphen-3-yllead triacetate (1.50 g) is dissolved in anhydrous chloroform (20 ml), to which is added powdered anhydrous potassium carbonate (0.58 g, 4.16 mmol) followed by rapid stirring for 5 minutes. Solids are removed by filtration, and the organic solution is concentrated to afford pure 4'-chloro-4-ethylbiphen-3-yllead triacetate (1.176 g) as a bright orange solid.

Step 8

Preparation of 2-(4'-chloro-4-ethylbiphen-3-yl)-4,4-dimethyl-1,3-cyclohexanedione

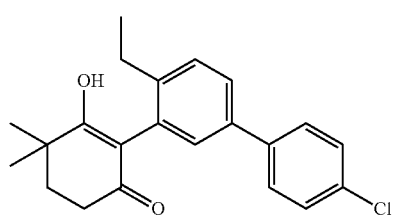 [SMILES: CCc1ccc(-c2ccc(Cl)cc2)cc1C1=C(O)C(C)(C)CCC1=O]

To a mixture of 4,4-dimethyl-1,3-cyclohexanedione (0.21 g, 1.5 mmol), 4'-chloro-4-ethylbiphen-3-yllead triacetate (1.0 g, 1.7 mmol) and dimethylaminopyridine (0.93 g, 7.6 mmol)

is added anhydrous chloroform (11 ml) and anhydrous toluene (2.8 ml). The reaction mixture is heated at 80° C. for 4 hours and then cooled to room temperature. The mixture is diluted with dichloromethane (50 ml) and 2M aqueous hydrochloric acid (50 ml) and filtered through diatomaceous earth. The filtrate is partitioned, the aqueous layer is extracted with dichloromethane (50 ml) and the organic extracts are combined, washed with 2M aqueous hydrochloric acid (50 ml), brine (50 ml), dried over anhydrous magnesium sulfate, filtered and the filtrate is evaporated under reduced pressure. The crude product is purified by preparative reverse phase HPLC to give 2-(4'-chloro-4-ethylbiphen-3-yl)-4,4-dimethyl-1,3-cyclohexanedione.

Example 2

Preparation of 2-(4'-chloro-4-ethyl-2'-methylbiphen-3-yl)-4,4-dimethylcyclohexane-1,3-dione

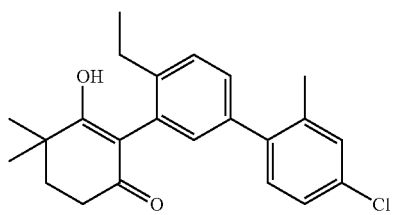 [SMILES: CCc1ccc(-c2ccc(Cl)cc2C)cc1C1=C(O)C(C)(C)CCC1=O]

Step 1: Preparation of 5-bromo-2-ethylaniline

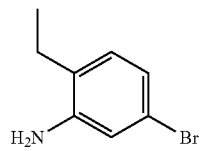

To a solution of 2-ethyl-5-bromo nitrobenzene (9.71 g, 230 mmol) in ethanol (125 ml) is added tin(II) chloride dihydrate (35.72 g, 225.71 mmol), followed by heating at 70° C. for 2 hours. After cooling to room temperature the solution is poured into crushed ice (1 liter) then diluted with ethyl acetate (200 ml). Solid sodium carbonate is cautiously added until pH 7 is achieved, at which stage the viscous mixture is filtered through diatomaceous earth (further washing with ethyl acetate/aqueous sodium carbonate) and the phases separated. After additional extraction of the aqueous phase, all organic phases are combined, dried over anhydrous magnesium sulfate then concentrated in vacuo. The crude oil is purified by flash column chromatography on silica gel (hexane/ethyl acetate 8:2 ratio) to afford 5-bromo-2-ethylaniline (7.89 g) as a brown oil.

Step 2: Preparation of 4-bromo-1-ethyl-2-iodobenzene

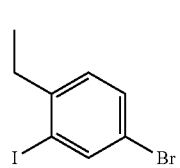

To a stirred mixture of 5-bromo-2-ethylaniline (3.39 g, 200 mmol) in distilled water (110 ml) is added concentrated sulfuric acid (5.60 ml), followed by brief heating at reflux until dissolution. The mixture is allowed to cool to room temperature, producing a fine precipitate, then further cooled to approximately 0° C. in an ice/salt bath. To this slurry is added an aqueous solution of sodium nitrite (1.17 g, 16.94 mmol) in distilled water (10 ml) dropwise over 15 minutes, maintaining a temperature below 5° C., followed by additional stirring for 30 minutes. The reaction mixture is next filtered then added to a second solution of aqueous potassium iodide (8.44 g, 50.83 mmol) in distilled water (45 ml) dropwise at room temperature. After the addition is complete the solution is briefly heated to 80° C. then allowed to cool to room temperature again. The reaction mixture is extracted with ethyl acetate (3×50 ml), and the organic phase is washed with 1M aqueous hydrochloric acid (30 ml) and aqueous sodium thiosulfate (2×30 ml). After drying over anhydrous magnesium sulfate and concentration in vacuo 4-bromo-1-ethyl-2-iodobenzene (4.90 g) is furnished as an orange liquid.

Step 3: Preparation of 5-bromo-2-ethylphenylboronic acid

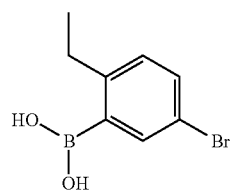

To a solution of 4-bromo-1-ethyl-2-iodobenzene (10.00 g, 32.20 mmol) in anhydrous tetrahydrofuran (60 ml) at −78° C. is added a solution of isopropylmagnesium chloride (16.90 ml, 33.80 mmol, 2M solution in tetrahydrofuran) dropwise, maintaining a temperature below −60° C. After stirring for 20 minutes the reaction mixture is allowed to slowly warm to room temperature followed by an additional hour of stirring. The solution is re-cooled to −78° C. and trimethylborate (7.18 ml, 64.32 mmol) is added dropwise, after which the mixture is again allowed to warm to room temperature with further stirring for 2 hours. Dilute aqueous hydrochloric acid (30 ml) is added, and the crude product is extracted into ethyl acetate (100 ml). The aqueous phase is washed with ethyl acetate (2×100 ml), and all organics are combined, dried over anhydrous magnesium sulfate then concentrated in vacuo to give a light brown solid which is triturated with hexanes to afford 5-bromo-2-ethylphenylboronic acid (6.46 g) as a cream powder.

Step 4: Preparation of 5-bromo-2-ethylphenyllead triacetate

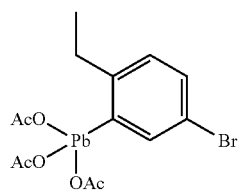

To a mixture of lead tetraacetate (13.7 g, 31.00 mmol) and mercuric diacetate (0.47 g, 1.50 mmol), thoroughly flushed with nitrogen, is added anhydrous chloroform (42 ml). This mixture is warmed to 40° C., and 5-bromo-2-ethylphenylboronic acid (6.50 g, 28.00 mmol) is added in one portion and the suspension is heated at this temperature for 5 hours. The mixture is then allowed to cool to room temperature, followed by further cooling to 0° C. then addition of powdered anhydrous potassium carbonate (3.22 g) with rapid stirring for 5 minutes then filtration. The filtrate is concentrated to half its volume, followed by the addition of hexanes to induce precipitation. This mixture is further concentrated, the solvent decanted, and the solid washed with hexanes to afford 5-bromo-2-ethylphenyllead triacetate (10.69 g) as a sandy coloured solid.

Step 5: Preparation of 2-(5-bromo-2-ethylphenyl)-4,4-dimethylcyclohexane-1,3-dione

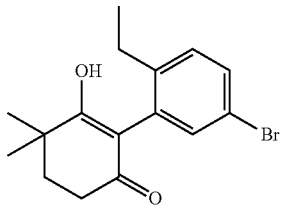 [SMILES: CCc1ccc(Br)cc1C1=C(O)C(C)(C)CCC1=O]

To a mixture of 4,4-dimethylcyclohexane-1,3-dione (6.28 g, 45 mmol), 5-bromo-2-ethylphenyl lead triacetate (28 g, 49 mmol) and dimethylaminopyridine (27.4 g, 0.22 mol) under nitrogen are added anhydrous chloroform (300 ml) and toluene (75 ml). The reaction mixture is heated at 80° C. for 2 hours and then allowed to cool to room temperature overnight. 2M Aqueous hydrochloric acid (750 ml) and dichloromethane (500 ml) are added and the mixture is filtered through diatomaceous earth, washing through with more dichloromethane (250 ml). The two layers are separated and the aqueous phase is extracted with dichloromethane (500 ml). The organic layers are combined and washed with 2M aqueous hydrochloric acid (1000 ml) and then brine (1000 ml), dried over anhydrous magnesium sulfate, filtered and the filtrate is evaporated under reduced pressure. The residue is purified by preparative normal phase chromatography to give 2-(5-bromo-2-ethylphenyl)-4,4-dimethylcyclohexane-1,3-dione (6.78 g).

Step 6: Preparation of 2-(4'-chloro-4-ethyl-2'-methylbiphen-3-yl)-4,4-dimethylcyclohexane-1,3-dione

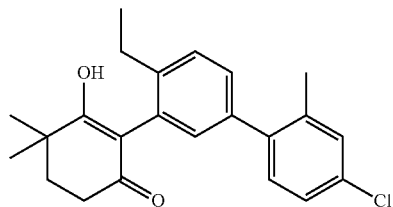 [SMILES: CCc1ccc(-c2ccc(Cl)cc2C)cc1C1=C(O)C(C)(C)CCC1=O]

A mixture of 2-(5-bromo-2-ethylphenyl)-4,4-dimethylcyclohexane-1,3-dione (0.194 g, 0.6 mmol), 2-methyl-4-chloro-phenylboronic acid (0.153 g, 0.9 mmol), [1,1'-bis(diphenylphosphino)ferrocene]dichloropalladium(II) (complex with dichloromethane 1:1) (80 mg, 0.098 mmol) and cesium fluoride (0.608 g, 4 mmol) are stirred together in 1,2-dimethoxyethane (4 ml) and the reaction mixture is heated at 80° C. overnight. The warm reaction mixture is filtered, washing the filter cake with 9:1 dichloromethane:methanol. The mixture is concentrated under reduced pressure and the residue is purified by column chromatography on silica gel to give 2-(4'-chloro-4-ethyl-2'-methylbiphen-3-yl)-4,4-dimethyl-cyclohexane-1,3-dione.

Additional compounds in Table A are prepared by analogous procedures, from appropriate starting materials. Typically compounds are purified by column chromatography on silica gel, but where necessary they may be further purified by preparative reverse phase HPLC. It should be noted that certain compounds of the invention exist as a mixture of atropisomers, or other isomers noted above, under the conditions used to obtain the $^1$H nmr data. Where this has occurred, the characterising data are reported for individual isomers or mixture of atropisomers, or other isomers, present at ambient temperature in the specified solvent.

TABLE A

| Compound Number | Structure | $^1$H nmr (CDCl$_3$ unless stated) or other physical data |
|---|---|---|
| T1 | 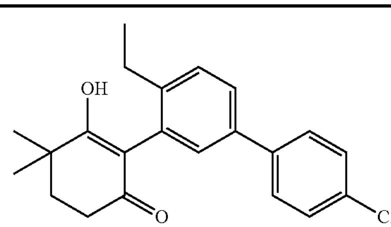 | δ 1.09-1.16 (m, 3H), 1.22 (d, 3.7H), 1.37 (d, 2.3H), 1.89-2.05 (m, 2H), 2.36-2.50 (m, 2H), 2.58-2.75 (m, 2H), 5.47-5.52 (m, 1H), 7.20-7.23 (m, 1H), 7.35-7.43 (m, 3H), 7.49 (d, 2H), 7.47-7.55 (m, 1H). |
| T2 | 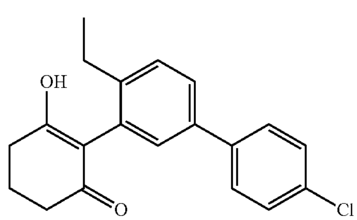 [SMILES: CCc1ccc(-c2ccc(Cl)cc2)cc1C1=C(O)CCCC1=O] | δ 1.14 (t, 3H), 2.11 (quintet, 2H), 2.39-2.66 (m, 6H), 5.89 (br. s, 1H), 7.23 (d, 1H), 7.34-7.42 (m, 3H), 7.48 (d, 2H), 7.52 (dd, 1H). |

TABLE A-continued

| Compound Number | Structure | ¹H nmr (CDCl₃ unless stated) or other physical data |
|---|---|---|
| T3 | 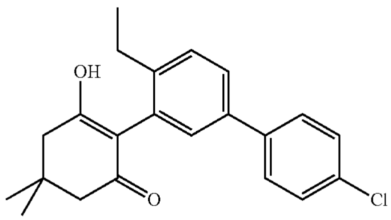 [SMILES: CCc1ccc(-c2ccc(Cl)cc2)cc1C1=C(O)CC(C)(C)CC1=O] | δ 1.15 (t, 3H), 1.21 (s, 6H), 2.40-2.55 (m, 6H), 5.62 (br. s, 1H), 7.27 (dd, 1H), 7.35-7.44 (m, 3H), 7.49 (d, 2H), 7.53 (dd, 1H). |
| T4 | 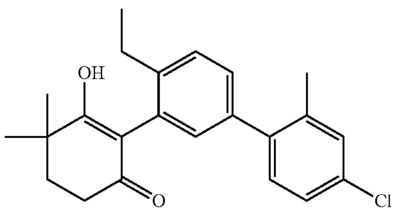 [SMILES: CCc1ccc(-c2ccc(Cl)cc2C)cc1C1=C(O)C(C)(C)CCC1=O] | δ 1.10-1.15 (m, 3H), 1.16 (s, 2H), 1.21 (s, 2H), 1.31-1.36 (m, 2H), 1.86-1.98 (m, 2H), 2.25 (s, 3H), 2.33-2.50 (m, 2H), 2.50-2.69 (m, 2H), 5.62 (br. s, 0.3H), 5.90-5.95 (m, 0.7H), 6.92-6.96 (m, 1H), 7.11-7.20 (m, 2H), 7.20-7.28 (m, 2H), 7.31-7.38 (m, 1H). |
| T5 | 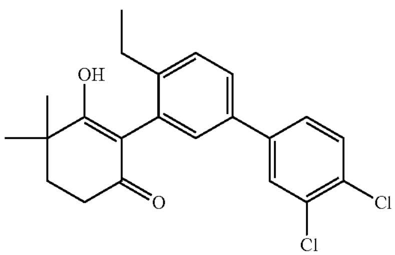 [SMILES: CCc1ccc(-c2ccc(Cl)c(Cl)c2)cc1C1=C(O)C(C)(C)CCC1=O] | δ 1.09 (t, 3H), 1.18 (s, 2H), 1.20 (s, 2H), 1.35 (s, 2H), 1.85-2.00 (m, 2H), 2.32-2.47 (m, 2H), 2.51-2.67 (m, 2H), 5.64 (br. s, 0.3H), 6.11 (br. s, 0.7H), 7.17 (s, 1H), 7.33-7.40 (m, 2H), 7.43-7.50 (m, 2H), 7.61-7.64 (m, 1H) |
| T6 | 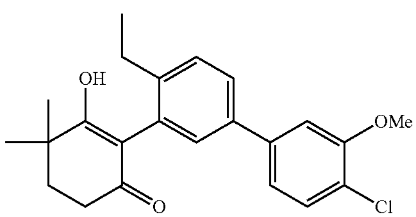 [SMILES: CCc1ccc(-c2ccc(Cl)c(OC)c2)cc1C1=C(O)C(C)(C)CCC1=O] | δ 1.08-1.16 (m, 3H), 1.20 (s, 2H), 1.23 (s, 2H), 1.35-1.37 (m, 2H), 1.90-2.02 (m, 2H), 2.35-2.48 (m, 2H), 2.56-2.72 (m, 2H), 3.95 (s, 3H), 5.58 (br. s, 0.35H), 5.74 (br. s, 0.65H), 7.05-7.09 (m, 2H), 7.19 (s, 1H), 7.35-7.42 (m, 2H), 7.48-7.53 (m, 1H). |
| T7 | 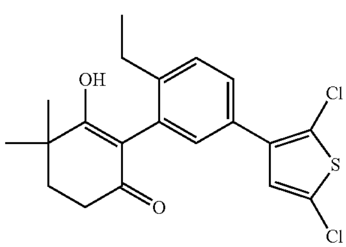 [SMILES: CCc1ccc(-c2cc(Cl)sc2Cl)cc1C1=C(O)C(C)(C)CCC1=O] | δ 1.08-1.15 (m, 3H), 1.18 (s, 2H), 1.21 (s, 2H), 1.33-1.36 (m, 2H), 1.86-2.00 (m, 2H), 2.35-2.50 (m, 2H), 2.55-2.72 (m, 2H), 5.57-5.60 (m, 0.3H), 5.73-5.78 (m, 0.7H), 6.89 (s, 1H), 7.15 (s, 1H), 7.37 (t, 1H), 7.47-7.53 (m, 1H). |
| T8 | 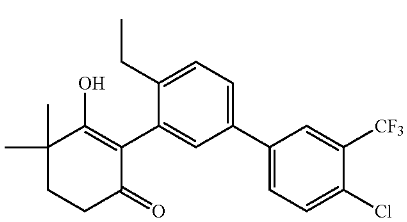 [SMILES: CCc1ccc(-c2ccc(Cl)c(C(F)(F)F)c2)cc1C1=C(O)C(C)(C)CCC1=O] | δ 1.07-1.15 (m, 3H), 1.18 (s, 2H), 1.21 (s, 2H), 1.36 (s, 2H), 1.85-2.01 (m, 2H), 2.33-2.49 (m, 2H), 2.53-2.70 (m, 2H), 5.59 (br. s, 0.35H), 5.99 (br. s, 0.65H), 7.20 (s, 1H), 7.35-7.44 (m, 1H), 7.47-7.55 (m, 2H), 7.64 (d, 1H), 7.83-7.87 (m, 1H). |

TABLE A-continued

| Compound Number | Structure | ¹H nmr (CDCl₃ unless stated) or other physical data |
|---|---|---|
| T9 | *(structure: 4,4-dimethyl-3-hydroxy-2-[2-ethyl-5-(5-chlorothiophen-2-yl)phenyl]cyclohex-2-enone)* | δ 1.05-1.13 (m, 3H), 1.18 (s, 2H), 1.20 (s, 2H), 1.35 (s, 2H), 1.86-2.01 (m, 2H), 2.30-2.46 (m, 2H), 2.54-2.70 (m, 2H), 5.54 (s, 0.35H), 5.76 (s, 0.65H), 6.83-6.87 (m, 1H), 6.99-7.03 (m, 1H), 7.12-7.15 (m, 1H), 7.27-7.34 (m, 1H), 7.41-7.47 (m, 1H). |
| T10 | *(structure: 4,4-dimethyl-3-hydroxy-2-[2-ethyl-5-(3-fluoro-4-chlorophenyl)phenyl]cyclohex-2-enone)* | δ 1.07-1.15 (m, 3H), 1.18 (s, 2H), 1.21 (s, 2H), 1.36 (s, 2H), 1.84-2.01 (m, 2H), 2.33-2.50 (m, 2H), 2.52-2.70 (m, 2H), 5.58 (br. s, 0.3H), 5.90 (br. s, 0.7H), 7.17-7.20 (m, 1H), 7.27-7.36 (m, 2H), 7.36-7.44 (m, 2H), 7.45-7.52 (m, 1H). |
| T11 | *(structure: 4,4-dimethyl-3-hydroxy-2-[2-ethyl-5-(6-chloropyridin-3-yl)phenyl]cyclohex-2-enone)* | δ 1.13 (t, 3H), 1.17-1.29 (m, 4H), 1.32-1.45 (m, 2H), 1.90-2.03 (m, 2H), 2.50 (q, 2H), 2.57-2.81 (m, 2H), 7.16-7.34 (m, 4H), 7.71-7.80 (m, 1H), 8.13-8.26 (m, 1H). |
| T12 | *(structure: 4,4-dimethyl-3-hydroxy-2-[2-ethyl-5-(2,6-dichloropyridin-3-yl)phenyl]cyclohex-2-enone)* | δ 1.10-1.20 (m, 5H), 1.20-1.28 (m, 2H), 1.32-1.40 (m, 2H), 1.88-2.02 (m, 2H), 2.37-2.53 (m, 2H), 2.53-2.73 (m, 2H), 5.67 (br. s, 0.3H), 5.88 (br. s, 0.7H), 7.10 (s, 1H), 7.31 (d, 1H), 7.35-7.46 (m, 2H), 7.65 (d, 1H). |
| T13 | *(structure: 4,4-dimethyl-3-hydroxy-2-[2-ethyl-5-(2,6-difluoro-4-chlorophenyl)phenyl]cyclohex-2-enone)* | δ 1.01-1.09 (m, 2H), 1.10-1.23 (m, 5H), 1.30-1.37 (m, 2H), 1.83-2.01 (m, 2H), 2.23-2.49 (m, 2H), 2.50-2.66 (m, 2H), 5.60-5.90 (m, 0.5H), 6.15-6.22 (m, 0.5H), 6.97-7.03 (m, 1H), 7.08-7.21 (m, 2H), 7.35-7.46 (m, 2H). |
| T14 | *(structure: 4,4-dimethyl-3-hydroxy-2-[2-ethyl-5-(2,4-dichloro-6-fluorophenyl)phenyl]cyclohex-2-enone)* | δ 1.02-1.10 (m, 2H), 1.11-1.28 (m, 5H), 1.31-1.37 (m, 2H), 1.84-1.99 (m, 2H), 2.23-2.49 (m, 2H), 2.51-2.70 (m, 2H), 5.46-5.77 (m, 1H), 7.00-7.23 (m, 3H), 7.28-7.48 (m, 2H). |
| T15 | *(structure: 4,4-dimethyl-3-hydroxy-2-[2-ethyl-5-(2-chloro-3-fluoro-4-chlorophenyl)phenyl]cyclohex-2-enone)* | δ 1.06-1.10 (m, 3H), 1.16 (s, 2H), 1.24 (s, 2H), 1.33-1.40 (m, 2H), 1.87-2.02 (m, 2H), 2.36-2.54 (m, 2H), 2.55-2.75 (m, 2H), 5.60 (s, 0.3H), 5.67 (s, 0.7H), 7.05-7.15 (m, 2H), 7.28-7.46 (m, 3H). |

TABLE A-continued

| Compound Number | Structure | ¹H nmr (CDCl₃ unless stated) or other physical data |
|---|---|---|
| T16 | 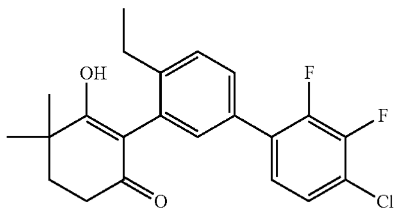 [SMILES: CCc1ccc(-c2ccc(Cl)c(F)c2F)cc1C1=C(O)C(C)(C)CCC1=O] | δ 1.07-1.14 (m, 3H), 1.15-1.21 (m, 4H), 1.32-1.37 (m, 2H), 1.83-1.99 (m, 2H), 2.34-2.48 (m, 2H), 2.49-2.67 (m, 2H), 5.79 (br. s, 0.3H), 6.33 (br. s, 0.7H), 7.08-7.21 (m, 3H), 7.33-7.50 (m, 2H). |
| T17 | 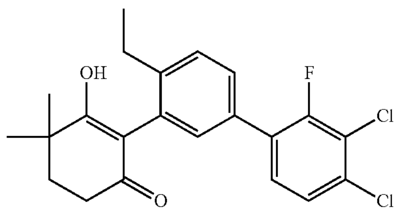 [SMILES: CCc1ccc(-c2ccc(Cl)c(Cl)c2F)cc1C1=C(O)C(C)(C)CCC1=O] | δ 1.07-1.14 (m, 3H), 1.16 (s, 2H), 1.20 (s, 2H), 1.32-1.37 (m, 2H), 1.84-1.99 (m, 2H), 2.33-2.49 (m, 2H), 2.50-2.68 (m, 2H), 5.79 (br. s, 0.3H), 6.29 (br. s, 0.7H), 7.12-7.16 (m, 1H), 7.22-7.30 (m, 2H), 7.33-7.47 (m, 2H). |
| T18 | 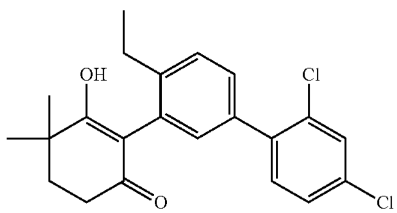 | δ 1.10-1.19 (m, 4H), 1.21-1.29 (m, 3H), 1.33-1.37 (m, 2H), 1.89-2.00 (m, 2H), 2.36-2.54 (m, 2H), 2.56-2.74 (m, 2H), 5.62 (s, 1H), 7.09 (s, 1H), 7.28 (s, 2H), 7.35-7.42 (m, 2H), 7.47 (s, 1H). |
| T19 | 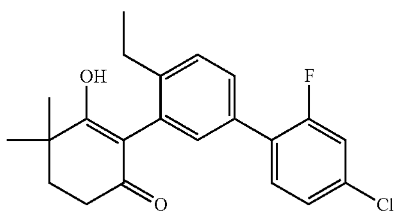 | δ 1.06-1.14 (m, 3H), 1.14-1.27 (m, 4H), 1.32-1.37 (m, 2H), 1.84-1.99 (m, 2H), 2.34-2.47 (m, 2H), 2.49-2.67 (m, 2H), 5.74 (br. s, 0.3H), 6.15 (0.7H), 7.11-7.18 (m, 3H), 7.31-7.41 (m, 2H), 7.42-7.49 (m, 1H). |
| T20 | 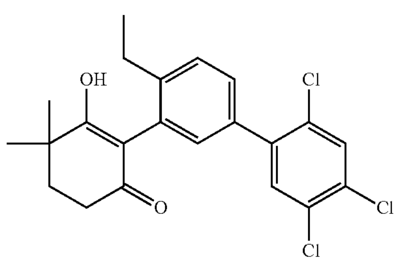 [SMILES: CCc1ccc(-c2cc(Cl)c(Cl)cc2Cl)cc1C1=C(O)C(C)(C)CCC1=O] | δ 1.11-1.18 (m, 3H), 1.18-1.29 (m, 4H), 1.33-1.38 (m, 2H), 1.88-2.01 (m, 2H), 2.34-2.54 (m, 2H), 2.54-2.76 (m, 2H), 5.58 (s, 0.3H), 5.63 (0.7H), 7.08 (s, 1H), 7.32-7.43 (m, 2H), 7.46 (s, 1H), 7.56 (s, 1H). |
| T21 | 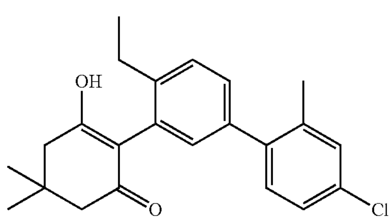 [SMILES: CCc1ccc(-c2ccc(Cl)cc2C)cc1C1=C(O)CC(C)(C)CC1=O] | δ 1.13-1.18 (m, 6H), 1.20 (s, 3H), 2.26 (s, 3H), 2.39 (s, 2H), 2.41-2.55 (m, 4H), 5.73 (s, 1H), 6.96 (s, 1H), 7.14 (d, 1H), 7.18 (d, 1H) 7.23-7.28 (m, 2H), 7.37 (d, 1H). |
| T22 | 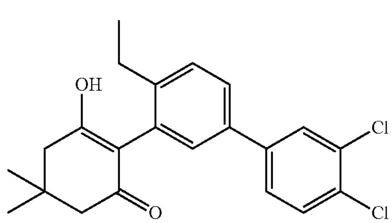 [SMILES: CCc1ccc(-c2ccc(Cl)c(Cl)c2)cc1C1=C(O)CC(C)(C)CC1=O] | δ 1.13 (t, 3H), 1.19 (s, 6H), 2.39 (s, 2H), 2.42-2.56 (m, 4H), 6.03 (s, 1H), 7.19 (s, 1H), 7.35-7.41 (m, 2H), 7.44-7.51 (m, 2H), 7.62 (s, 1H). |

TABLE A-continued
| Compound Number | Structure | ¹H nmr (CDCl₃ unless stated) or other physical data |
|---|---|---|
| T23 | 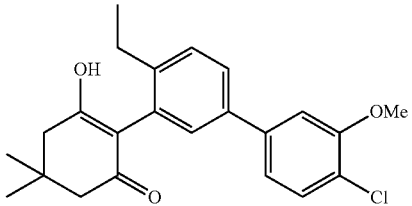 [SMILES: CCc1ccc(-c2ccc(Cl)c(OC)c2)cc1C1=C(O)CC(C)(C)CC1=O] | δ 1.14 (t, 3H), 1.20 (s, 6H), 2.41 (s, 2H), 2.42-2.57 (m, 4H), 3.94 (s, 3H), 5.93 (s, 1H), 7.04-7.09 (m, 2H), 7.20 (s, 1H), 7.36-7.41 (m, 2H), 7.51 (d, 1H). |
| T24 | 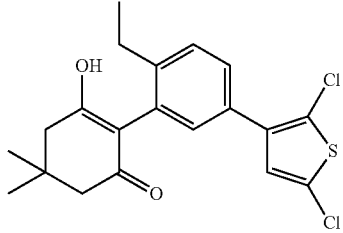 [SMILES: CCc1ccc(-c2cc(Cl)sc2Cl)cc1C1=C(O)CC(C)(C)CC1=O] | δ 1.12 (t, 3H), 1.15-1.21 (m, 6H), 2.33-2.54 (m, 6H), 6.24 (s, 1H), 6.88 (s, 1H), 7.16 (s, 1H), 7.37 (d, 1H), 7.48 (d, 1H). |
| T25 | 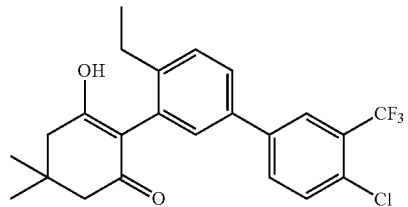 [SMILES: CCc1ccc(-c2ccc(Cl)c(C(F)(F)F)c2)cc1C1=C(O)CC(C)(C)CC1=O] | δ 1.12 (t, 3H), 1.18-1.21 (m, 6H), 2.40-2.54 (m, 6H), 4.88 (br. s, 1H), 7.19 (s, 1H), 7.36 (d, 1H), 7.49 (dd, 1H), 7.60 (d, 1H), 7.78 (d, 1H), 7.91 (s, 1H). |
| T26 | 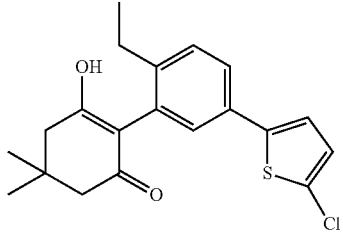 [SMILES: CCc1ccc(-c2ccc(Cl)s2)cc1C1=C(O)CC(C)(C)CC1=O] | δ 1.12 (t, 3H), 1.21 (s, 6H), 2.39-2.60 (m, 6H), 5.55 (s, 1H), 6.86 (d, 1H), 7.01 (d, 1H), 7.16 (s, 1H), 7.35 (d, 1H), 7.47 (d, 1H). |
| T27 | 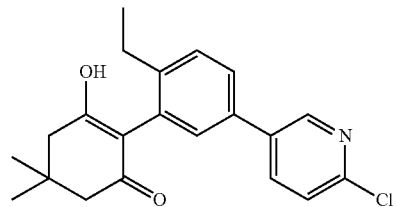 [SMILES: CCc1ccc(-c2ccc(Cl)nc2)cc1C1=C(O)CC(C)(C)CC1=O] | δ 1.14 (t, 3H), 1.21 (s, 6H), 2.41 (s, 2H), 2.51-2.58 (m, 4H), 7.18-7.24 (m, 2H), 7.24-7.29 (m, 1H), 7.73-7.80 (m, 2H), 8.15 (d, 1H). |
| T28 | 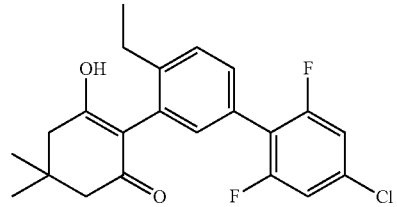 [SMILES: CCc1ccc(-c2c(F)cc(Cl)cc2F)cc1C1=C(O)CC(C)(C)CC1=O] | δ 1.13-1.24 (m, 9H), 2.37-2.42 (m, 2H), 2.42-2.58 (m, 4H), 5.52 (s, 0.15H), 5.65 (s, 0.85H), 6.98-7.05 (m, 2H), 7.12 (s, 1H), 7.40-7.46 (m, 2H). |
| T29 | 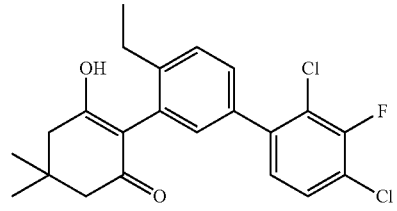 [SMILES: CCc1ccc(-c2ccc(Cl)c(F)c2Cl)cc1C1=C(O)CC(C)(C)CC1=O] | δ 1.13-1.18 (m, 6H), 1.19 (s, 3H), 2.38 (br. s, 2H), 2.44-2.55 (m, 4H), 6.08 (s, 1H), 7.08-7.11 (m, 2H), 7.32 (t, 1H), 7.35-7.42 (m, 2H). |

TABLE A-continued

| Compound Number | Structure | ¹H nmr (CDCl₃ unless stated) or other physical data |
|---|---|---|
| T30 | 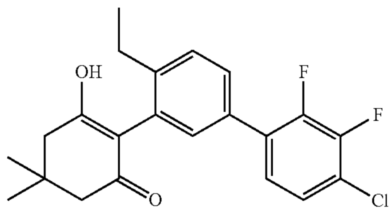 [SMILES: CCc1ccc(-c2ccc(Cl)c(F)c2F)cc1C1=C(O)CC(C)(C)CC1=O] | δ 1.15 (t, 3H), 1.19 (s, 3H), 1.20 (s, 3H), 2.40 (s, 2H), 2.44-2.58 (m, 4H), 5.93 (s, 1H), 7.11-7.16 (m, 1H), 7.16-7.22 (m, 2H), 7.43 (d, 1H), 7.49 (d, 1H). |
| T31 | 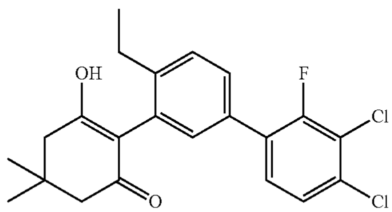 [SMILES: CCc1ccc(-c2ccc(Cl)c(Cl)c2F)cc1C1=C(O)CC(C)(C)CC1=O] | δ 1.15 (t, 3H), 1.19 (s, 3H), 1.20 (s, 3H), 2.40 (s, 2H), 2.44-2.57 (m, 4H), 5.86 (s, 1H), 7.17 (s, 1H), 7.24-7.30 (m, 2H), 7.43 (d, 1H), 7.48 (d, 1H). |
| T32 | 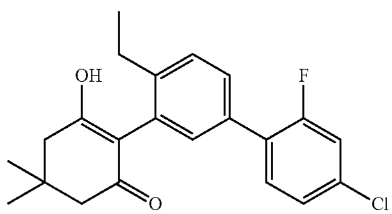 [SMILES: CCc1ccc(-c2ccc(Cl)cc2F)cc1C1=C(O)CC(C)(C)CC1=O] | δ 1.15 (t, 3H), 1.19 (s, 3H), 1.20 (s, 3H), 2.40 (s, 2H), 2.44-2.58 (m, 4H), 5.79 (s, 1H), 7.13-7.20 (m, 3H), 7.36 (t, 1H), 7.42 (d, 1H), 7.49 (d, 1H). |
| T33 | 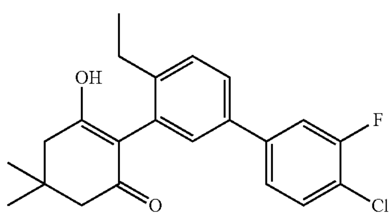 [SMILES: CCc1ccc(-c2ccc(Cl)c(F)c2)cc1C1=C(O)CC(C)(C)CC1=O] | δ 1.12 (t, 3H), 1.17 (s, 6H), 2.34-2.55 (m, 6H), 6.33 (br. s, 1H), 7.18 (s, 1H), 7.26 (d, 1H), 7.31 (d, 1H), 7.35-7.40 (m, 2H), 7.47 (d, 1H). |
| T34 | 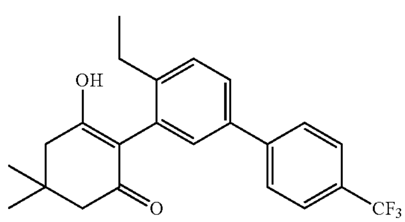 [SMILES: CCc1ccc(-c2ccc(C(F)(F)F)cc2)cc1C1=C(O)CC(C)(C)CC1=O] | δ 1.07 (t, 0.5H), 1.13 (t, 2.5H), 1.15-1.22 (m, 6H), 2.36-2.53 (m, 6H), 4.88 (s, 1H), 7.24 (s, 1H), 7.36 (d, 1H), 7.54 (dd, 1H), 7.68 (d, 2H), 7.76 (d, 2H). |
| T35 | 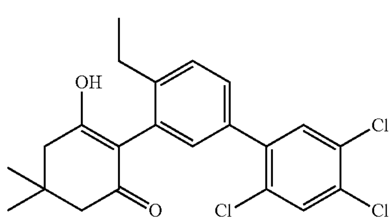 [SMILES: CCc1ccc(-c2cc(Cl)c(Cl)cc2Cl)cc1C1=C(O)CC(C)(C)CC1=O] | δ 1.16 (t, 3H), 1.19 (s, 3H), 1.21 (s, 3H), 2.41 (s, 2H), 2.44-2.58 (m, 4H), 5.73 (br. s, 1H), 7.10 (s, 1H), 7.37-7.44 (m, 2H), 7.45 (s, 1H), 7.57 (s, 1H). |
| T36 | 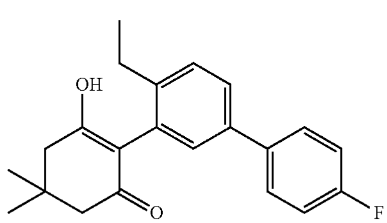 [SMILES: CCc1ccc(-c2ccc(F)cc2)cc1C1=C(O)CC(C)(C)CC1=O] | δ 1.14 (t, 3H), 1.20 (s, 6H), 2.40-2.56 (m, 6H), 5.72 (br. s, 1H), 7.09 (t, 2H), 7.20 (s, 1H), 7.40 (d, 1H), 7.48-7.53 (m, 3H). |

TABLE A-continued

| Compound Number | Structure | ¹H nmr (CDCl₃ unless stated) or other physical data |
|---|---|---|
| T37 | 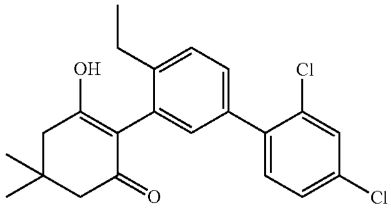 [SMILES: CCc1ccc(-c2ccc(Cl)cc2Cl)cc1C1=C(O)CC(C)(C)CC1=O] | δ 1.14-1.20 (m, 6H), 1.21 (s, 3H), 2.38-2.57 (m, 6H), 5.77 (br. s, 1H), 7.11 (s, 1H), 7.29 (s, 2H), 7.37-7.44 (m, 2H), 7.47 (s, 1H). |
| T38 | 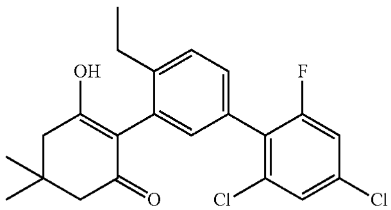 [SMILES: CCc1ccc(-c2c(F)cc(Cl)cc2Cl)cc1C1=C(O)CC(C)(C)CC1=O] | δ 1.15-1.19 (m, 6H), 1.20 (s, 3H), 2.40 (s, 2H), 2.42-2.59 (m, 4H), 5.75 (br. s, 1H), 7.03 (s, 1H), 7.11 (d, 1H), 7.30-7.35 (m, 2H), 7.44 (d, 1H). |
| T39 | 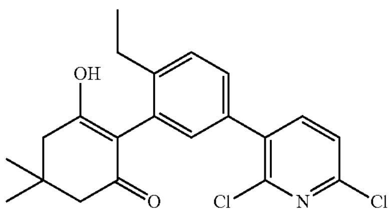 [SMILES: CCc1ccc(-c2ccc(Cl)nc2Cl)cc1C1=C(O)CC(C)(C)CC1=O] | δ 1.14-1.20 (m, 6H), 1.21 (s, 3H), 2.41 (s, 2H), 2.43-2.58 (m, 4H), 5.75 (br. s, 1H), 7.13 (s, 1H), 7.33 (d, 1H), 7.39-7.47 (m, 2H), 7.66 (d, 1H). |
| T40 | 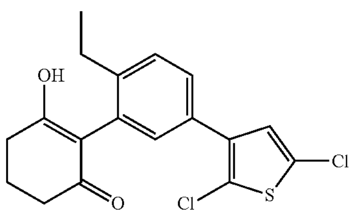 [SMILES: CCc1ccc(-c2cc(Cl)sc2Cl)cc1C1=C(O)CCCC1=O] | δ 1.15 (t, 3H), 2.08-2.18 (m, 2H), 2.40-2.56 (m, 4H), 2.61-2.67 (m, 2H), 5.76 (br. s, 1H), 6.89 (s, 1H), 7.21 (s, 1H), 7.40 (d, 1H), 7.51 (d, 1H). |
| T41 | 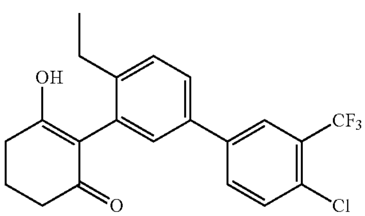 [SMILES: CCc1ccc(-c2ccc(Cl)c(C(F)(F)F)c2)cc1C1=C(O)CCCC1=O] | δ 1.10 (t, 0.4H), 1.16 (t, 2.6H), 2.08-2.20 (m, 2H), 2.43-2.58 (m, 4H), 2.60-2.70 (m, 2H), 5.60 (s, 1H), 7.24-7.27 (m, 1H), 7.45 (d, 1H), 7.52-7.57 (m, 2H), 7.65 (d, 1H), 7.85 (s, 1H). |
| T42 | 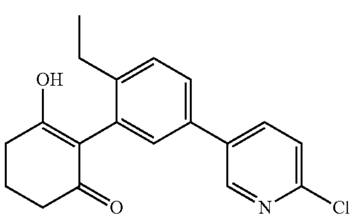 [SMILES: CCc1ccc(-c2ccc(Cl)nc2)cc1C1=C(O)CCCC1=O] | δ 1.16 (t, 3H), 2.11-2.19 (m, 2H), 2.46-2.59 (m, 4H), 2.61-2.71 (m, 2H), 6.51 (br. s, 1H), 7.22-7.28 (m, 1H), 7.33 (d, 1H), 7.36-7.42 (m, 2H), 7.79 (dd, 1H), 8.39 (s, 1H). |
| T43 | 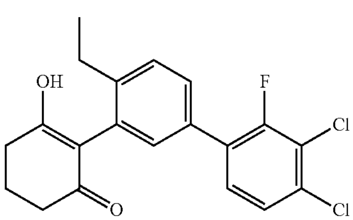 [SMILES: CCc1ccc(-c2ccc(Cl)c(Cl)c2F)cc1C1=C(O)CCCC1=O] | δ 1.15 (t, 3H), 2.08-2.15 (m, 2H), 2.42-2.56 (m, 4H), 2.60-2.67 (m, 2H), 5.87 (br. s, 1H), 7.20 (s, 1H), 7.24-7.32 (m, 2H), 7.43 (d, 1H), 7.48 (d, 1H). |

TABLE A-continued

| Compound Number | Structure | ¹H nmr (CDCl₃ unless stated) or other physical data |
|---|---|---|
| T44 | 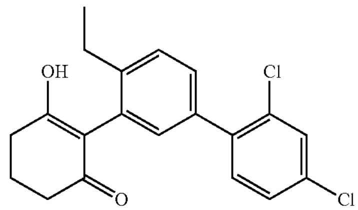 [SMILES: CCc1ccc(-c2ccc(Cl)cc2Cl)cc1C1=C(O)CCCC1=O] | δ 1.09 (t, 0.5H), 1.17 (t, 2.5H), 2.07-2.16 (m, 2H), 2.42-2.56 (m, 4H), 2.58-2.68 (m, 2H), 5.84 (br. s, 1H), 7.13 (s, 1H), 7.25-7.30 (m, 2H), 7.37-7.43 (m, 2H), 7.47 (s, 1H). |
| T45 | 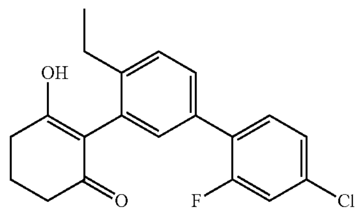 [SMILES: CCc1ccc(-c2ccc(Cl)cc2F)cc1C1=C(O)CCCC1=O] | δ 1.16 (m, 3H), 2.10-2.18 (m, 2H), 2.41-2.56 (m, 4H), 2.63-2.68 (m, 2H), 5.69 (s, 1H), 7.15-7.22 (m, 3H), 7.37 (t, 1H), 7.43 (d, 1H), 7.51 (d, 1H). |
| T46 | 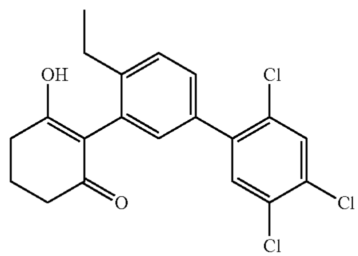 [SMILES: CCc1ccc(-c2cc(Cl)c(Cl)cc2Cl)cc1C1=C(O)CCCC1=O] | δ 1.17 (t, 3H), 2.09-2.17 (m, 2H), 2.42-2.57 (m, 4H), 2.62-2.68 (m, 2H), 5.73 (s, 1H), 7.12 (s, 1H), 7.38-7.44 (m, 2H), 7.46 (s, 1H), 7.57 (s, 1H). |
| T47 | 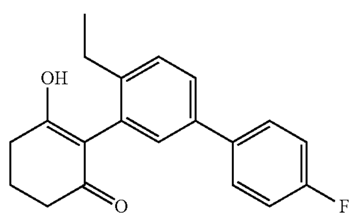 [SMILES: CCc1ccc(-c2ccc(F)cc2)cc1C1=C(O)CCCC1=O] | δ 1.09 (t, 0.3H), 1.15 (t, 2.7H), 2.06-2.17 (m, 2H), 2.40-2.58 (m, 4H), 2.58-2.67 (m, 2H), 5.74 (br. s, 1H), 7.09 (t, 2H), 7.18-7.23 (m, 1H), 7.40 (d, 1H), 7.48-7.53 (m, 3H). |
| T48 | 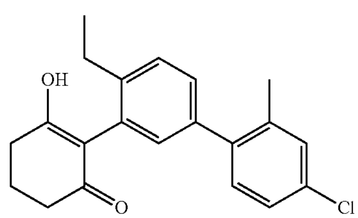 [SMILES: CCc1ccc(-c2ccc(Cl)cc2C)cc1C1=C(O)CCCC1=O] | δ 1.14-1.24 (m, 3H), 2.09-2.19 (m, 2H), 2.31 (s, 3H), 2.43-2.60 (m, 4H), 2.61-2.72 (m, 2H), 5.68 (br. s, 1H), 6.98-7.04 (m, 1H), 7.12-7.24 (m, 2H), 7.24-7.33 (m, 2H), 7.36-7.45 (m, 1H). |
| T49 | 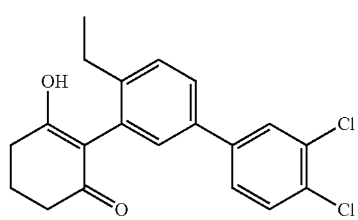 [SMILES: CCc1ccc(-c2ccc(Cl)c(Cl)c2)cc1C1=C(O)CCCC1=O] | δ 1.15 (t, 3H), 2.10-2.18 (m, 2H), 2.40-2.51 (m, 2H), 2.52-2.57 (m, 2H), 2.63-2.68 (m, 2H), 5.61 (br. s, 1H), 7.24 (s, 1H), 7.39 (dd, 1H), 7.43 (d, 1H), 7.47 (d, 1H), 7.52 (d, 1H), 7.64 (s, 1H). |
| T50 | 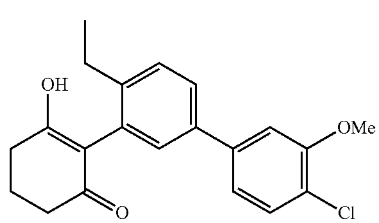 [SMILES: CCc1ccc(-c2ccc(Cl)c(OC)c2)cc1C1=C(O)CCCC1=O] | δ 1.15 (t, 3H), 2.09-2.17 (m, 2H), 2.40-2.68 (m, 6H), 3.95 (s, 3H), 7.06-7.09 (m, 2H), 7.23 (s, 1H), 7.36-7.42 (m, 2H), 7.53 (dd, 1H). |

TABLE A-continued

| Compound Number | Structure | ¹H nmr (CDCl₃ unless stated) or other physical data |
|---|---|---|
| T51 | 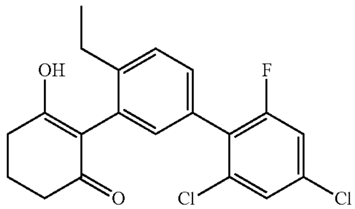 [SMILES: CCc1ccc(-c2c(F)cc(Cl)cc2Cl)cc1C1=C(O)CCCC1=O] | δ 1.17 (t, 3H), 2.08-2.16 (m, 2H), 2.42-2.58 (m, 4H), 2.59-2.69 (m, 2H), 5.83 (br. s, 1H), 7.08-7.13 (m, 2H), 7.33 (t, 1H), 7.37-7.44 (m, 2H). |
| T52 | 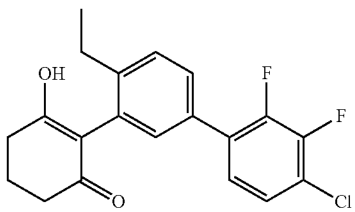 [SMILES: CCc1ccc(-c2ccc(Cl)c(F)c2F)cc1C1=C(O)CCCC1=O] | δ 1.15 (t, 3H), 2.08-2.17 (m, 2H), 2.42-2.58 (m, 4H), 2.59-2.69 (m, 2H), 5.81 (br. s, 1H), 7.11-7.17 (m, 1H), 7.17-7.23 (m, 2H), 7.43 (d, 1H), 7.50 (d, 1H). |
| T53 | 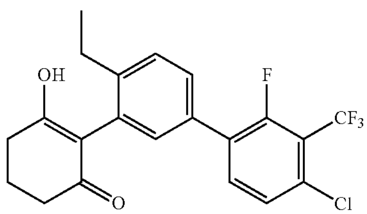 [SMILES: CCc1ccc(-c2ccc(Cl)c(C(F)(F)F)c2F)cc1C1=C(O)CCCC1=O] | δ 1.16 (t, 3H), 2.08-2.17 (m, 2H), 2.43-2.56 (m, 4H), 2.63-2.68 (m, 2H), 5.76 (br. s, 1H), 7.19 (s, 1H), 7.34 (d, 1H), 7.42-7.49 (m, 2H), 7.51 (t, 1H). |
| T54 | 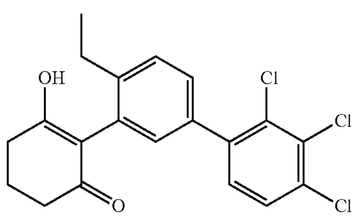 [SMILES: CCc1ccc(-c2ccc(Cl)c(Cl)c2Cl)cc1C1=C(O)CCCC1=O] | δ 1.17 (t, 3H), 2.08-2.16 (m, 2H), 2.43-2.58 (m, 4H), 2.59-2.68 (m, 2H), 7.10 (d, 1H), 7.20 (d, 1H), 7.37 (dd, 1H), 7.39-7.44 (m, 2H). |
| T55 | 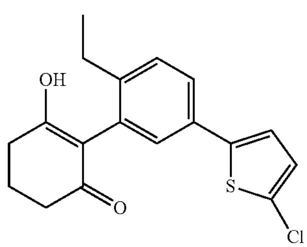 [SMILES: CCc1ccc(-c2ccc(Cl)s2)cc1C1=C(O)CCCC1=O] | δ 1.12 (t, 3H), 2.08-2.17 (m, 2H), 2.37-2.49 (m, 2H), 2.50-2.56 (m, 2H), 2.62-2.67 (m, 2H), 5.91 (br. s, 1H), 6.86 (d, 1H), 7.02 (d, 1H), 7.18 (s, 1H), 7.34 (d, 1H), 7.46 (dd, 1H). |
| T56 | 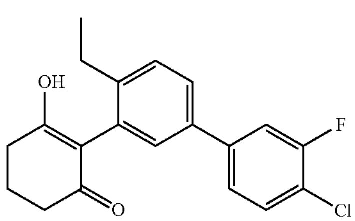 [SMILES: CCc1ccc(-c2ccc(Cl)c(F)c2)cc1C1=C(O)CCCC1=O] | δ 1.15 (t, 3H), 2.11-2.18 (m, 2H), 2.41-2.52 (m, 2H), 2.52-2.57 (m, 2H), 2.64-2.68 (m, 2H), 5.62 (br. s, 1H), 7.24 (d, 1H), 7.29 (dd, 1H), 7.34 (dd, 1H), 7.39-7.45 (m, 2H), 7.53 (dd, 1H). |
| T57 | 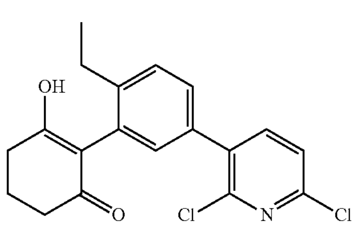 [SMILES: CCc1ccc(-c2ccc(Cl)nc2Cl)cc1C1=C(O)CCCC1=O] | δ 1.17 (t, 3H), 2.09-2.16 (m, 2H), 2.42-2.57 (m, 4H), 2.63-2.68 (m, 2H), 6.05 (br. s, 1H), 7.16 (s, 1H), 7.33 (d, 1H), 7.39-7.46 (m, 2H), 7.66 (d, 1H). |

TABLE A-continued

| Compound Number | Structure | ¹H nmr (CDCl₃ unless stated) or other physical data |
|---|---|---|
| T58 | 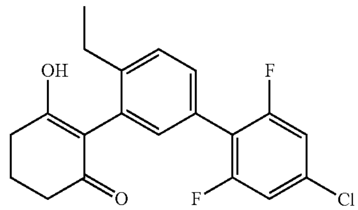 [SMILES: CCc1ccc(-c2c(F)cc(Cl)cc2F)cc1C1=C(O)CCCC1=O] | δ 1.16 (t, 3H), 2.08-2.15 (m, 2H), 2.43-2.65 (m, 6H), 6.99-7.03 (m, 2H), 7.14 (s, 1H), 7.42-7.44 (m, 2H). |
| T59 | 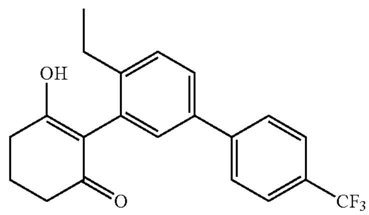 [SMILES: CCc1ccc(-c2ccc(C(F)(F)F)cc2)cc1C1=C(O)CCCC1=O] | δ 1.16 (t, 3H), 2.10-2.17 (m, 2H), 2.42-2.51 (m, 2H), 2.51-2.57 (m, 2H), 2.63-2.68 (m, 2H), 6.04 (br. s, 1H), 7.29 (d, 1H), 7.44 (d, 1H), 7.57 (dd, 1H), 7.66 (s, 4H). |
| T60 | 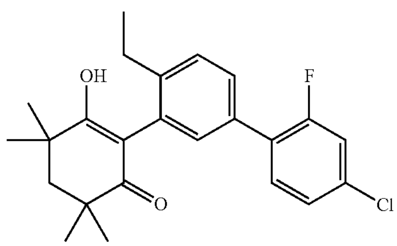 [SMILES: CCc1ccc(-c2ccc(Cl)cc2F)cc1C1=C(O)C(C)(C)CC(C)(C)C1=O] | δ 1.13 (t, 3H), 1.26 (d, 6H), 1.40 (d, 6H), 1.90 (d, 2H), 2.38-2.51 (m, 2H), 5.49 (br. s, 1H), 7.12-7.21 (m, 3H), 7.33-7.42 (m, 2H), 7.46-7.52 (m, 1H). |
| T61 | 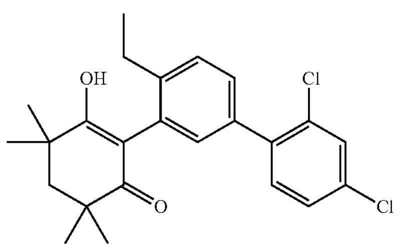 [SMILES: CCc1ccc(-c2ccc(Cl)cc2Cl)cc1C1=C(O)C(C)(C)CC(C)(C)C1=O] | δ 1.14 (t, 3H), 1.25 (d, 6H), 1.39 (d, 6H), 1.89 (d, 2H), 2.39-2.53 (m, 2H), 5.54 (s, 1H), 7.07 (s, 1H), 7.27-7.33 (m, 2H), 7.39 (s, 2H), 7.47 (d, 1H). |
| T62 | 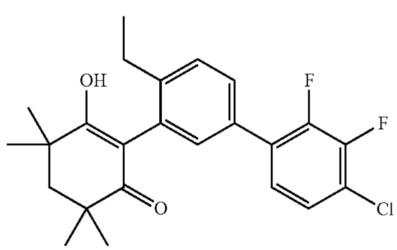 [SMILES: CCc1ccc(-c2ccc(Cl)c(F)c2F)cc1C1=C(O)C(C)(C)CC(C)(C)C1=O] | δ 1.13 (t, 3H), 1.27 (d, 6H), 1.40 (d, 6H), 1.80 (d, 2H), 2.38-2.52 (m, 2H), 5.51 (br. s, 1H), 7.12-7.24 (m, 3H), 7.42 (d, 1H), 7.47-7.52 (m, 1H). |
| T63 | 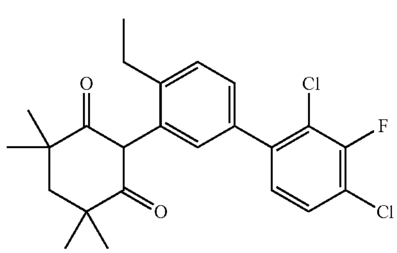 [SMILES: CCc1ccc(-c2ccc(Cl)c(F)c2Cl)cc1C1C(=O)C(C)(C)CC(C)(C)C1=O] | δ 1.15 (t, 3H), 1.26 (d, 6H), 1.39 (d, 6H), 1.89 (d, 2H), 2.40-2.53 (m, 2H), 5.50 (s, 1H), 7.08 (d, 1H), 7.13 (dd, 1H), 7.30-7.36 (m, 1H), 7.36-7.43 (m, 2H). |

TABLE A-continued

| Compound Number | Structure | ¹H nmr (CDCl₃ unless stated) or other physical data |
| --- | --- | --- |
| T64 | (structure) | δ 1.12 (t, 3H), 1.27 (d, 6H), 1.41 (d, 6H), 1.91 (d, 2H), 2.35-2.51 (m, 2H), 5.40 (s, 1H), 7.19 (d, 1H), 7.27-7.45 (m, 4H), 7.51 (dd, 1H). |
| T65 | (structure) | δ 1.13 (t, 3H), 1.27 (d, 6H), 1.41 (d, 6H), 1.92 (d, 2H), 2.38-2.54 (m, 2H), 5.41 (br. s, 1H), 7.20 (d, 1H), 7.43 (d, 1H), 7.51-7.56 (m, 2H), 7.67 (dd, 1H), 7.87 (d, 1H). |
| T66 | (structure) | δ 1.12 (t, 3H), 1.28 (d, 6H), 1.40 (d, 6H), 1.91 (d, 2H), 2.37-2.52 (m, 2H), 3.96 (s, 3H), 5.42 (s, 1H), 7.07-7.11 (m, 2H), 7.19 (d, 1H), 7.36-7.42 (m, 2H), 7.53 (dd, 1H). |
| T67 | (structure) | δ 1.12 (t, 3H), 1.27 (d, 6H), 1.41 (d, 6H), 1.91 (d, 2H), 2.37-2.51 (m, 2H), 5.42 (br. s, 1H), 7.19 (d, 1H), 7.37-7.42 (m, 2H), 7.47 (d, 1H), 7.50 (dd, 1H), 7.65 (d, 1H). |
| T68 | (structure) | δ 1.14 (t, 3H), 1.25 (d, 6H), 1.39 (d, 6H), 1.88 (d, 2H), 2.26 (s, 3H), 2.40-2.50 (m, 2H), 5.41 (s, 1H), 6.95 (d, 1H), 7.14-7.21 (m, 2H), 7.23-7.28 (m, 2H), 7.37 (d, 1H). |
| T69 | (structure) | δ 1.12 (t, 3H), 1.27 (d, 6H), 1.40 (d, 6H), 1.90 (d, 2H), 2.37-2.50 (m, 2H), 5.46 (br. s, 1H), 7.20 (d, 1H), 7.35-7.41 (m, 3H), 7.47-7.54 (m, 3H). |

Additional compounds in Table T1 below are prepared by similar methods using appropriate starting materials.
Table 1 covers 504 compounds of the type T-1

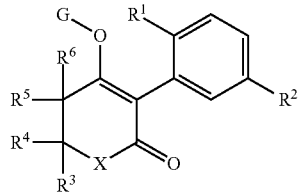

T-1 wherein G is hydrogen, X is CH₂, R³, R⁴, R⁵ and R⁶ are hydrogen, and R¹ and R² are as defined in Table 1.

| Compound Number | R¹ | R² |
|---|---|---|
| 1.001 | ethyl | phenyl |
| 1.002 | ethyl | 2-fluorophenyl |
| 1.003 | ethyl | 3-fluorophenyl |
| 1.004 | ethyl | 4-fluorophenyl |
| 1.005 | ethyl | 2-chlorophenyl |
| 1.006 | ethyl | 3-chlorophenyl |
| 1.007 | ethyl | 4-chlorophenyl |
| 1.008 | ethyl | 2-bromophenyl |
| 1.009 | ethyl | 3-bromophenyl |
| 1.010 | ethyl | 4-bromophenyl |
| 1.011 | ethyl | 2-methylphenyl |
| 1.012 | ethyl | 3-methylphenyl |
| 1.013 | ethyl | 4-methylphenyl |
| 1.014 | ethyl | 4-ethylphenyl |
| 1.015 | ethyl | 4-isopropylphenyl |
| 1.016 | ethyl | 4-isobutylphenyl |
| 1.017 | ethyl | 4-tert-butylphenyl |
| 1.018 | ethyl | 2-cyanophenyl |
| 1.019 | ethyl | 3-cyanophenyl |
| 1.020 | ethyl | 4-cyanophenyl |
| 1.021 | ethyl | 2-methoxyphenyl |
| 1.022 | ethyl | 3-methoxyphenyl |
| 1.023 | ethyl | 4-methoxyphenyl |
| 1.024 | ethyl | 2-trifluoromethylphenyl |
| 1.025 | ethyl | 3-trifluoromethylphenyl |
| 1.026 | ethyl | 4-trifluoromethylphenyl |
| 1.027 | ethyl | 4-trifluoromethoxyphenyl |
| 1.028 | ethyl | 4-difluoromethoxyphenyl |
| 1.029 | ethyl | 4-methylthiophenyl |
| 1.030 | ethyl | 4-methylsulfinylphenyl |
| 1.031 | ethyl | 4-methylsulfonylphenyl |
| 1.032 | ethyl | 4-trifluoromethylthiophenyl |
| 1.033 | ethyl | 4-trifluoromethylsulfinylphenyl |
| 1.034 | ethyl | 4-trifluoromethylsulfonylphenyl |
| 1.035 | ethyl | 2,3-difluorophenyl |
| 1.036 | ethyl | 2,4-difluorophenyl |
| 1.037 | ethyl | 2,5-difluorophenyl |
| 1.038 | ethyl | 2,6-difluorophenyl |
| 1.039 | ethyl | 3,4-difluorophenyl |
| 1.040 | ethyl | 3,5-difluorophenyl |
| 1.041 | ethyl | 2,3-dichlorophenyl |
| 1.042 | ethyl | 2,4-dichlorophenyl |
| 1.043 | ethyl | 2,5-dichlorophenyl |
| 1.044 | ethyl | 2,6-dichlorophenyl |
| 1.045 | ethyl | 3,4-dichlorophenyl |
| 1.046 | ethyl | 3,5-dichlorophenyl |
| 1.047 | ethyl | 2,3,4-trichlorophenyl |
| 1.048 | ethyl | 2,3,5-trichlorophenyl |
| 1.049 | ethyl | 2,3,6-trichlorophenyl |
| 1.050 | ethyl | 2,4,5-trichlorophenyl |
| 1.051 | ethyl | 2,4,6-trichlorophenyl |
| 1.052 | ethyl | 3,4,5-trichlorophenyl |
| 1.053 | ethyl | 2-chloro-3-fluorophenyl |
| 1.054 | ethyl | 2-chloro-4-fluorophenyl |
| 1.055 | ethyl | 2-chloro-4-fluorophenyl |
| 1.056 | ethyl | 2-chloro-4-fluorophenyl |
| 1.057 | ethyl | 3-chloro-2-fluorophenyl |
| 1.058 | ethyl | 3-chloro-4-fluorophenyl |
| 1.059 | ethyl | 3-chloro-5-fluorophenyl |
| 1.060 | ethyl | 4-chloro-2-fluorophenyl |
| 1.061 | ethyl | 4-chloro-3-fluorophenyl |
| 1.062 | ethyl | 5-chloro-2-fluorophenyl |
| 1.063 | ethyl | 4-chloro-2-methylphenyl |
| 1.064 | ethyl | 4-chloro-3-methylphenyl |
| 1.065 | ethyl | 4-chloro-2-trifluoromethylphenyl |
| 1.066 | ethyl | 4-chloro-3-trifluoromethylphenyl |
| 1.067 | ethyl | 4-chloro-2-cyanophenyl |
| 1.068 | ethyl | 4-chloro-3-cyanophenyl |
| 1.069 | ethyl | 4-chloro-2-methoxyphenyl |
| 1.070 | ethyl | 4-chloro-3-methoxyphenyl |
| 1.071 | ethyl | 4-fluoro-2-methylphenyl |
| 1.072 | ethyl | 4-fluoro-3-methylphenyl |
| 1.073 | ethyl | 4-fluoro-2-trifluoromethylphenyl |
| 1.074 | ethyl | 4-fluoro-3-trifluoromethylphenyl |
| 1.075 | ethyl | 2-fluoro-4-trifluoromethylphenyl |
| 1.076 | ethyl | 3-fluoro-4-trifluoromethylphenyl |
| 1.077 | ethyl | 2,3,4-trifluorophenyl |
| 1.078 | ethyl | 2,3,5-trifluorophenyl |
| 1.079 | ethyl | 2,3,6-trifluorophenyl |
| 1.080 | ethyl | 2,4,5-trifluorophenyl |
| 1.081 | ethyl | 2,4,6-trifluorophenyl |
| 1.082 | ethyl | 3,4,5-trifluorophenyl |
| 1.083 | ethyl | 3,4-dichloro-2-fluorophenyl |
| 1.084 | ethyl | 3,4-dichoro-5-fluorophenyl |
| 1.085 | ethyl | 4,5-dichloro-2-fluorophenyl |
| 1.086 | ethyl | 2-chloro-3,4-difluorophenyl |
| 1.087 | ethyl | 2-chloro-4,5-difluorophenyl |
| 1.088 | ethyl | 2-chloro-4,6-difluorophenyl |
| 1.089 | ethyl | 3-chloro-4,5-difluorophenyl |
| 1.090 | ethyl | 3,4-methylenedioxyphenyl |
| 1.091 | ethyl | benzo[1,3]diox-5-yl |
| 1.092 | ethyl | 2,3-dihydrobenzo[1,4]dioxin-6-yl |
| 1.093 | ethyl | 2-naphthyl |
| 1.094 | ethyl | 2-pyridyl |
| 1.095 | ethyl | 3-pyridyl |
| 1.096 | ethyl | 4-pyridyl |
| 1.097 | ethyl | 3-chloropyridin-2-yl |
| 1.098 | ethyl | 4-chloropyridin-2-yl |
| 1.099 | ethyl | 5-chloropyridin-2-yl |
| 1.100 | ethyl | 6-chloropyridin-2-yl |
| 1.101 | ethyl | 2-chloropyridin-3-yl |
| 1.102 | ethyl | 4-chloropyridin-3-yl |
| 1.103 | ethyl | 2-chloropyridin-4-yl |
| 1.104 | ethyl | 3-chloropyridin-4-yl |
| 1.105 | ethyl | 2-chloropyridin-5-yl |
| 1.106 | ethyl | 3-chloropyridin-5-yl |
| 1.107 | ethyl | 3-methylpyridin-2-yl |
| 1.108 | ethyl | 4-methylpyridin-2-yl |
| 1.109 | ethyl | 5-methylpyridin-2-yl |
| 1.110 | ethyl | 6-methylpyridin-2-yl |
| 1.111 | ethyl | 2-methylpyridin-3-yl |
| 1.112 | ethyl | 4-methylpyridin-3-yl |
| 1.113 | ethyl | 2-methylpyridin-4-yl |
| 1.114 | ethyl | 3-methylpyridin-4-yl |
| 1.115 | ethyl | 2-methylpyridin-5-yl |
| 1.116 | ethyl | 3-methylpyridinyl-5-yl |
| 1.117 | ethyl | 2-trifluoromethylpyridin-5-yl |
| 1.118 | ethyl | 3-trifluoromethylpyridin-5-yl |
| 1.119 | ethyl | 2,6-dichloropyridin-3-yl |
| 1.120 | ethyl | 2-chloro-4-methylpyridin-5-yl |
| 1.121 | ethyl | 6-chloro-2-methylpyridin-3-yl |
| 1.122 | ethyl | 5-chlorothiophen-2-yl |
| 1.123 | ethyl | 2-chlorothiophen-3-yl |
| 1.124 | ethyl | 2,5-dichlorothiophen-3-yl |
| 1.125 | ethyl | 1-methylpyrazol-4-yl |
| 1.126 | ethyl | 4-chloropyrazol-1-yl |
| 1.127 | cyclopropyl | phenyl |
| 1.128 | cyclopropyl | 2-fluorophenyl |
| 1.129 | cyclopropyl | 3-fluorophenyl |
| 1.130 | cyclopropyl | 4-fluorophenyl |
| 1.131 | cyclopropyl | 2-chlorophenyl |
| 1.132 | cyclopropyl | 3-chlorophenyl |

-continued

| Compound Number | R¹ | R² |
|---|---|---|
| 1.133 | cyclopropyl | 4-chlorophenyl |
| 1.134 | cyclopropyl | 2-bromophenyl |
| 1.135 | cyclopropyl | 3-bromophenyl |
| 1.136 | cyclopropyl | 4-bromophenyl |
| 1.137 | cyclopropyl | 2-methylphenyl |
| 1.138 | cyclopropyl | 3-methylphenyl |
| 1.139 | cyclopropyl | 4-methylphenyl |
| 1.140 | cyclopropyl | 4-ethylphenyl |
| 1.141 | cyclopropyl | 4-isopropylphenyl |
| 1.142 | cyclopropyl | 4-isobutylphenyl |
| 1.143 | cyclopropyl | 4-tert-butylphenyl |
| 1.144 | cyclopropyl | 2-cyanophenyl |
| 1.145 | cyclopropyl | 3-cyanophenyl |
| 1.146 | cyclopropyl | 4-cyanophenyl |
| 1.147 | cyclopropyl | 2-methoxyphenyl |
| 1.148 | cyclopropyl | 3-methoxyphenyl |
| 1.149 | cyclopropyl | 4-methoxyphenyl |
| 1.150 | cyclopropyl | 2-trifluoromethylphenyl |
| 1.151 | cyclopropyl | 3-trifluoromethylphenyl |
| 1.152 | cyclopropyl | 4-trifluoromethylphenyl |
| 1.153 | cyclopropyl | 4-trifluoromethoxyphenyl |
| 1.154 | cyclopropyl | 4-difluoromethoxyphenyl |
| 1.155 | cyclopropyl | 4-methylthiophenyl |
| 1.156 | cyclopropyl | 4-methylsulfinylphenyl |
| 1.157 | cyclopropyl | 4-methylsulfonylphenyl |
| 1.158 | cyclopropyl | 4-trifluoromethylthiophenyl |
| 1.159 | cyclopropyl | 4-trifluoromethylsulfinylphenyl |
| 1.160 | cyclopropyl | 4-trifluoromethylsulfonylphenyl |
| 1.161 | cyclopropyl | 2,3-difluorophenyl |
| 1.162 | cyclopropyl | 2,4-difluorophenyl |
| 1.163 | cyclopropyl | 2,5-difluorophenyl |
| 1.164 | cyclopropyl | 2,6-difluorophenyl |
| 1.165 | cyclopropyl | 3,4-difluorophenyl |
| 1.166 | cyclopropyl | 3,5-difluorophenyl |
| 1.167 | cyclopropyl | 2,3-dichlorophenyl |
| 1.168 | cyclopropyl | 2,4-dichlorophenyl |
| 1.169 | cyclopropyl | 2,5-dichlorophenyl |
| 1.170 | cyclopropyl | 2,6-dichlorophenyl |
| 1.171 | cyclopropyl | 3,4-dichlorophenyl |
| 1.172 | cyclopropyl | 3,5-dichlorophenyl |
| 1.173 | cyclopropyl | 2,3,4-trichlorophenyl |
| 1.174 | cyclopropyl | 2,3,5-trichlorophenyl |
| 1.175 | cyclopropyl | 2,3,6-trichlorophenyl |
| 1.176 | cyclopropyl | 2,4,5-trichlorophenyl |
| 1.177 | cyclopropyl | 2,4,6-trichlorophenyl |
| 1.178 | cyclopropyl | 3,4,5-trichlorophenyl |
| 1.179 | cyclopropyl | 2-chloro-3-fluorophenyl |
| 1.180 | cyclopropyl | 2-chloro-4-fluorophenyl |
| 1.181 | cyclopropyl | 2-chloro-4-fluorophenyl |
| 1.182 | cyclopropyl | 2-chloro-4-fluorophenyl |
| 1.183 | cyclopropyl | 3-chloro-2-fluorophenyl |
| 1.184 | cyclopropyl | 3-chloro-4-fluorophenyl |
| 1.185 | cyclopropyl | 3-chloro-5-fluorophenyl |
| 1.186 | cyclopropyl | 4-chloro-2-fluorophenyl |
| 1.187 | cyclopropyl | 4-chloro-3-fluorophenyl |
| 1.188 | cyclopropyl | 5-chloro-2-fluorophenyl |
| 1.189 | cyclopropyl | 4-chloro-2-methylphenyl |
| 1.190 | cyclopropyl | 4-chloro-3-methylphenyl |
| 1.191 | cyclopropyl | 4-chloro-2-trifluoromethylphenyl |
| 1.192 | cyclopropyl | 4-chloro-3-trifluoromethylphenyl |
| 1.193 | cyclopropyl | 4-chloro-2-cyanophenyl |
| 1.194 | cyclopropyl | 4-chloro-3-cyanophenyl |
| 1.195 | cyclopropyl | 4-chloro-2-methoxyphenyl |
| 1.196 | cyclopropyl | 4-chloro-3-methoxyphenyl |
| 1.197 | cyclopropyl | 4-fluoro-2-methylphenyl |
| 1.198 | cyclopropyl | 4-fluoro-3-methylphenyl |
| 1.199 | cyclopropyl | 4-fluoro-2-trifluoromethylphenyl |
| 1.200 | cyclopropyl | 4-fluoro-3-trifluoromethylphenyl |
| 1.201 | cyclopropyl | 2-fluoro-4-trifluoromethylphenyl |
| 1.202 | cyclopropyl | 3-fluoro-4-trifluoromethylphenyl |
| 1.203 | cyclopropyl | 2,3,4-trifluorophenyl |
| 1.204 | cyclopropyl | 2,3,5-trifluorophenyl |
| 1.205 | cyclopropyl | 2,3,6-trifluorophenyl |
| 1.206 | cyclopropyl | 2,4,5-trifluorophenyl |
| 1.207 | cyclopropyl | 2,4,6-trifluorophenyl |
| 1.208 | cyclopropyl | 3,4,5-trifluorophenyl |
| 1.209 | cyclopropyl | 3,4-dichloro-2-fluorophenyl |
| 1.210 | cyclopropyl | 3,4-dichoro-5-fluorophenyl |
| 1.211 | cyclopropyl | 4,5-dichloro-2-fluorophenyl |
| 1.212 | cyclopropyl | 2-chloro-3,4-difluorophenyl |
| 1.213 | cyclopropyl | 2-chloro-4,5-difluorophenyl |
| 1.214 | cyclopropyl | 2-chloro-4,6-difluorophenyl |
| 1.215 | cyclopropyl | 3-chloro-4,5-difluorophenyl |
| 1.216 | cyclopropyl | 3,4-methylenedioxyphenyl |
| 1.217 | cyclopropyl | benzo[1,3]diox-5-yl |
| 1.218 | cyclopropyl | 2,3-dihydrobenzo[1,4]dioxin-6-yl |
| 1.219 | cyclopropyl | 2-naphthyl |
| 1.220 | cyclopropyl | 2-pyridyl |
| 1.221 | cyclopropyl | 3-pyridyl |
| 1.222 | cyclopropyl | 4-pyridyl |
| 1.223 | cyclopropyl | 3-chloropyridin-2-yl |
| 1.224 | cyclopropyl | 4-chloropyridin-2-yl |
| 1.225 | cyclopropyl | 5-chloropyridin-2-yl |
| 1.226 | cyclopropyl | 6-chloropyridin-2-yl |
| 1.227 | cyclopropyl | 2-chloropyridin-3-yl |
| 1.228 | cyclopropyl | 4-chloropyridin-3-yl |
| 1.229 | cyclopropyl | 2-chloropyridin-4-yl |
| 1.230 | cyclopropyl | 3-chloropyridin-4-yl |
| 1.231 | cyclopropyl | 2-chloropyridin-5-yl |
| 1.232 | cyclopropyl | 3-chloropyridin-5-yl |
| 1.233 | cyclopropyl | 3-methylpyridin-2-yl |
| 1.234 | cyclopropyl | 4-methylpyridin-2-yl |
| 1.235 | cyclopropyl | 5-methylpyridin-2-yl |
| 1.236 | cyclopropyl | 6-methylpyridin-2-yl |
| 1.237 | cyclopropyl | 2-methylpyridin-3-yl |
| 1.238 | cyclopropyl | 4-methylpyridin-3-yl |
| 1.239 | cyclopropyl | 2-methylpyridin-4-yl |
| 1.240 | cyclopropyl | 3-methylpyridin-4-yl |
| 1.241 | cyclopropyl | 2-methylpyridin-5-yl |
| 1.242 | cyclopropyl | 3-methylpyridinyl-5-yl |
| 1.243 | cyclopropyl | 2-trifluoromethylpyridin-5-yl |
| 1.244 | cyclopropyl | 3-trifluoromethylpyridin-5-yl |
| 1.245 | cyclopropyl | 2,6-dichloropyridin-3-yl |
| 1.246 | cyclopropyl | 2-chloro-4-methylpyridin-5-yl |
| 1.247 | cyclopropyl | 6-chloro-2-methylpyridin-3-yl |
| 1.248 | cyclopropyl | 5-chlorothiophen-2-yl |
| 1.249 | cyclopropyl | 2-chlorothiophen-3-yl |
| 1.250 | cyclopropyl | 2,5-dichlorothiophen-3-yl |
| 1.251 | cyclopropyl | 1-methylpyrazol-4-yl |
| 1.252 | cyclopropyl | 4-chloropyrazol-1-yl |
| 1.253 | difluoromethoxy | phenyl |
| 1.254 | difluoromethoxy | 2-fluorophenyl |
| 1.255 | difluoromethoxy | 3-fluorophenyl |
| 1.256 | difluoromethoxy | 4-fluorophenyl |
| 1.257 | difluoromethoxy | 2-chlorophenyl |
| 1.258 | difluoromethoxy | 3-chlorophenyl |
| 1.259 | difluoromethoxy | 4-chlorophenyl |
| 1.260 | difluoromethoxy | 2-bromophenyl |
| 1.261 | difluoromethoxy | 3-bromophenyl |
| 1.262 | difluoromethoxy | 4-bromophenyl |
| 1.263 | difluoromethoxy | 2-methylphenyl |
| 1.264 | difluoromethoxy | 3-methylphenyl |
| 1.265 | difluoromethoxy | 4-methylphenyl |
| 1.266 | difluoromethoxy | 4-ethylphenyl |
| 1.267 | difluoromethoxy | 4-isopropylphenyl |
| 1.268 | difluoromethoxy | 4-isobutylphenyl |
| 1.269 | difluoromethoxy | 4-tert-butylphenyl |
| 1.270 | difluoromethoxy | 2-cyanophenyl |
| 1.271 | difluoromethoxy | 3-cyanophenyl |
| 1.272 | difluoromethoxy | 4-cyanophenyl |
| 1.273 | difluoromethoxy | 2-methoxyphenyl |
| 1.274 | difluoromethoxy | 3-methoxyphenyl |
| 1.275 | difluoromethoxy | 4-methoxyphenyl |
| 1.276 | difluoromethoxy | 2-trifluoromethylphenyl |
| 1.277 | difluoromethoxy | 3-trifluoromethylphenyl |
| 1.278 | difluoromethoxy | 4-trifluoromethylphenyl |
| 1.279 | difluoromethoxy | 4-trifluoromethoxyphenyl |
| 1.280 | difluoromethoxy | 4-difluoromethoxyphenyl |
| 1.281 | difluoromethoxy | 4-methylthiophenyl |
| 1.282 | difluoromethoxy | 4-methylsulfinylphenyl |
| 1.283 | difluoromethoxy | 4-methylsulfonylphenyl |
| 1.284 | difluoromethoxy | 4-trifluoromethylthiophenyl |
| 1.285 | difluoromethoxy | 4-trifluoromethylsulfinylphenyl |
| 1.286 | difluoromethoxy | 4-trifluoromethylsulfonylphenyl |

-continued

| Compound Number | R¹ | R² |
|---|---|---|
| 1.287 | difluoromethoxy | 2,3-difluorophenyl |
| 1.288 | difluoromethoxy | 2,4-difluorophenyl |
| 1.289 | difluoromethoxy | 2,5-difluorophenyl |
| 1.290 | difluoromethoxy | 2,6-difluorophenyl |
| 1.291 | difluoromethoxy | 3,4-difluorophenyl |
| 1.292 | difluoromethoxy | 3,5-difluorophenyl |
| 1.293 | difluoromethoxy | 2,3-dichlorophenyl |
| 1.294 | difluoromethoxy | 2,4-dichlorophenyl |
| 1.295 | difluoromethoxy | 2,5-dichlorophenyl |
| 1.296 | difluoromethoxy | 2,6-dichlorophenyl |
| 1.297 | difluoromethoxy | 3,4-dichlorophenyl |
| 1.298 | difluoromethoxy | 3,5-dichlorophenyl |
| 1.299 | difluoromethoxy | 2,3,4-trichlorophenyl |
| 1.300 | difluoromethoxy | 2,3,5-trichlorophenyl |
| 1.301 | difluoromethoxy | 2,3,6-trichlorophenyl |
| 1.302 | difluoromethoxy | 2,4,5-trichlorophenyl |
| 1.303 | difluoromethoxy | 2,4,6-trichlorophenyl |
| 1.304 | difluoromethoxy | 3,4,5-trichlorophenyl |
| 1.305 | difluoromethoxy | 2-chloro-3-fluorophenyl |
| 1.306 | difluoromethoxy | 2-chloro-4-fluorophenyl |
| 1.307 | difluoromethoxy | 2-chloro-4-fluorophenyl |
| 1.308 | difluoromethoxy | 2-chloro-4-fluorophenyl |
| 1.309 | difluoromethoxy | 3-chloro-2-fluorophenyl |
| 1.310 | difluoromethoxy | 3-chloro-4-fluorophenyl |
| 1.311 | difluoromethoxy | 3-chloro-5-fluorophenyl |
| 1.312 | difluoromethoxy | 4-chloro-2-fluorophenyl |
| 1.313 | difluoromethoxy | 4-chloro-3-fluorophenyl |
| 1.314 | difluoromethoxy | 5-chloro-2-fluorophenyl |
| 1.315 | difluoromethoxy | 4-chloro-2-methylphenyl |
| 1.316 | difluoromethoxy | 4-chloro-3-methylphenyl |
| 1.317 | difluoromethoxy | 4-chloro-2-trifluoromethylphenyl |
| 1.318 | difluoromethoxy | 4-chloro-3-trifluoromethylphenyl |
| 1.319 | difluoromethoxy | 4-chloro-2-cyanophenyl |
| 1.320 | difluoromethoxy | 4-chloro-3-cyanophenyl |
| 1.321 | difluoromethoxy | 4-chloro-2-methoxyphenyl |
| 1.322 | difluoromethoxy | 4-chloro-3-methoxyphenyl |
| 1.323 | difluoromethoxy | 4-fluoro-2-methylphenyl |
| 1.324 | difluoromethoxy | 4-fluoro-3-methylphenyl |
| 1.325 | difluoromethoxy | 4-fluoro-2-trifluoromethylphenyl |
| 1.326 | difluoromethoxy | 4-fluoro-3-trifluoromethylphenyl |
| 1.327 | difluoromethoxy | 2-fluoro-4-trifluoromethylphenyl |
| 1.328 | difluoromethoxy | 3-fluoro-4-trifluoromethylphenyl |
| 1.329 | difluoromethoxy | 2,3,4-trifluorophenyl |
| 1.330 | difluoromethoxy | 2,3,5-trifluorophenyl |
| 1.331 | difluoromethoxy | 2,3,6-trifluorophenyl |
| 1.332 | difluoromethoxy | 2,4,5-trifluorophenyl |
| 1.333 | difluoromethoxy | 2,4,6-trifluorophenyl |
| 1.337 | difluoromethoxy | 3,4,5-trifluorophenyl |
| 1.335 | difluoromethoxy | 3,4-dichloro-2-fluorophenyl |
| 1.336 | difluoromethoxy | 3,4-dichoro-5-fluorophenyl |
| 1.337 | difluoromethoxy | 4,5-dichloro-2-fluorophenyl |
| 1.338 | difluoromethoxy | 2-chloro-3,4-difluorophenyl |
| 1.339 | difluoromethoxy | 2-chloro-4,5-difluorophenyl |
| 1.340 | difluoromethoxy | 2-chloro-4,6-difluorophenyl |
| 1.341 | difluoromethoxy | 3-chloro-4,5-difluorophenyl |
| 1.342 | difluoromethoxy | 3,4-methylenedioxyphenyl |
| 1.343 | difluoromethoxy | benzo[1,3]diox-5-yl |
| 1.344 | difluoromethoxy | 2,3-dihydrobenzo[1,4]dioxin-6-yl |
| 1.345 | difluoromethoxy | 2-naphthyl |
| 1.346 | difluoromethoxy | 2-pyridyl |
| 1.347 | difluoromethoxy | 3-pyridyl |
| 1.348 | difluoromethoxy | 4-pyridyl |
| 1.349 | difluoromethoxy | 3-chloropyridin-2-yl |
| 1.350 | difluoromethoxy | 4-chloropyridin-2-yl |
| 1.351 | difluoromethoxy | 5-chloropyridin-2-yl |
| 1.352 | difluoromethoxy | 6-chloropyridin-2-yl |
| 1.353 | difluoromethoxy | 2-chloropyridin-3-yl |
| 1.354 | difluoromethoxy | 4-chloropyridin-3-yl |
| 1.355 | difluoromethoxy | 2-chloropyridin-4-yl |
| 1.356 | difluoromethoxy | 3-chloropyridin-4-yl |
| 1.357 | difluoromethoxy | 2-chloropyridin-5-yl |
| 1.358 | difluoromethoxy | 3-chloropyridin-5-yl |
| 1.359 | difluoromethoxy | 3-methylpyridin-2-yl |
| 1.360 | difluoromethoxy | 4-methylpyridin-2-yl |
| 1.361 | difluoromethoxy | 5-methylpyridin-2-yl |
| 1.362 | difluoromethoxy | 6-methylpyridin-2-yl |
| 1.363 | difluoromethoxy | 2-methylpyridin-3-yl |
| 1.364 | difluoromethoxy | 4-methylpyridin-3-yl |
| 1.365 | difluoromethoxy | 2-methylpyridin-4-yl |
| 1.366 | difluoromethoxy | 3-methylpyridin-4-yl |
| 1.367 | difluoromethoxy | 2-methylpyridin-5-yl |
| 1.368 | difluoromethoxy | 3-methylpyridinyl-5-yl |
| 1.369 | difluoromethoxy | 2-trifluoromethylpyridin-5-yl |
| 1.370 | difluoromethoxy | 3-trifluoromethylpyridin-5-yl |
| 1.371 | difluoromethoxy | 2,6-dichloropyridin-3-yl |
| 1.372 | difluoromethoxy | 2-chloro-4-methylpyridin-5-yl |
| 1.373 | difluoromethoxy | 6-chloro-2-methylpyridin-3-yl |
| 1.374 | difluoromethoxy | 5-chlorothiophen-2-yl |
| 1.375 | difluoromethoxy | 2-chlorothiophen-3-yl |
| 1.376 | difluoromethoxy | 2,5-dichlorothiophen-3-yl |
| 1.377 | difluoromethoxy | 1-methylpyrazol-4-yl |
| 1.378 | difluoromethoxy | 4-chloropyrazol-1-yl |
| 1.379 | trifluoromethoxy | phenyl |
| 1.380 | trifluoromethoxy | 2-fluorophenyl |
| 1.381 | trifluoromethoxy | 3-fluorophenyl |
| 1.382 | trifluoromethoxy | 4-fluorophenyl |
| 1.383 | trifluoromethoxy | 2-chlorophenyl |
| 1.384 | trifluoromethoxy | 3-chlorophenyl |
| 1.385 | trifluoromethoxy | 4-chlorophenyl |
| 1.386 | trifluoromethoxy | 2-bromophenyl |
| 1.387 | trifluoromethoxy | 3-bromophenyl |
| 1.388 | trifluoromethoxy | 4-bromophenyl |
| 1.389 | trifluoromethoxy | 2-methylphenyl |
| 1.390 | trifluoromethoxy | 3-methylphenyl |
| 1.391 | trifluoromethoxy | 4-methylphenyl |
| 1.392 | trifluoromethoxy | 4-ethylphenyl |
| 1.393 | trifluoromethoxy | 4-isopropylphenyl |
| 1.394 | trifluoromethoxy | 4-isobutylphenyl |
| 1.395 | trifluoromethoxy | 4-tert-butylphenyl |
| 1.396 | trifluoromethoxy | 2-cyanophenyl |
| 1.397 | trifluoromethoxy | 3-cyanophenyl |
| 1.398 | trifluoromethoxy | 4-cyanophenyl |
| 1.399 | trifluoromethoxy | 2-methoxyphenyl |
| 1.400 | trifluoromethoxy | 3-methoxyphenyl |
| 1.401 | trifluoromethoxy | 4-methoxyphenyl |
| 1.402 | trifluoromethoxy | 2-trifluoromethylphenyl |
| 1.403 | trifluoromethoxy | 3-trifluoromethylphenyl |
| 1.404 | trifluoromethoxy | 4-trifluoromethylphenyl |
| 1.405 | trifluoromethoxy | 4-trifluoromethoxyphenyl |
| 1.406 | trifluoromethoxy | 4-difluoromethoxyphenyl |
| 1.407 | trifluoromethoxy | 4-methylthiophenyl |
| 1.408 | trifluoromethoxy | 4-methylsulfinylphenyl |
| 1.409 | trifluoromethoxy | 4-methylsulfonylphenyl |
| 1.410 | trifluoromethoxy | 4-trifluoromethylthiophenyl |
| 1.411 | trifluoromethoxy | 4-trifluoromethylsulfinylphenyl |
| 1.412 | trifluoromethoxy | 4-trifluoromethylsulfonylphenyl |
| 1.413 | trifluoromethoxy | 2,3-difluorophenyl |
| 1.414 | trifluoromethoxy | 2,4-difluorophenyl |
| 1.415 | trifluoromethoxy | 2,5-difluorophenyl |
| 1.416 | trifluoromethoxy | 2,6-difluorophenyl |
| 1.417 | trifluoromethoxy | 3,4-difluorophenyl |
| 1.418 | trifluoromethoxy | 3,5-difluorophenyl |
| 1.419 | trifluoromethoxy | 2,3-dichlorophenyl |
| 1.420 | trifluoromethoxy | 2,4-dichlorophenyl |
| 1.421 | trifluoromethoxy | 2,5-dichlorophenyl |
| 1.422 | trifluoromethoxy | 2,6-dichlorophenyl |
| 1.423 | trifluoromethoxy | 3,4-dichlorophenyl |
| 1.424 | trifluoromethoxy | 3,5-dichlorophenyl |
| 1.425 | trifluoromethoxy | 2,3,4-trichlorophenyl |
| 1.426 | trifluoromethoxy | 2,3,5-trichlorophenyl |
| 1.427 | trifluoromethoxy | 2,3,6-trichlorophenyl |
| 1.428 | trifluoromethoxy | 2,4,5-trichlorophenyl |
| 1.429 | trifluoromethoxy | 2,4,6-trichlorophenyl |
| 1.430 | trifluoromethoxy | 3,4,5-trichlorophenyl |
| 1.431 | trifluoromethoxy | 2-chloro-3-fluorophenyl |
| 1.432 | trifluoromethoxy | 2-chloro-4-fluorophenyl |
| 1.433 | trifluoromethoxy | 2-chloro-4-fluorophenyl |
| 1.434 | trifluoromethoxy | 2-chloro-4-fluorophenyl |
| 1.435 | trifluoromethoxy | 3-chloro-2-fluorophenyl |
| 1.436 | trifluoromethoxy | 3-chloro-4-fluorophenyl |
| 1.437 | trifluoromethoxy | 3-chloro-5-fluorophenyl |
| 1.438 | trifluoromethoxy | 4-chloro-2-fluorophenyl |
| 1.439 | trifluoromethoxy | 4-chloro-3-fluorophenyl |
| 1.440 | trifluoromethoxy | 5-chloro-2-fluorophenyl |

| Compound Number | R¹ | R² |
|---|---|---|
| 1.441 | trifluoromethoxy | 4-chloro-2-methylphenyl |
| 1.442 | trifluoromethoxy | 4-chloro-3-methylphenyl |
| 1.443 | trifluoromethoxy | 4-chloro-2-trifluoromethylphenyl |
| 1.444 | trifluoromethoxy | 4-chloro-3-trifluoromethylphenyl |
| 1.445 | trifluoromethoxy | 4-chloro-2-cyanophenyl |
| 1.446 | trifluoromethoxy | 4-chloro-3-cyanophenyl |
| 1.447 | trifluoromethoxy | 4-chloro-2-methoxyphenyl |
| 1.448 | trifluoromethoxy | 4-chloro-3-methoxyphenyl |
| 1.449 | trifluoromethoxy | 4-fluoro-2-methylphenyl |
| 1.450 | trifluoromethoxy | 4-fluoro-3-methylphenyl |
| 1.451 | trifluoromethoxy | 4-fluoro-2-trifluoromethylphenyl |
| 1.452 | trifluoromethoxy | 4-fluoro-3-trifluoromethylphenyl |
| 1.453 | trifluoromethoxy | 2-fluoro-4-trifluoromethylphenyl |
| 1.454 | trifluoromethoxy | 3-fluoro-4-trifluoromethylphenyl |
| 1.455 | trifluoromethoxy | 2,3,4-trifluorophenyl |
| 1.456 | trifluoromethoxy | 2,3,5-trifluorophenyl |
| 1.457 | trifluoromethoxy | 2,3,6-trifluorophenyl |
| 1.458 | trifluoromethoxy | 2,4,5-trifluorophenyl |
| 1.459 | trifluoromethoxy | 2,4,6-trifluorophenyl |
| 1.460 | trifluoromethoxy | 3,4,5-trifluorophenyl |
| 1.461 | trifluoromethoxy | 3,4-dichloro-2-fluorophenyl |
| 1.462 | trifluoromethoxy | 3,4-dichoro-5-fluorophenyl |
| 1.463 | trifluoromethoxy | 4,5-dichloro-2-fluorophenyl |
| 1.464 | trifluoromethoxy | 2-chloro-3,4-difluorophenyl |
| 1.465 | trifluoromethoxy | 2-chloro-4,5-difluorophenyl |
| 1.466 | trifluoromethoxy | 2-chloro-4,6-difluorophenyl |
| 1.467 | trifluoromethoxy | 3-chloro-4,5-difluorophenyl |
| 1.468 | trifluoromethoxy | 3,4-methylenedioxyphenyl |
| 1.469 | trifluoromethoxy | benzo[1,3]diox-5-yl |
| 1.470 | trifluoromethoxy | 2,3-dihydrobenzo[1,4]dioxin-6-yl |
| 1.471 | trifluoromethoxy | 2-naphthyl |
| 1.472 | trifluoromethoxy | 2-pyridyl |
| 1.473 | trifluoromethoxy | 3-pyridyl |
| 1.474 | trifluoromethoxy | 4-pyridyl |
| 1.475 | trifluoromethoxy | 3-chloropyridin-2-yl |
| 1.476 | trifluoromethoxy | 4-chloropyridin-2-yl |
| 1.477 | trifluoromethoxy | 5-chloropyridin-2-yl |
| 1.478 | trifluoromethoxy | 6-chloropyridin-2-yl |
| 1.479 | trifluoromethoxy | 2-chloropyridin-3-yl |
| 1.480 | trifluoromethoxy | 4-chloropyridin-3-yl |
| 1.481 | trifluoromethoxy | 2-chloropyridin-4-yl |
| 1.482 | trifluoromethoxy | 3-chloropyridin-4-yl |
| 1.483 | trifluoromethoxy | 2-chloropyridin-5-yl |
| 1.484 | trifluoromethoxy | 3-chloropyridin-5-yl |
| 1.485 | trifluoromethoxy | 3-methylpyridin-2-yl |
| 1.486 | trifluoromethoxy | 4-methylpyridin-2-yl |
| 1.487 | trifluoromethoxy | 5-methylpyridin-2-yl |
| 1.488 | trifluoromethoxy | 6-methylpyridin-2-yl |
| 1.489 | trifluoromethoxy | 2-methylpyridin-3-yl |
| 1.490 | trifluoromethoxy | 4-methylpyridin-3-yl |
| 1.491 | trifluoromethoxy | 2-methylpyridin-4-yl |
| 1.492 | trifluoromethoxy | 3-methylpyridin-4-yl |
| 1.493 | trifluoromethoxy | 2-methylpyridin-5-yl |
| 1.494 | trifluoromethoxy | 3-methylpyridinyl-5-yl |
| 1.495 | trifluoromethoxy | 2-trifluoromethylpyridin-5-yl |
| 1.496 | trifluoromethoxy | 3-trifluoromethylpyridin-5-yl |
| 1.497 | trifluoromethoxy | 2,6-dichloropyridin-3-yl |
| 1.498 | trifluoromethoxy | 2-chloro-4-methylpyridin-5-yl |
| 1.499 | trifluoromethoxy | 6-chloro-2-methylpyridin-3-yl |
| 1.500 | trifluoromethoxy | 5-chlorothiophen-2-yl |
| 1.501 | trifluoromethoxy | 2-chlorothiophen-3-yl |
| 1.502 | trifluoromethoxy | 2,5-dichlorothiophen-3-yl |
| 1.503 | trifluoromethoxy | 1-methylpyrazol-4-yl |
| 1.504 | trifluoromethoxy | 4-chloropyrazol-1-yl |

Table 2 covers 504 compounds of the type T-1, wherein G is hydrogen, X is $CH_2$, $R^3$, $R^4$ and $R^5$ are hydrogen, $R^6$ is methyl, and $R^1$ and $R^2$ are as defined in Table 1.

Table 3 covers 504 compounds of the type T-1, wherein G is hydrogen, X is $CH_2$, $R^3$ and $R^4$ are hydrogen, $R^5$ and $R^6$ are methyl, and $R^1$ and $R^2$ are as defined in Table 1.

Table 4 covers 504 compounds of the type T-1, wherein G is hydrogen, X is $CH_2$, $R^3$, $R^5$ and $R^6$ are hydrogen, $R^4$ is methyl, and $R^1$ and $R^2$ are as defined in Table 1.

Table 5 covers 504 compounds of the type T-1, wherein G is hydrogen, X is $CH_2$, $R^3$ and $R^4$ are methyl, $R^5$ and $R^6$ are hydrogen, and $R^1$ and $R^2$ are as defined in Table 1.

Table 6 covers 504 compounds of the type T-1, wherein G is hydrogen, X is $C(CH_3)_2$, $R^3$ and $R^4$ are hydrogen, $R^5$ and $R^6$ are methyl, and $R^1$ and $R^2$ are as defined in Table 1.

Table 7 covers 504 compounds of the type T-2

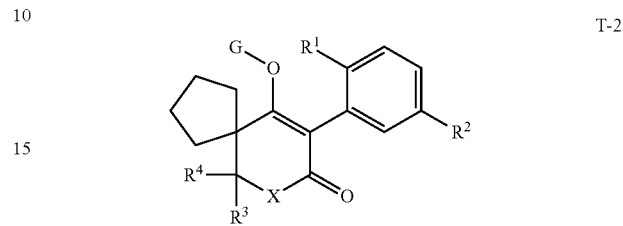

T-2 wherein G is hydrogen, X is $CH_2$, $R^3$ and $R^4$ are hydrogen, and $R^1$ and $R^2$ are as defined in Table 1.

Table 8 covers 504 compounds of the type T-3

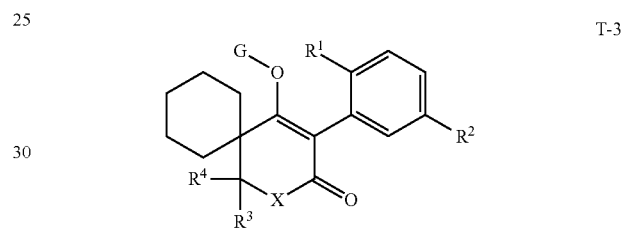

T-3 wherein G is hydrogen, X is $CH_2$, $R^3$ and $R^4$ are hydrogen, and $R^1$ and $R^2$ are as defined in Table 1.

Table 9 covers 504 compounds of the type T-4

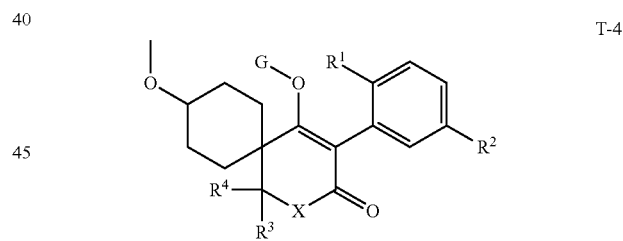

T-4 wherein G is hydrogen, X is $CH_2$, $R^3$ and $R^4$ are hydrogen, and $R^1$ and $R^2$ are as defined in Table 1.

Table 10 covers 504 compounds of the type T-5

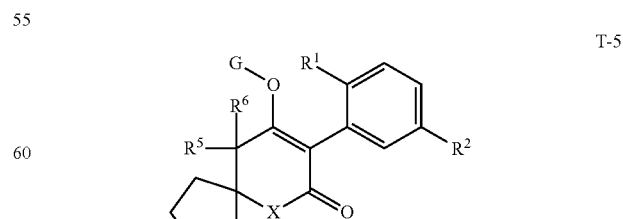

T-5 wherein G is hydrogen, X is $CH_2$, $R^5$ and $R^6$ are hydrogen, and $R^1$ and $R^2$ are as defined in Table 1.

Table 11 covers 504 compounds of the type T-6

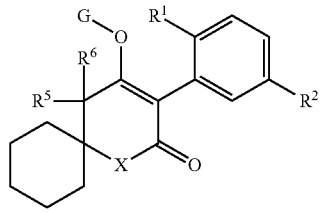

wherein G is hydrogen, X is $CH_2$, $R^5$ and $R^6$ are hydrogen, and $R^1$ and $R^2$ are as defined in Table 1.

Table 12 covers 504 compounds of the type T-1, wherein G is hydrogen, X is O, $R^3$, $R^4$, $R^5$ and $R^6$ are hydrogen, and $R^1$ and $R^2$ are as defined in Table 1.

Table 13 covers 504 compounds of the type T-1, wherein G is hydrogen, X is O, $R^3$, $R^4$ and $R^5$ are hydrogen, $R^6$ is methyl, and $R^1$ and $R^2$ are as defined in Table 1.

Table 14 covers 504 compounds of the type T-1, wherein G is hydrogen, X is O, $R^3$ and $R^4$ are hydrogen, $R^5$ and $R^6$ are methyl, and $R^1$ and $R^2$ are as defined in Table 1.

Table 15 covers 504 compounds of the type T-1, wherein G is hydrogen, X is O, $R^3$, $R^5$ and $R^6$ are hydrogen, $R^4$ is methyl, and $R^1$ and $R^2$ are as defined in Table 1.

Table 16 covers 504 compounds of the type T-1, wherein G is hydrogen, X is O, $R^3$ and $R^4$ are methyl, $R^5$ and $R^6$ are hydrogen, and $R^1$ and $R^2$ are as defined in Table 1.

Table 17 covers 504 compounds of the type T-1, wherein G is hydrogen, X is O, $R^3$, $R^4$ and $R^5$ are methyl, $R^6$ is hydrogen, and $R^1$ and $R^2$ are as defined in Table 1.

Table 18 covers 504 compounds of the type T-1, wherein G is hydrogen, X is O, $R^3$, $R^4$, $R^5$ and $R^6$ are methyl, and $R^1$ and $R^2$ are as defined in Table 1.

Table 19 covers 504 compounds of the type T-2, wherein G is hydrogen, X is O, $R^3$ and $R^4$ are hydrogen, and $R^1$ and $R^2$ are as defined in Table 1.

Table 20 covers 504 compounds of the type T-3, wherein G is hydrogen, X is O, $R^3$ and $R^4$ are hydrogen, and $R^1$ and $R^2$ are as defined in Table 1.

Table 21 covers 504 compounds of the type T-4, wherein G is hydrogen, X is O, $R^3$ and $R^4$ are hydrogen, and $R^1$ and $R^2$ are as defined in Table 1.

Table 22 covers 504 compounds of the type T-5, wherein G is hydrogen, X is O, $R^5$ and $R^6$ are hydrogen, and $R^1$ and $R^2$ are as defined in Table 1.

Table 23 covers 504 compounds of the type T-6, wherein G is hydrogen, X is O, $R^5$ and $R^6$ are hydrogen, and $R^1$ and $R^2$ are as defined in Table 1.

Table 24 covers 504 compounds of the type T-7, wherein G is hydrogen, X is O, $R^3$ is methyl, $R^6$ is hydrogen, and $R^1$ and $R^2$ are as defined in Table 1.

Table 25 covers 504 compounds of the type T-7, wherein G is hydrogen, X is O, $R^3$ is hydrogen, $R^6$ is methyl, and $R^1$ and $R^2$ are as defined in Table 1.

Table 26 covers 504 compounds of the type T-7, wherein G is hydrogen, X is O, $R^3$ and $R^6$ are methyl, and $R^1$ and $R^2$ are as defined in Table 1.

BIOLOGICAL EXAMPLES

Example A

Seeds of a variety of test species were sown in standard soil in pots. After cultivation for one day (pre-emergence) or after 10 days cultivation (post-emergence) under controlled conditions in a glasshouse, the plants were sprayed with an aqueous spray solution derived from the formulation of the technical active ingredient of formula I in 0.6 ml acetone and 45 ml formulation solution containing 10.6% Emulsogen EL (Registry number 61791-12-6), 42.2% N-methylpyrrolidone, 42.2% dipropylene glycol monomethyl ether (Registry number 34590-94-8) and 0.2% X-77 (Registry number 11097-66-8). The test plants were then grown in a greenhouse under optimum conditions until, 15 days later for post-emergence and 20 days for pre-emergence, the test was evaluated (100=total damage to plant; 0=no damage to plant).

The compound of Example 1-8-a-1 from WO99/48869 was also sprayed for comparison.

Test Plants:
*Alopecurus myosuroides* (ALOMY), *Avena fatua* (AVEFA), *Lolium perenne* (LOLPE), *Setaria faberi* (SETFA), *Digitaria sanguinalis* (DIGSA), *Echinochloa crus-galli* (ECHCG) and *Sorghum bicolor* (SORVU)

Pre-Emergence Activity

| Compound | Rate g/ha | ALOMY | AVEFA | LOLPE | SETFA | DIGSA | ECHCG |
|---|---|---|---|---|---|---|---|
| Example 1-8-a-1 from WO99/48869 | 250 | 20 | 0 | 20 | 30 | 70 | 90 |
| Compound T1 | 250 | 60 | 70 | 90 | 100 | — | 90 |

| Compound | Rate g/ha | ALOMY | AVEFA | LOLPE | SETFA | DIGSA | ECHCG |
|---|---|---|---|---|---|---|---|
| 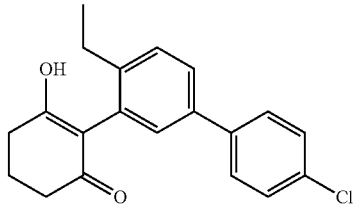 [SMILES: CCc1ccc(-c2ccc(Cl)cc2)cc1C1=C(O)CCCC1=O] Compound T2 | 250 | 60 | 70 | 70 | 80 | 80 | 100 |
| 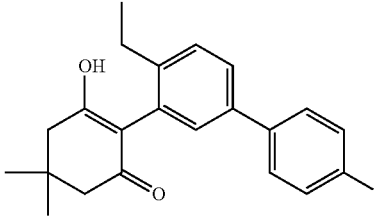 Compound T3 | 250 | 90 | 50 | 100 | 80 | 100 | 100 |
Post-Emergence Activity
| Compound | Rate g/ha | ALOMY | AVEFA | SORVU | SETFA | DIGSA | ECHCG |
|---|---|---|---|---|---|---|---|
| 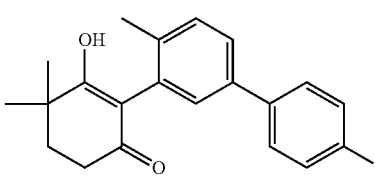 Example 1-8-a-1 from WO99/48869 | 15 | 0 | 0 | 0 | 20 | 20 | 70 |
| 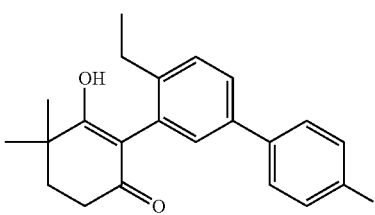 Compound T1 | 15 | 0 | 10 | 50 | 90 | 80 | 70 |
| 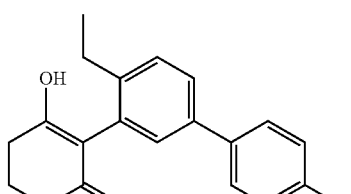 Compound T2 | 15 | 0 | 0 | 70 | 80 | 80 | 90 |

| Compound | Rate g/ha | ALOMY | AVEFA | SORVU | SETFA | DIGSA | ECHCG |
|---|---|---|---|---|---|---|---|
| 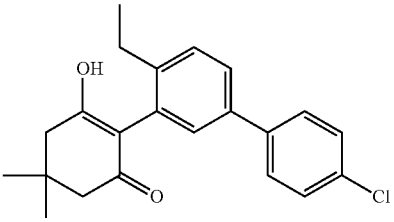 [SMILES: CCc1ccc(-c2ccc(Cl)cc2)cc1C1=C(O)CC(C)(C)CC1=O] Compound T3 | 15 | 50 | 20 | 70 | 70 | 70 | 70 |

Example B

Seeds of a variety of test species were sown in standard soil in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient of formula I in acetone/water (50:50) solution containing 0.5% Tween 20 (polyoxyethelyene sorbitan monolaurate, CAS RN 9005-64-5). The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

Test Plants:

*Setaria faberi* (SETFA), *Lolium perenne* (LOLPE), *Alopecurus myosuroides* (ALOMY), *Echinochloa crus-galli* (ECHCG), and *Avena fatua* (AVEFA).

Pre-Emergence Activity

| Compound Number | Rate g/ha | SETFA | LOLPE | ALOMY | ECHCG | AVEFA |
|---|---|---|---|---|---|---|
| T1 | 250 | 100 | — | 50 | 100 | 0 |
| T2 | 250 | 100 | — | 40 | 100 | 40 |
| T3 | 250 | 100 | — | 60 | 100 | 20 |
| T4 | 250 | — | 40 | 20 | 90 | 0 |
| T5 | 250 | — | 0 | 0 | 0 | 0 |
| T6 | 250 | — | 0 | 0 | 80 | 0 |
| T8 | 250 | — | 90 | 0 | 100 | 20 |
| T10 | 250 | — | 90 | 0 | 100 | 20 |
| T11 | 250 | — | 0 | 0 | 20 | 0 |
| T12 | 250 | — | 0 | 0 | 0 | 0 |
| T13 | 250 | — | 50 | 0 | 40 | 0 |
| T15 | 250 | — | 90 | 0 | 100 | 0 |
| T16 | 250 | — | 80 | 30 | 90 | 20 |
| T17 | 250 | — | 0 | 0 | 80 | 0 |
| T18 | 250 | — | 80 | 30 | 90 | 20 |
| T20 | 250 | — | 50 | 0 | 90 | 0 |
| T21 | 250 | — | 50 | 0 | 40 | 30 |
| T22 | 250 | — | 80 | 20 | 90 | 40 |
| T23 | 250 | — | 70 | 40 | 90 | 20 |
| T25 | 250 | — | 70 | 30 | 80 | 20 |
| T26 | 250 | — | 100 | 20 | 100 | 0 |
| T27 | 250 | — | 0 | 0 | 0 | 0 |
| T28 | 250 | — | 90 | 20 | 100 | 40 |
| T29 | 250 | — | 70 | 40 | 90 | 0 |
| T30 | 250 | — | 70 | 0 | 70 | 20 |
| T32 | 250 | — | 80 | 0 | 80 | 30 |
| T33 | 250 | — | 90 | 0 | 90 | 20 |
| T34 | 250 | — | 30 | 20 | 50 | 0 |
| T41 | 250 | — | 100 | 20 | 100 | 30 |
| T42 | 250 | — | 0 | 0 | 20 | 0 |
| T44 | 250 | — | 80 | 0 | 90 | 0 |
| T45 | 250 | — | 100 | 20 | 100 | 20 |
| T46 | 250 | — | 70 | 0 | 90 | 20 |
| T48 | 250 | — | 80 | 0 | 90 | 20 |
| T49 | 250 | — | 100 | 20 | 100 | 60 |
| T50 | 250 | — | 0 | 20 | 90 | 40 |
| T51 | 250 | — | 100 | 20 | 80 | 40 |
| T52 | 250 | — | 90 | 40 | 100 | 30 |
| T53 | 250 | — | 40 | 20 | 40 | 0 |
| T54 | 250 | — | 20 | 0 | 70 | 0 |
| T55 | 250 | — | 20 | 20 | 40 | 0 |
| T56 | 250 | — | 90 | 30 | 100 | 20 |
| T57 | 250 | — | 10 | 0 | 20 | 0 |
| T58 | 250 | — | 70 | 20 | 90 | 0 |
| T59 | 250 | — | 100 | 100 | 100 | 100 |
| T60 | 250 | — | 80 | 0 | 90 | 30 |
| T61 | 250 | — | 70 | 20 | 90 | 50 |
| T62 | 250 | — | 90 | 60 | 90 | 50 |
| T63 | 250 | — | 90 | 20 | 90 | 50 |
| T64 | 250 | — | 60 | 30 | 70 | 10 |
| T65 | 250 | — | 50 | 10 | 90 | 20 |
| T66 | 250 | — | 30 | 10 | 90 | 0 |
| T67 | 250 | — | 10 | 10 | 60 | 0 |
| T69 | 250 | — | 90 | 10 | 90 | 0 |

Post-Emergence Activity

| Compound Number | Rate g/ha | SETFA | LOLPE | ALOMY | ECHCG | AVEFA |
|---|---|---|---|---|---|---|
| T1 | 250 | 100 | — | 90 | 100 | 40 |
| T2 | 250 | 100 | — | 90 | 100 | 80 |
| T3 | 250 | 100 | — | 100 | 100 | 20 |
| T4 | 250 | — | 50 | 0 | 100 | 0 |
| T5 | 250 | — | 80 | 70 | 100 | 90 |
| T6 | 250 | — | 60 | 0 | 100 | 40 |
| T8 | 250 | — | 80 | 40 | 100 | 30 |
| T10 | 250 | — | 90 | 70 | 100 | 90 |
| T11 | 250 | — | 60 | 60 | 90 | 60 |
| T12 | 250 | — | 0 | 0 | 90 | 0 |
| T13 | 250 | — | 50 | 0 | 100 | 0 |
| T15 | 250 | — | 50 | 0 | 100 | 40 |
| T16 | 250 | — | 90 | 50 | 100 | 90 |
| T17 | 250 | — | 40 | 0 | 90 | 0 |
| T18 | 250 | — | 80 | 30 | 90 | 40 |
| T20 | 250 | — | 70 | 0 | 80 | 40 |
| T21 | 250 | — | 70 | 0 | 80 | 0 |
| T22 | 250 | — | 100 | 70 | 100 | 40 |
| T23 | 250 | — | 100 | 90 | 100 | 60 |
| T25 | 250 | — | 100 | 80 | 100 | 80 |
| T26 | 250 | — | 70 | 30 | 80 | 0 |
| T27 | 250 | — | 80 | 90 | 100 | 70 |

-continued

| Compound Number | Rate g/ha | SETFA | LOLPE | ALOMY | ECHCG | AVEFA |
|---|---|---|---|---|---|---|
| T28 | 250 | — | 100 | 30 | 100 | 50 |
| T29 | 250 | — | 100 | 40 | 100 | 30 |
| T30 | 250 | — | 100 | 80 | 100 | 60 |
| T32 | 250 | — | 100 | 40 | 100 | 70 |
| T33 | 250 | — | 100 | 100 | 100 | 80 |
| T34 | 250 | — | 100 | 100 | 100 | 100 |
| T41 | 250 | — | 100 | 60 | 90 | 50 |
| T42 | 250 | — | 50 | 50 | 100 | 20 |
| T44 | 250 | — | 80 | 30 | 100 | 0 |
| T45 | 250 | — | 100 | 40 | 100 | 90 |
| T46 | 250 | — | 70 | 0 | 100 | 20 |
| T48 | 250 | — | 50 | 20 | 100 | 10 |
| T49 | 250 | — | 90 | 50 | 100 | 80 |
| T50 | 250 | — | 80 | 70 | 100 | 80 |
| T51 | 250 | — | 90 | 40 | 90 | 50 |
| T52 | 250 | — | 100 | 70 | 100 | 80 |
| T53 | 250 | — | 100 | 40 | 100 | 80 |
| T54 | 250 | — | 60 | 20 | 80 | 0 |
| T55 | 250 | — | 60 | 40 | 100 | 10 |
| T56 | 250 | — | 100 | 60 | 100 | 100 |
| T57 | 250 | — | 60 | 50 | 80 | 40 |
| T58 | 250 | — | 90 | 60 | 100 | 90 |
| T59 | 250 | — | 100 | 100 | 100 | 100 |
| T60 | 250 | — | 80 | 10 | 100 | 30 |
| T61 | 250 | — | 40 | 10 | 90 | 30 |
| T62 | 250 | — | 80 | 60 | 80 | 80 |
| T63 | 250 | — | 80 | 20 | 80 | 40 |
| T64 | 250 | — | 80 | 50 | 100 | 80 |
| T65 | 250 | — | 50 | 20 | 80 | 30 |
| T66 | 250 | — | 30 | 30 | 100 | 50 |
| T67 | 250 | — | 40 | 20 | 80 | 20 |
| T69 | 250 | — | 100 | 20 | 100 | 40 |

What is claimed is:

1. A compound of formula I

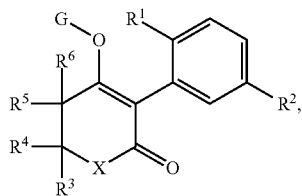

wherein

X is O, S, $CR^7R^8$ or $NR^9$, $R^1$ is ethyl, cyclopropyl, difluoromethoxy or trifluoromethoxy, $R^2$ is optionally substituted aryl or optionally substituted heteroaryl, $R^3$ and $R^4$ are independently of each other, hydrogen, $C_1$-$C_3$alkyl or $C_1$-$C_3$haloalkyl, or $R^3$ and $R^4$ together with the carbon atom to which they are attached form a three- to seven-membered carbocyclic ring, optionally substituted once or twice by $C_1$-$C_2$alkyl, $R^5$, $R^6$, $R^7$ and $R^8$ are independently of each other hydrogen, $C_1$-$C_3$alkyl, $C_1$-$C_3$haloalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkylsulfonyl$C_1$-$C_3$alkyl, $C_3$-$C_6$cycloalkyl in which a methylene group is optionally replaced by an oxygen or sulfur atom and wherein the ring is optionally substituted once or twice by $C_1$-$C_2$alkyl or $C_1$-$C_2$alkoxy, or $R^5$ and $R^6$ together with the carbon atom to which they are attached, or $R^7$ and $R^8$ together with the carbon atom to which they are attached form an optionally substituted three- to seven membered carbocyclic ring, in which a methylene group is optionally replaced by an oxygen or sulfur atom and wherein the ring is optionally substituted once or twice by $C_1$-$C_2$alkyl or $C_1$-$C_2$alkoxy, or $R^3$ and $R^6$ form a bond, when X is O, or S, $R^9$ is hydrogen, optionally substituted $C_1$-$C_3$alkyl or optionally substituted $C_3$-$C_6$cycloalkyl, and G is hydrogen or an agriculturally acceptable metal, ammonium, sulfonium or latentiating group.

2. The compound according to claim 1, wherein X is O or $CR^7R^8$, where $R^7$ and $R^8$ are as defined in claim 1.

3. The compound according to claim 2, wherein X is $CH_2$.

4. The compound according to claim 1, wherein $R^1$ is ethyl.

5. The compound according to claim 1, wherein $R^2$ is phenyl, naphthyl, a 5- or 6-membered heteroaryl or a bicyclic 8- to 10-membered heteroaryl, in each case optionally substituted by halogen, methyl, ethyl, trifluoromethyl, methoxy, difluoromethoxy, trifluoromethoxy, nitro or cyano.

6. The compound according to claim 5, wherein $R^2$ is phenyl, naphthyl, furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, in each case optionally substituted by halogen, methyl, ethyl, trifluoromethyl, methoxy, difluoromethoxy, trifluoromethoxy, nitro or cyano.

7. The compound according to claim 1, wherein $R^2$ is optionally substituted phenyl or optionally substituted pyridyl.

8. The compound according to claim 7, wherein $R^2$ is phenyl substituted one to three times by fluorine, chlorine, bromine, methoxy, methyl, cyano or trifluoromethyl.

9. The compound according to claim 1, wherein $R^3$ and $R^4$ are independently, hydrogen or $C_1$-$C_3$alkyl.

10. The compound according to claim 1, wherein $R^5$, $R^6$, $R^7$ and $R^8$ are independently of each other hydrogen, $C_1$-$C_3$alkyl, $C_1$-$C_3$alkoxy$C_1$-$C_3$alkyl, optionally substituted $C_3$-$C_6$cycloalkyl in which a ring carbon atom is optionally replaced by an oxygen or sulfur atom and wherein the ring is optionally substituted once or twice by $C_1$-$C_2$ alkyl or $C_1$-$C_2$ alkoxy, or $R^5$ and $R^6$ together with the carbon atom to which they are attached or $R^7$ and $R^8$ together with the carbon atom to which they are attached form an optionally substituted three- to seven membered carbocyclic ring, in which a ring carbon atom is optionally replaced by an oxygen or sulfur atom and wherein the ring is optionally substituted once or twice by $C_1$-$C_2$alkyl or $C_1$-$C_2$ alkoxy.

11. The compound according to claim 9, wherein $R^5$, $R^6$, $R^7$ and $R^8$ are independently of each other hydrogen, $C_1$-$C_3$alkyl, $C_1$-$C_3$alkoxy$C_1$-$C_3$alkyl, or $R^5$ and $R^6$ together with the carbon atom to which they are attached or $R^7$ and $R^8$ together with the carbon atom to which they are attached form an optionally substituted five- or six-membered carbocyclic ring, in which a ring carbon atom is optionally replaced by an oxygen atom, and wherein the ring is optionally substituted once or twice by $C_1$-$C_2$alkyl or $C_1$-$C_2$ alkoxy.

12. The compound according to claim 1, wherein G is hydrogen.

13. A process for the preparation of a compound of formula I according to claim 1, wherein G is hydrogen and X is $CR^7R^8$, which comprises reacting a compound of the formula (P)

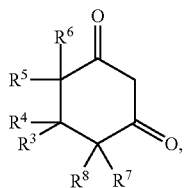

formula (P)

wherein $R^3$, $R^4$, $R^5$, $R^6$, $R^7$ and $R^8$ have the meanings assigned to them in claim 1, with an aryllead triacetate of formula (Q)

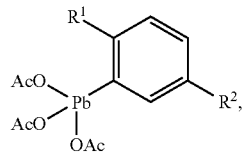

formula ($Q_1$)

wherein $R^1$ and $R^2$ have the meanings assigned to them in claim 1, in the presence of a nitrogen-containing ligand and a solvent.

14. A herbicidal composition, which, in addition to comprising formulation assistants, comprises a herbicidally effective amount of a compound of formula I.

15. A composition according to claim 14, which, in addition to comprising the compound of formula I, comprises a further herbicide as mixing partner and, optionally, a safener.

16. A method of controlling grasses and weeds in crops of useful plants, which comprises applying a herbicidally effective amount of a compound of formula I, or of a composition comprising such a compound, to the plants or to the locus thereof.

* * * * *